US006599738B2

(12) United States Patent
Potts et al.

(10) Patent No.: US 6,599,738 B2
(45) Date of Patent: Jul. 29, 2003

(54) REPORTER GENE SYSTEM FOR USE IN CELL-BASED ASSESSMENT OF INHIBITORS OF THE HEPATITIS C VIRUS PROTEASE

(75) Inventors: Karen Elizabeth Potts, Solana Beach, CA (US); Roberta Lynn Jackson, San Diego, CA (US); Amy Karen Patick, Escondido, CA (US)

(73) Assignee: Agouron Pharmaceuticals, Inc., San Diego, CA (US)

( * ) Notice: Subject to any disclaimer, the term of this patent is extended or adjusted under 35 U.S.C. 154(b) by 154 days.

(21) Appl. No.: 09/919,901

(22) Filed: Aug. 2, 2001

(65) Prior Publication Data

US 2003/0082518 A1 May 1, 2003

Related U.S. Application Data

(60) Division of application No. 09/263,933, filed on Mar. 8, 1999, now Pat. No. 6,280,940, which is a continuation-in-part of application No. 09/129,611, filed on Aug. 5, 1998, now abandoned.

(51) Int. Cl.[7] .......................... C12N 15/74; C07H 21/04

(52) U.S. Cl. ....................... 435/320.1; 435/5; 536/23.2; 536/23.4; 536/23.72

(58) Field of Search ............... 435/5, 320.1; 536/23.72, 536/23.2, 23.4

(56) References Cited

U.S. PATENT DOCUMENTS

| | | | |
|---|---|---|---|
| 5,371,017 | A | 12/1994 | Houghton et al. |
| 5,585,258 | A | 12/1996 | Houghton et al. |
| 5,597,691 | A | 1/1997 | Houghton et al. |
| 5,679,342 | A | 10/1997 | Houghton et al. |
| 5,714,596 | A | 2/1998 | Houghton et al. |
| 5,721,133 | A | 2/1998 | Dasmahapatra |
| 5,739,002 | A | 4/1998 | De Francesco et al. |

FOREIGN PATENT DOCUMENTS

| | | |
|---|---|---|
| WO | WO 96/34976 | 5/1995 |
| WO | WO 98/00548 | 6/1996 |
| WO | WO 98/16657 | 10/1996 |

OTHER PUBLICATIONS

Expression of Proteins in Mammalian Cells Using Vaccinia Viral Vectors in Current Protocols in Molecular Biology (Ausubel, F.M., et al. eds.) vol. 2, Unit 16.15.1 (1991).

Berger, J. et al. Secreted Alkaline Phosphatase: a powerful new quantitative indicator of gene expression in eukaryotic cells, Gene 56:1–10 (1988).

Cho, Y. et al., In vivo assay for hepatitis C viral serine protease activity using a secreted protein, J. Virol. Meth. 72: 109–115 (1998).

Grakoui, A. et al., Expression and Identification of Hepatitis C Virus Polyprotein Cleavage Products, J. Virol. 67:2832–2843 (1993).

Hamatake, R. et al., Establishment of an in vitro Assay to Characterize Hepatitis C NS3–4A Protease Trans–Processing Activity, Intervirology 39:249–258 (1996).

Hirowatari, Y., et al., A Novel Method for Analysis of Viral Proteinase Activity Encoded by Hepatitis C Virus in Cultured Cells, Anal. Biochem. 225:113–120 (1995).

Korant, B.,D., Viral Proteases: An Emerging Therapeutic Target, CRC Critical Reviews in Biotechnology, 8:149–157 (1988).

Love, R. et al., The Crystal Structure of Hepatitis C Virus NS3 Proteinase Reveals a Trypsin–like Fold and a Structural Zinc Binding Site, Cell 87:331–342 (1996).

Love, R. et al., The conformation of hepatitis C virus NS3 proteinase with and without NS4A: a structural basis for the activation of the enzyme by its cofactor, Clin. and Diag. Virol. 10:151–156 (1998).

Love, R. et al., Conformational Changes in Hepatitis C virus NS3 proteinase due to NS4A cofactor complexation, (Proposal 4A22) sent to Stanford Linear Accelerator Center, Apr. 6, 1998.

Stempniak, M. et al., The NS3 Proteinase Domain of Hepatitis C Virus is a Zinc–Containing Enzyme, J. Virol. 71:2881–2886 (1997).

Takamizawa, A. et al., Structure and Organization of the Hepatitis C Virus Genome Isolated from Human Carriers, J. Virol. 65:1105–1113 (1991).

Song, O. et al., Development of an in vivo Assay System Suitable for Screening Inhibitors of Hepatitis C Viral Protease, Mol. Cells 6:183–189 (1996).

Sali, DL, et al., Serine Protease of Hepatitis C Virus Expressed in Insect Cells as the NS3/4A Complex, Biochem 1998; 37:3392–3401.

Kakiuchi, N, et al., A high throughput assay of the hepatitis C virus nonstructural protein 3 serine proteinase, J of Virol Methods, 1999;80:77–84.

Zhang, R. et al., A Continuous Spectrophotometric Assay for the Hepatitis C Virus Serine Protease, Analytical Biochem, 1999; 270:268–275.

Cerretani, M. et al., A High–Throughput Radiometric Assay for Hepatitis C Virus NS3 Protease, Analytical Biochem, 1999; 266:192–197.

*Primary Examiner*—Donna C. Wortman

(74) *Attorney, Agent, or Firm*—Peter C. Richardson; Bryan C. Zielinski; Jeffrey W. Rennecker

(57) ABSTRACT

A cell-based assay system in which the detection of the reporter gene activity, or secreted alkaline phosphatase (SEAP), is dependent upon the protease activity of the Hepatitis C virus NS3 gene product. This system can be used to assess the activity of candidate protease inhibitors in a mammalian cell-based assay system. The assay system is simpler than previously described assays due to the use of SEAP which allows the reporter gene activity to be quantified by measuring the amount of secreted gene product in the cell media by monitoring the conversion of luminescent or colorimetric alkaline phosphatase substrate.

11 Claims, 11 Drawing Sheets

$NS2^{WT}$ $NS3^{WT}$/pTM3
$NS2^{WT}$ $NS3^{MUT}$/ pTM3
$NS2^{MUT}$ $NS3^{MUT}$/ pTM3
pTM3 vHCAP1 (NS3 cis & trans cleavage)

vHCAP3 ($NS3^{MUT}$)

DI/ DR Assay Compound Summary

| Compound | $EC_{50}$ (μM) | $CC_{50}$ (μM) | TI | Solubility | Activity |
|---|---|---|---|---|---|
| A | >320 | >320 | – | >320 | – |
| B | 18 | 15 | 1 | >320 | – |
| C | 37 | 41 | 1 | >320 | – |
| D | >320 | >320 | – | >320 | – |
| E | 70 | 174 | 2 | ppt>30 | – |
| F | 64 | >320 | 4 | >320 | +/– |
| G | >320 | >320 | – | >320 | – |
| H | 166 | 194 | 1 | >320 | – |
| I | 38 | 76 | 2 | >320 | – |

FIG.8

REPORTER GENE SYSTEM FOR USE IN CELL-BASED ASSESSMENT OF INHIBITORS OF THE HEPATITIS C VIRUS PROTEASE

This is a division of application Ser. No. 09/263,933, filed Mar. 8, 1999 for U.S. Pat. No. 6,280,940; which is a CIP of application Ser. No. 09/129,611, filed on Aug. 5, 1998 abandoned.

TECHNICAL AND INDUSTRIAL APPLICABILITY OF INVENTION

A cell-based assay system in which the detection of reporter gene activity (secreted alkaline phosphatase or SEAP) is dependent upon active Hepatitis C virus (HCV) NS3 protease. The assay system is useful in the in vitro screening, in a mammalian cell-based assay, of potential protease inhibiting molecules useful in the treatment of HCV. The advantages of using SEAP over more routinely used reporter genes such as beta-galactosidase or luciferase, is that a cell lysis step is not required since the SEAP protein is secreted out of the cell. The absence of a cell lysis step decreases intra- and inter-assay variability as well as makes the assay easier to perform then earlier assays.

BACKGROUND OF THE INVENTION

HCV is one of the major causes of parenterally transmitted non-A, non-B hepatitis worldwide. HCV is now known as the etiologic agent for Non-A Non-B hepatitis throughout the world. Mishiro et al., U.S. Pat. No. 5,077,193; Mishiro et al., U.S. Pat. No. 5,176,994; Takahashi et al, U.S. Pat. No. 5,032,511; Houghton et al., U.S. Pat. Nos. 5,714,596 and 5,712,088; as well as (M. Houghton, *Hepatitis C Viruses,* p. 1035–1058 in B. N. Fields et al.(eds.), *Field's Virology* (3d. ed. 1996). HCV infection is characterized by the high rate (>70%) with which acute infection progresses to chronic infection (Alter, M. J. 1995. Epidemiology of hepatitis C in the west. Sem. Liver Dis. 15:5–14.). Chronic HCV infection may lead to progressive liver injury, cirrhosis, and in some cases, hepatocellular carcinoma. Currently, there are no specific antiviral agents available for the treatment of HCV infection. Although alpha interferon therapy is often used in the treatment of HCV-induced moderate or severe liver disease, only a minority of patients exhibit a sustained response Saracco, G. et al., *J. Gastroenterol. Hepatol.* 10:668–673 1995. Additionally, a vaccine to prevent HCV infection is not yet available and it remains uncertain whether vaccine development will be complicated by the existence of multiple HCV genotypes as well as viral variation within infected individuals Martell, M. et al., *J. Virol.* 66:3225–3229 1992; Weiner, et al., Proc. Natl. Acad. Sci. 89:3468–3472 1992. The presence of viral heterogeneity may increase the likelihood that drug resistant virus will emerge in infected individuals unless antiviral therapy effectively suppresses virus replication. Most recently, several of the HCV encoded enzymes, specifically the NS3 protease and NS5B RNA polymerase, have been the focus of intensive research, in vitro screening, and/or rational drug design efforts.

HCV has been classified in the flavivirus family in a genus separate from that of the flaviviruses and the pestiviruses. Rice, C. M., in B. N. Fields and P. M. Knipe (eds.), Virology, 3rd edn., p. 931–959;1996 Lippincott-Raven, Philadelphia, Pa. Although the study of HCV replication is limited by the lack of an efficient cell-based replication system, an understanding of replicative events has been inferred from analogies made to the flaviviruses, pestiviruses, and other positive strand RNA viruses. The HCV virus has a 9.4 kb single positive-strand RNA genome encoding over 3,000 amino acids. The genome expresses over 10 structural and non-structural proteins. Post-translational processing of the viral genome requires cleavage by two proteases. As in the pestiviruses, translation of the large open reading frame occurs by a cap-independent mechanism and results in the production of a polyprotein of 3010–3030 amino acids. Proteolytic processing of the structural proteins (the nucleocapsid protein or core (C)) and two envelope glycoproteins, E1 and E2 is accomplished by the action of host cell signal peptidases. Santolini, E., et al., *J. Virol.* 68:3631–3641, 1994; Ralston, R., et al., *J. Virol.* 67:6753–6761 1993. Cleavage of the nonstructural proteins (NS4A, NS4B, NS5A, and NS5B) is mediated by the action of the NS2/3 protease or the NS3 protease. Grakoui, A. et al., *J. Virol.* 67:2832–2843 1993; Hirowatari, Y., et al., *Anal. Biochem.* 225:113–120 1995; Bartenschlager, R. et al., *J. Virol.* 68:5045–5055 1994; Eckart, M. R., et al., *Biochem. Biophys. Res. Comm.* 192:399–406 1993; Grakoui, A., et al., *J. Virol.* 67:2832–2843 1993; Tomei, L., et al., *J. Virol.* 67:4017–40261993; NS4A is a cofactor for NS3 and NS5B is an RNA dependent RNA polymerase. Bartenschlager, R. et al., (1994); Failla, C., et al., *J. Virol.* 68:3753–3760 1994; Lin, C. et al., *Proc. Natl. Acad. Sci.* 92:7622–7626 1995; Behrens, S.-E., et al., *EMBO J.* 15:12–22 1996. Functions for the NS4B and NS5A proteins have yet to be defined.

The NS2/3 is a metalloprotease and has been shown to mediate cleavage at the 2/3 junction site Grakoui, et al. (1993); Hijikata, M., et al., *J. Virol.* 67:4665–4675 1993. In contrast, the NS3 protease is required for multiple cleavages within the nonstructural segment of the polyprotein, specifically the 3/4A, 4A/4B, 4B/5A, and 5A/5B junction sites Bartenschlager et al. (1993); Eckart, M. R., et al., *Biochem. Biophys. Res. Comm.* 192:399–406 1993; Grakoui et al. (1993); Tomei et al. (1994). More recently, it is thought that the NS2/3 protease might actually be part of the HCV NS3 protease complex even though they have two functionally distinct activities. Although NS3 protease is presumed to be essential for HCV viability, definitive proof of its necessity has been hampered by the lack of an infectious molecular clone that can be used in cell-based experiments. However, recently two independent HCV infectious molecular clones have been developed and have been shown to replicate in chimpanzees. Kolykhalov, A. A., et al., *Science* 277:570–574 1997; Yanagi, M., et al., *Proc. Natl. Acad. Sci.* 94:8738–8743 1997. The requirement for NS3 in the HCV life cycle may be validated in these clones by using oligo nucleotide-mediated site directed mutagenesis to inactivate the NS3 catalytic serine residue and then determining whether infectious virus is produced in chimpanzees. Until these experiments are performed, the necessity of NS3 is inferred from cell-based experiments using the related yellow fever (YFV) and bovine viral diarrhea (BVDV) viruses. Mutagenesis of the YFV and BVDV NS3 protease homologs has shown that NS3 serine protease activity is essential for YFV and BVDV replication. Chambers, T. J., et al., *Proc. Natl. Acad. Sci.* 87:8898–8902 1990; Xu, J., et al., *J. Virol.* 71:5312–5322 1997.

In general, when investigators screen potential anti-viral compounds for inhibitory activity, it usually involves initial in vitro testing of putative enzyme inhibitors followed by testing the compounds on actual infected cell lines and animals. It is obvious that working with live virus in large scale screening activities can be inherently dangerous and problematic. While final testing of putative inhibitors in infected cells and animals is still necessary for preclinical drug development, for initial screening of candidate molecules, such work is cost-prohibitive and unnecessary. Furthermore, the inability to grow HCV in tissue culture in a reproducible quantitative manner prevents the evaluation of potential antiviral agents for HCV in a standard antiviral cytopathic effect assay. In response to this real need in the industry, development of non-infectious, cell-based, screening systems is essential.

For example, Hirowatari, et al. developed a reporter assay system, inter alia, that involves the transfection of mammalian cells with two eukaryotic expression plasmids. Hirowatari, et al., *Anal. Biochem.* 225:113–120 1995. One plasmid has been constructed to express a polyprotein that encompasses the HCV NS2-NS3 domains fused in frame to an NS3 cleavage site followed by the HTLV-1 TAX1 protein. A second plasmid has been constructed to have the expression of the chloramphenicol acetyltransferase (CAT) reporter gene under the control of the HTLV-1 LTR. Thus when COS cells are transfected with both plasmids, NS3-mediated cleavage of the TAX1 protein from the NS2-NS3-TAX1 polyprotein allows the translocation of TAX1 to the nucleus and subsequent activation of CAT transcription from the HTLV-1 LTR. CAT activity can be measured by assaying the acetylation of $^{14}$C-chloramphenicol through chromatographic or immunological methods. In the CAT assay generally, cell extracts are incubated in a reaction mix containing $^{14}$C- or $^{3}$H-labeled chloramphenicol and n-Butyryl Coenzyme A. The CAT enzyme transfers the n-butyryl moiety of the cofactor to chloramphenicol. For a radiometric scintillation detection (LSC) assay, the reaction products are extracted with a small volume of xylene. The n-butyryl chloramphenicol partitions mainly into the xylene phase, while unmodified chloramphenicol remains predominantly in the aqueous phase. The xylene phase is mixed with a liquid scintillant and counted in a scintillation counter. The assay can be completed in as little as 2–3 hours, is linear for nearly three orders of magnitude, and can detect as little as $3\times10^{-4}$ units of CAT activity. CAT activity also can be analyzed using thin layer chromatography (TLC). This method is more time-consuming than the LSC assay, but allows visual confirmation of the data.

Similarly, the other patents of Houghton, et al., U.S. Pat. Nos. 5,371,017, 5,585,258, 5,679,342 and 5,597,691 or Jang et al. WO 98/00548 all disclose a cloned NS3 protease or portion fused to a second gene encoding for a protein which a surrogate expression product can be detected for example, in the '017 patent of Houghton, b-galactosidase, superoxide dismutase, ubiquitin or in Jang, the expression is measured by the proliferation of poliovirus in cell culture) and its use for candidate screening. It is unclear in the Houghton, et al. patents, however, whether the protease described in the specification is the NS2/3 metalloprotease or NS3 serine protease. Although the serine protease is claimed, the experimental data show putative cleavage of the N-terminal SOD fusion partner at the NS2/3 junction, a function which recently has been deemed to be the domain of the NS2/3 metalloprotease (Rice, C. M., et al., *Proc. Nat. Acad. Sci.* 90:10583–10587 (1993)). Furthermore, an active soluble NS3 serine protease is not disclosed in the Houghton, et al. patents, but a insoluble protein derived from *E. coli* inclusion bodies and which was N-terminally sequenced. For purposes of the present invention the term "NS2 protease" will refer to the enzymatic activity associated with the NS2/3 metalloprotease as defined by Rice et al., and the term "NS3 protease" will refer to the serine protease located within the NS3 region of the HCV genome.

De Francesco et al., U.S. Pat. No. 5,739,002, also describes a cell free in vitro system for testing candidates which activate or inhibit NS3 protease by measuring the amount of cleaved substrate. Hirowatari et al. (1995) discloses another HCV NS3 protease assay, however, it differs from the present invention in several aspects, including the reporter gene, the expression plasmid constructs, and the method of detection. Recently, Cho et al. describe a similar SEAP reporter system for assaying HCV NS3 protease which also differs in its structure and function from the present invention. Cho et al., *J. Virol. Meth.* 72:109–115 1998. Also of interest is a NS3 protease assay system developed by Chen et al. in WO 98/37180. In the Chen et al. application, a fusion protein is described which uses NS3 protease polypeptide or various truncation analogs fused to the NS4A polypeptide or various truncation analogs and is not autocleavable. The fusion protein is then incubated with known substrates with or without inhibitors to screen for inhibitory effect.

There are a number of problems inherent in all the abovementioned assay systems. For example, the reporter gene product or analyte is many steps removed from the initial NS3 protease cleavage step, the cells used in the assay system are prokaryotic or Yeast based and must be lysed before the reporter gene product can be measured, and the surrogate marker is proliferation of live virus. All of these problems are overcome in the present invention as summarized below.

SUMMARY OF INVENTION

The present invention describes a reporter gene system for use in the cell based assessment of inhibitors of the HCV protease. Applicants point out that throughout the description of this invention, the reference to specific non-structural (NS) regions or domains of the HCV genome are functional definitions and correspond approximately to the defined sequence locations described by C. M. Rice and others. The present invention discloses the co-transfection of a target cell line with a viral vector which has been engineered to express from the T7 RNA polymerase promoter and a recombinant plasmid or viral vector which has been engineered to express a polyprotein that includes NS3 HCV serine protease and the secreted human placental alkaline phosphatase (SEAP) gene (Berger et al. 1988) under control of the T7 promoter. The present invention was designed to have a linkage between the detection of reporter gene activity and NS3 serine protease activity through construction of a segment of the HCV gene encoding the NS2-NS3-NS4A-NS4B'-sequence linked to the SEAP reporter.

Detection of NS3 protease activity is accomplished by having the release and hence, the subsequent detection, of the SEAP reporter gene to be dependent upon NS3 serine protease activity. In a preferred embodiment, the target cell line is first infected with a viral vector that expresses the T7 RNA polymerase followed by either co-infection with a second viral vector that encodes the NS3 HCV protease/SEAP polyprotein, or transfection with a plasmid that contains the same NS3/SEAP gene elements.

The SEAP enzyme is a truncated form of human placental alkaline phosphatase, in which the cleavage of the transmembrane domain of the protein allows it to be secreted from the cells into the surrounding media. SEAP activity can be detected by a variety of methods including, but not limited to, measurement of catalysis of a fluorescent substrate, immunoprecipitation, HPLC, and radiometric detection. The luminescent method is preferred due to its increased sensitivity over colorimetric detection methods, and such an assay kit is available from Tropix®. The advantages of using SEAP over more routinely used reporter genes such as beta-galactosidase or luciferase, is that a cell lysis step is not required since the SEAP protein is secreted out of the cell. The absence of a cell lysis step decreases intra- and inter-assay variability as well as makes the assay easier to perform then earlier assays in the prior art. When both the T7 promoter and NS3/SEAP constructs are present, SEAP can be detected in the cell medium within the usual viral assay timeframe of 24–48 hours, however, the timeframe should not be read as a limitation because it is theoretically possible to detect the SEAP in the media only a few hours after transfection. The medium can then be collected and analyzed. Various examples illustrating the use of this composition and method will be detailed below.

BRIEF DESCRIPTION OF THE DRAWINGS

FIG. 8 shows a summary of DI/DR assay data.

DETAILED DESCRIPTION OF A PREFERRED EMBODIMENT OF THE INVENTION

Figure 1:
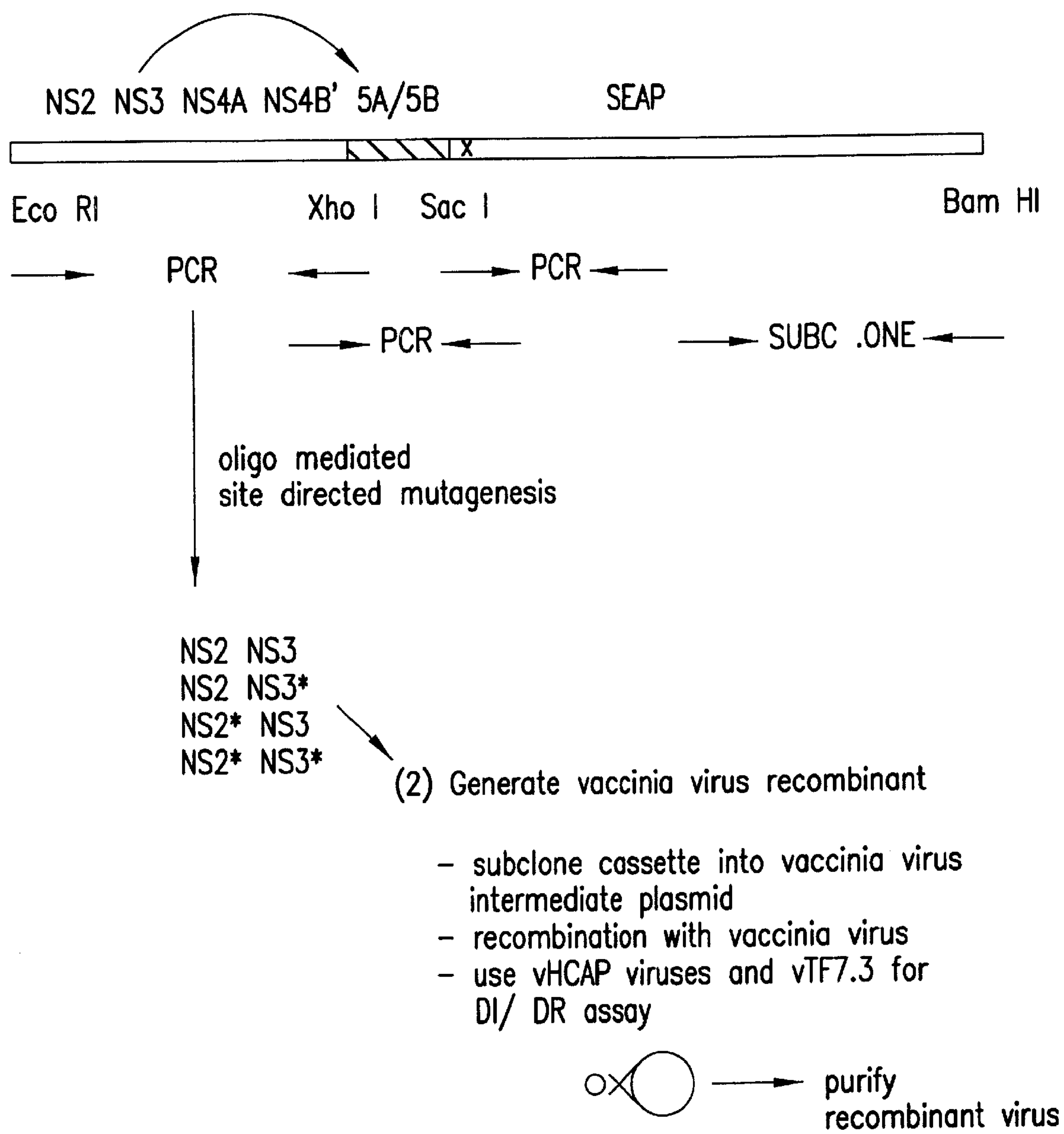
FIG. 1 illustrates schematically the Vaccinia Virus NS3/SEAP System gene construct.

The practice of this invention will employ, unless otherwise indicated, conventional techniques of molecular biology, microbiology, recombinant DNA manipulation and production, virology and immunology, which are within the skill of the art. Such techniques are explained fully in the literature: Sambrook, *Molecular Cloning; A Laboratory Manual,* Second Edition (1989); *DNA Cloning,* Volumes I and II (D. N. Glover, Ed. 1985); *Oligonucleotide Synthesis* (M. J. Gait, Ed. 1984); *Nucleic Acid Hybridization* (B. D. Hames and S. I. Higgins, Eds. 1984); *Transcription and Translation* (B. D. Hames and S. I. Higgins, Eds. 1984); *Animal Cell Culture* (R. I. Freshney, Ed. 1986); *Immobilized Cells and Enzymes* (IRL Press, 1986); B. Perbal, *A Practical Guide to Molecular Cloning* (1984); *Gene Transfer Vectors for Mammalian Cells* (J. H. Miller and M. P. Calos, Eds. 1987, Cold Spring Harbor Laboratory); *Methods in Enzymology,* Volumes 154 and 155 (Wu and Grossman, and Wu, Eds., respectively), (Mayer and Walker, Eds.) (1987); *Immunochemical Methods in Cell and Molecular Biology* (Academic Press, London), Scopes, (1987), *Expression of Proteins in Mammalian Cells Using Vaccinia Viral Vectors in Current Protocols in Molecular Biology,* Volume 2 (Frederick M. Ausubel, et al., Eds.)(1991). All patents, patent applications and publications mentioned herein, both supra and infra, are hereby incorporated by reference.

Both prokaryotic and eukaryotic host cells are useful for expressing desired coding sequences when appropriate control sequences compatible with the designated host are used. Among prokaryotic hosts, *E. coli* is most frequently used. Expression control sequences for prokaryotes include promoters, optionally containing operator portions, and ribosome binding sites. Transfer vectors compatible with prokaryotic hosts are commonly derived from, for example, pBR322, a plasmid containing operons conferring ampicillin and tetracycline resistance, and the various pUC vectors, which also contain sequences conferring antibiotic resistance markers. These plasmids are commercially available. The markers may be used to obtain successful transformants by selection. Commonly used prokaryotic control sequences include the β-lactamase (penicillinase) and lactose promoter systems (Chang et al, *Nature* (1977) 198:1056), the tryptophan (trp) promoter system (Goeddel et al, *Nuc Acids Res* (1980) 8:4057) and the lambda-derived $P_L$ promoter and N gene ribosome binding site (Shimatake et al, *Nature* (1981) 292:128) and the hybrid tac promoter (De Boer et al, *Proc Nat Acad Sci USA* (1983) 292:128) derived from sequences of the trp and lac UV5 promoters. The foregoing systems are particularly compatible with *E. coli;* if desired, other prokaryotic hosts such as strains of Bacillus or Pseudomonas may be used, with corresponding control sequences.

Eukaryotic hosts include without limitation yeast and mammalian cells in culture systems. Yeast expression hosts include Saccharomyces, Klebsiella, Picia, and the like. *Saccharomyces cerevisiae* and *Saccharomyces carlsbergensis* and *K. lactis* are the most commonly used yeast hosts, and are convenient fungal hosts. Yeast-compatible vectors carry markers which permit selection of successful transformants by conferring prototrophy to auxotrophic mutants or resistance to heavy metals on wild-type strains. Yeast compatible vectors may employ the 2$\mu$ origin of replication (Broach et al, *Meth Enzymol* (1983) 101:307), the combination of CEN3 and ARS1 or other means for assuring replication, such as sequences which will result in incorporation of an appropriate fragment into the host cell genome. Control sequences for yeast vectors are known in the art and include promoters for the synthesis of glycolytic enzymes (Hess et al, *J Adv Enzyme Reg* (1968) 7:149; Holland et al, *Biochem* (1978), 17:4900), including the promoter for 3-phosphoglycerate kinase (R. Hitzeman et al, *J Biol Chem* (1980) 255:2073). Terminators may also be included, such as those derived from the enolase gene (Holland, *J Biol Chem* (1981) 256:1385).

Mammalian cell lines available as hosts for expression are known in the art and include many immortalized cell lines available from the American Type Culture Collection (ATCC), including HeLa cells, Chinese hamster ovary (CHO) cells, baby hamster kidney (BHK) cells, BSC 1 cells, CV1 cells, and a number of other cell lines. Suitable promoters for mammalian cells are also known in the art and include vital promoters such as that from Simian Virus 40 (HV40) (Fiers et al, *Nature* (1978) 273:113), Rous sarcoma virus (RSV), adenovirus (ADV), and bovine papilloma virus (BPV). Mammalian cells may also require terminator sequences and poly-A addition sequences. Enhancer sequences which increase expression may also be included, and sequences which promote amplification of the gene may also be desirable (for example methotrexate resistance genes). These sequences are known in the art.

Vectors suitable for replication in mammalian cells are known in the art, and may include vital replicons, or sequences which insure integration of the appropriate sequences encoding HCV epitopes into the host genome. For example, another vector used to express foreign DNA is Vaccinia virus. In this case the heterologous DNA is inserted into the Vaccinia genome and transcription can be directed by either endogenous vaccinia promoters or exogenous non-vaccinia promoters (e.g. T7 retroviral promoter) known to those skilled in the art, depending on the characteristics of the constructed vector. Techniques for the insertion of foreign DNA into the vaccinia virus genome are known in the art, and may utilize, for example, homologous recombination. The heterologous DNA is generally inserted into a gene which is non-essential to the virus, for example, the thymidine kinase gene (tk), which also provides a selectable marker. Plasmid vectors that greatly facilitate the construction of recombinant viruses have been described (see, for example, Mackett et al, *J Virol* (1984) 49:857; Chakrabarti et al, *Mol Cell Biol* (1985) 5:3403; Moss, in GENE TRANSFER VECTORS FOR MAMMALIAN CELLS (Miller and Calos, eds., Cold Spring Harbor Laboratory, N.Y., 1987), p. 10). Expression of the HCV polypeptide then occurs in cells or animals which are infected with the live recombinant vaccinia virus.

In order to detect whether or not the HCV polypeptide is expressed from the vaccinia vector, BSC 1 cells may be infected with the recombinant vector and grown on microscope slides under conditions which allow expression. The cells may then be acetone-fixed, and immunofluorescence assays performed using serum which is known to contain anti-HCV antibodies to a polypeptide(s) encoded in the region of the HCV genome from which the HCV segment in the recombinant expression vector was derived.

Other systems for expression of eukaryotic or vital genomes include insect cells and vectors suitable for use in these cells. These systems are known in the art, and include, for example, insect expression transfer vectors derived from the baculovirus *Autographa californica* nuclear polyhedrosis virus (AcNPV), which is a helper-independent, viral expression vector. Expression vectors derived from this system usually use the strong viral polyhedron gene promoter to drive expression of heterologous genes. Currently the most commonly used transfer vector for introducing foreign genes into AcNPV is pAc373 (see PCT WO89/046699 and U.S. Ser. No. 7/456,637). Many other vectors known to those of skill in the an have also been designed for improved expression. These include, for example, pVL985 (which alters the polyhedron start codon from ATG to ATT, and introduces a BamHI cloning site 32 bp downstream from the ATT; See Luckow and Summers, *Virol* (1989) 17:31). AcNPV transfer vectors for high level expression of non-fused foreign proteins are described in co-pending applications PCT WO89/046699 and U.S. Ser. No. 7/456,637. A unique BamHI site is located following position −8 with respect to the translation initiation codon ATG of the polyhedron gene. There are no cleavage sites for SmaI, PstI, BglII, XbaI or SstI. Good expression of non-fused foreign proteins usually requires foreign genes that ideally have a short leader sequence containing suitable translation initiation signals preceding an ATG start signal. The plasmid also contains the polyhedron polyadenylation signal and the ampicillin-resistance (amp) gene and origin of replication for selection and propagation in *E. coli*.

Methods for the introduction of heterologous DNA into the desired site in the baculovirus virus are known in the art. (See Summer and Smith, Texas Agricultural Experiment Station Bulletin No. 1555; Smith et al, *Mol. Cell Biol. (*1983) 3:2156–2165; and Luckow and Summers, *Virol.* (1989) 17:31). For example, the heterologous DNA can be inserted into a gene such as the polyhedron gene by homologous recombination, or into a restriction enzyme site engineered into the desired baculovirus gene. The inserted sequences may be those which encode all or varying segments of the polyprotein, or other orfs which encode viral polypeptides. For example, the insert could encode the following numbers of amino acid segments from the polyprotein: amino acids 1–1078; amino acids 332–662; amino acids 406–662; amino acids 156–328, and amino acids 199–328.

The signals for post-translational modifications, such as signal peptide cleavage, proteolytic cleavage, and phosphorylation, appear to be recognized by insect cells. The signals required for secretion and nuclear accumulation also appear to be conserved between the invertebrate cells and vertebrate cells. Examples of the signal sequences from vertebrate cells which are effective in invertebrate cells are known in the art, for example, the human interleukin-2 signal ($IL2_S$) which signals for secretion from the cell, is recognized and properly removed in insect cells.

Transformation may be by any known method for introducing polynucleotides into a host cell, including, for example packaging the polynucleotide in a virus and transducing a host cell with the virus, and by direct uptake of the polynucleotide. The transformation procedure used depends upon the host to be transformed. Bacterial transformation by direct uptake generally employs treatment with calcium or rubidium chloride (Cohen, *Proc. Nat. Acad. Sci. USA* (1972) 69:2110; T. Maniatis et at, "Molecular Cloning; A Laboratory Manual" (Cold Spring Harbor Press, Cold Spring Harbor, N.Y., 1982). Yeast transformation by direct uptake may be carried out using the method of Hinnen et al, *Proc. Nat. Acad. Sci. USA* (1978) 75:1929. Mammalian transformations by direct uptake may be conducted using the calcium phosphate precipitation method of Graham and Van der Eb, *Virol.* (1978) 52:546, or the various known modifications thereof. Other methods for introducing recombinant polynucleotides into cells, particularly into mammalian cells, include dextran-mediated transfection, calcium phosphate mediated transfection, polybrene mediated transfection, protoplast fusion, electroporation, encapsulation of the polynucleotide(s) in liposomes, and direct microinjection of the polynucleotides into nuclei.

Vector construction employs techniques which are known in the art. Site-specific DNA cleavage is performed by treating with suitable restriction enzymes under conditions which generally are specified by the manufacturer of these commercially available enzymes. In general, about 1 mg of plasmid or DNA sequence is cleaved by 1 unit of enzyme in about 20 mL buffer solution by incubation for 1–2 hr at 37° C. After incubation with the restriction enzyme, protein is removed by phenol/chloroform extraction and the DNA recovered by precipitation with ethanol. The cleaved fragments may be separated using polyacrylamide or agarose gel electrophoresis techniques, according to the general procedures described in *Meth. Enzymol.* (1980) 65:499–560.

Sticky-ended cleavage fragments may be blunt ended using *E. coli* DNA polymerase I (Klenow fragment) with the appropriate deoxynucleotide triphosphates (dNTPs) present in the mixture. Treatment with S1 nuclease may also be used, resulting in the hydrolysis of any single stranded DNA portions.

Ligations are carried out under standard buffer and temperature conditions using T4 DNA ligase and ATP; sticky end ligations require less ATP and less ligase than blunt end ligations. When vector fragments are used as part of a ligation mixture, the vector fragment is often treated with bacterial alkaline phosphatase (BAP) or calf intestinal alkaline phosphatase to remove the 5'-phosphate, thus preventing re-ligation of the vector. Alternatively, restriction enzyme digestion of unwanted fragments can be used to prevent ligation. Ligation mixtures are transformed into suitable cloning hosts, such as *E. coli,* and successful transformants selected using the markers incorporated (e.g., antibiotic resistance), and screened for the correct construction.

Synthetic oligonucleotides may be prepared using an automated oligonucleotide synthesizer as described by Warner, *DNA* (1984) 3:401. If desired, the synthetic strands may be labeled with $^{32}P$ by treatment with polynucleotide kinase in the presence of $^{32}P$-ATP under standard reaction conditions.

DNA sequences, including those isolated from cDNA libraries, may be modified by known techniques, for example by site directed mutagenesis (see e.g., Zoller, *Nuc. Acids Res.* (1982) 10:6487). Briefly, the DNA to be modified is packaged into phage as a single stranded sequence, and converted to a double stranded DNA with DNA polymerase, using as a primer a synthetic oligonucleotide complementary to the portion of the DNA to be modified, where the desired modification is included in the primer sequence. The resulting double stranded DNA is transformed into a phage-supporting host bacterium. Cultures of the transformed bacteria which contain copies of each strand of the phage are plated in agar to obtain plaques. Theoretically, 50% of the new plaques contain phage having the mutated sequence, and the remaining 50% have the original sequence. Replicates of the plaques are hybridized to labeled synthetic probe at temperatures and conditions which permit hybridization with the correct strand, but not with the unmodified sequence. The sequences which have been identified by hybridization are recovered and cloned.

DNA libraries may be probed using the procedure of Grunstein and Hogness *Proc. Nat. Acad. Sci. USA* (1975) 73:3961. Briefly, in this procedure the DNA to be probed is immobilized on nitrocellulose filters, denatured, and pre-hybridized with a buffer containing 0–50% formamide, 0.75M NaCl, 75 mM Na citrate, 0.02% (wt/v) each of bovine serum albumin, polyvinylpyrrolidone, and Ficoll®, 50 mM $NaH_2PO_4$ (pH 6.5), 0.1% SDS, and 100 m g/mL carrier denatured DNA. The percentage of formamide in the buffer, as well as the time and temperature conditions of the pre-hybridization and subsequent hybridization steps depend on the stringency required. Oligomeric probes which require lower stringency conditions are generally used with low percentages of formamide, lower temperatures, and longer hybridization times. Probes containing more than 30 or 40 nucleotides, such as those derived from cDNA or genomic sequences generally employ higher temperatures, e.g., about 40°–42° C., and a high percentage formamide, e.g., 50%. Following pre-hybridization, 5'-$^{32}P$-labeled oligonucleotide probe is added to the buffer, and the filters are incubated in this mixture under hybridization conditions. After washing, the treated filters are subjected to autoradiography to show the location of the hybridized probe; DNA in corresponding locations on the original agar plates is used as the source of the desired DNA.

For routine vector constructions, ligation mixtures are transformed into *E. coli* strain HB101 or other suitable hosts, and successful transformants selected by antibiotic resistance or other markers. Plasmids from the transformants are then prepared according to the method of Clewell et al, *Proc. Nat. Acad. Sci. USA* (1969) 62:1159, usually following chloramphenicol amplification (Clewell, *J. Bacteriol.* (1972) 110:667). The DNA is isolated and analyzed, usually by restriction enzyme analysis and/or sequencing. Sequencing may be performed by the dideoxy method of Sanger et at, *Proc. Nat. Acad. Sci. USA* (1977) 74:5463, as further described by Messing et at, *Nuc. Acids Res.* (1981) 9:309, or by the method of Maxam et at, *Meth. Enzymol.* (1980) 65:499. Problems with band compression, which are sometimes observed in GC-rich regions, were overcome by use of T-deazoguanosine according to Barr et al, *Biotechniques* (1986) 4:428.

Target plasmid sequences are replicated by a polymerizing means which utilizes a primer oligonucleotide to initiate the synthesis of the replicate chain. The primers are selected so that they are complementary to sequences of the plasmid. Oligomeric primers which are complementary to regions of the sense and antisense strands of the plasmids can be designed from the plasmid sequences already known in the literature.

The primers are selected so that their relative positions along a duplex sequence are such that an extension product synthesized from one primer, when it is separated from its template (complement), serves as a template for the extension of the other primer to yield a replicate chain of defined length.

The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the agent for polymerization. The exact lengths of the primers will depend on many factors, including temperature and source of the primer and use of the method. For example, depending on the complexity of the target sequence, the oligonucleotide primer typically contains about 15–45 nucleotides, although it may contain more or fewer nucleotides. Short primer molecules generally require cooler temperatures to form sufficiently stable hybrid complexes with the template.

The primers used herein are selected to be "substantially" complementary to the different strands of each specific sequence to be amplified. Therefore, the primers need not reflect the exact sequence of the template, but must be sufficiently complementary to selectively hybridize with their respective strands. For example, a non-complementary nucleotide fragment may be attached to the 5'-end of the primer, with the remainder of the primer sequence being complementary to the strand. Alternatively, non-complementary bases or longer sequences can be interspersed into the primer, provided that the primer has sufficient complementarity with the sequence of one of the strands to be amplified to hybridize therewith, and to thereby form a duplex structure which can be extended by the polymerizing means. The non-complementary nucleotide sequences of the primers may include restriction enzyme sites. Appending a restriction enzyme site to the end(s) of the target sequence would be particularly helpful for cloning of the target sequence.

It will be understood that "primer", as used herein, may refer to more than one primer, particularly in the case where there is some ambiguity in the information regarding the terminal sequence(s) of the target region to be amplified. Hence, a "primer" includes a collection of primer oligonucleotides containing sequences representing the possible variations in the sequence or includes nucleotides which allow a typical basepairing.

The oligonucleotide primers may be prepared by any suitable method. Methods for preparing oligonucleotides of specific sequence are known in the art, and include, for example, cloning and restriction of appropriate sequences, and direct chemical synthesis. Chemical synthesis methods may include, for example, the phosphotriester method described by Narang et al. (1979), the phosphodiester method disclosed by Brown et al. (1979), the diethylphosphoramidate method disclosed in Beaucage et al. (1981), and the solid support method in U.S. Pat. No. 4,458,066. The primers may be labeled, if desired, by incorporating means detectable by spectroscopic, photochemical, biochemical, immunochemical, or chemical means.

Template-dependent extension of the oligonucleotide primer(s) is catalyzed by a polymerizing agent in the presence of adequate amounts of the four deoxyribonucleotide triphosphates (dATP, dGTP, dCTP and dTTP) or analogs, in a reaction medium which is comprised of the appropriate salts, metal cations, and pH buffering system. Suitable polymerizing agents are enzymes known to catalyze primer- and template-dependent DNA synthesis. Known DNA polymerases include, for example, *E. coli* DNA polymerase I or its Klenow fragment, $T_4$ DNA polymerase, and Taq DNA polymerase. The reaction conditions for catalyzing DNA synthesis with these DNA polymerases are known in the art.

The products of the synthesis are duplex molecules consisting of the template strands and the primer extension strands, which include the target sequence. These products, in turn, serve as template for another round of replication. In the second round of replication, the primer extension strand of the first cycle is annealed with its complementary primer; synthesis yields a "short" product which is bounded on both the 5'- and the 3'-ends by primer sequences or their complements. Repeated cycles of denaturation, primer annealing, and extension result in the exponential accumulation of the target region defined by the primers. Sufficient cycles are run to achieve the desired amount of polynucleotide containing the target region of nucleic acid. The desired amount may vary, and is determined by the function which the product polynucleotide is to serve.

The PCR method can be performed in a number of temporal sequences. For example, it can be performed step-wise, where after each step new reagents are added, or in a fashion where all of the reagents are added simultaneously, or in a partial step-wise fashion, where fresh reagents are added after a given number of steps.

In a preferred method, the PCR reaction is carried out as an automated process which utilizes a thermostable enzyme. In this process the reaction mixture is cycled through a denaturing region, a primer annealing region, and a reaction region. A machine may be employed which is specifically adapted for use with a thermostable enzyme, which utilizes temperature cycling without a liquid handling system, since the enzyme need not be added at every cycle. This type of machine is commercially available from Perkin Elmer Cetus Corp.

After amplification by PCR, the target polynucleotides are detected by hybridization with a probe polynucleotide which forms a stable hybrid with that of the target sequence under stringent to moderately stringent hybridization and wash conditions. If it is expected that the probes will be completely complementary (i.e., about 99% or greater) to the target sequence, stringent conditions will be used. If some mismatching is expected, for example if variant strains are expected with the result that the probe will not be completely complementary, the stringency of hybridization may be lessened. However, conditions are chosen which rule out nonspecific/adventitious binding. Conditions which affect hybridization, and which select against nonspecific binding are known in the art, and are described in, for example, Maniatis et al. (1982). Generally, lower salt concentration and higher temperature increase the stringency of binding. For example, it is usually considered that stringent conditions are incubation in solutions which contain approximately 0.1×SSC, 0.1% SDS, at about 65° C. incubation/wash temperature, and moderately stringent conditions are incubation in solutions which contain approximately 1–2× SSC, 0.1% SDS and about 50°–65° C. incubation/wash temperature. Low stringency conditions are 2×SSC and about 30°–50° C.

Probes for plasmid target sequences may be derived from well known restriction sites. The plasmid probes may be of any suitable length which span the target region, but which exclude the primers, and which allow specific hybridization to the target region. If there is to be complete complementarity, i.e., if the strain contains a sequence identical to that of the probe, since the duplex will be relatively stable under even stringent conditions, the probes may be short, i.e., in the range of about 10–30 base pairs. If some degree of mismatch is expected with the probe, i.e., if it is suspected that the probewill hybridize to a variant region, the probe may be of greater length, since length seems to counterbalance some of the effect of the mismatch(es).

The probe nucleic acid having a sequence complementary to the target sequence may be synthesized using similar techniques described supra. for the synthesis of primer sequences. If desired, the probe may be labeled. Appropriate labels are described supra.

In some cases, it may be desirable to determine the length of the PCR product detected by the probe. This may be particularly true if it is suspected that variant plasmid products may contain deletions within the target region, or if one wishes to confirm the length of the PCR product. In such cases it is preferable to subject the products to size analysis as well as hybridization with the probe. Methods for determining the size of nucleic acids are known in the art, and include, for example, gel electrophoresis, sedimentation in gradients, and gel exclusion chromatography.

The presence of the target sequence in a biological sample is detected by determining whether a hybrid has been formed between the polynucleotide probe and the nucleic acid subjected to the PCR amplification technique. Methods to detect hybrids formed between a probe and a nucleic acid sequence are known in the art. For example, for convenience, an unlabeled sample may be transferred to a solid matrix to which it binds, and the bound sample subjected to conditions which allow specific hybridization with a labeled probe; the solid matrix is than examined for the presence of the labeled probe. Alternatively, if the sample is labeled, the unlabeled probe is bound to the matrix, and after the exposure to the appropriate hybridization conditions, the matrix is examined for the presence of label. Other suitable hybridization assays are described supra. Analysis of the nucleotide sequence of the target region(s) may be by direct analysis of the PCR amplified products. A process for direct sequence analysis of PCR amplified products is described in Saiki et al. (1988).

Alternatively, the amplified target sequence(s) may be cloned prior to sequence analysis. A method for the direct cloning and sequence analysis of enzymatically amplified genomic segments has been described by Scharf (1986). In the method, the primers used in the PCR technique are modified near their 5'-ends to produce convenient restriction sites for cloning directly into, for example, an M13 sequencing vector. After amplification, the PCR products are cleaved with the appropriate restriction enzymes. The restriction fragments are ligated into the M13 vector, and transformed into, for example, a JM 103 host, plated out, and the resulting plaques are screened by hybridization with a labeled oligonucleotide probe. Other methods for cloning and sequence analysis are known in the art.

Construction of the HCV/SEAP Reporter Gene Plasmid

General Method

In the first embodiment, the Tropix® pCMV/SEAP expression vector is used as a starting point for construction of the HCV NS3 protease plasmid construct pHCAP1 (Seq. ID. NOS. 1–7). pHCAP1 is constructed from the pTM3 vector (Moss et al., *Nature,* 348:91–92 (1990)) in which the nucleotide sequence encoding the portion of the HCV-BK polyprotein domains NS2-NS3-NS4A-NS4B was cloned from the pBKCMV/NS2-NS3-NS4A-NS4B-SEAP (the pBK/HCAP) construct. pBK/HCAP is the eukaryotic expression plasmid in which all the original subcloning and ligation of all the HCV NS gene fragments and SEAP gene was created in. pCMV/SEAP is a mammalian expression vector designed for studies of promoter/enhancer elements with SEAP as a reporter (Berger et al., (1988)). The vector contains a polylinker for promoter/enhancer insertion, as well as an intron and polyadenylation signals from SV40. The vector can be propagated in *E.coli* due to the pUC19 derived origin of replication and ampicillin resistance gene. Modification of the commercially available plasmids is accomplished by use of PCR techniques including mutational PCR. Although this particular plasmid is described in the examples that follow, it is not the only plasmid or vector which may be used. The T7 RNA polymerase promoter is part of the pTM3 plasmid which was preferred in construction of the pHCAP vector.

In an alternate embodiment, the pTKgptF2s plasmid (Falkner and Moss, *J. Virol.* 62:1849–1854 (1988)) can be used instead of the pTM3 plasmid, which places the HCV/SEAP gene construct under transcriptional control of the native vaccinia virus promoter. The only requirement is that the promoter operate when placed in a plasmid having vaccinia virus regions flanking the subcloning region. This requirement allows the plasmid homologous recombination with the wild type vaccinia virus. Other vaccinia virus intermediate plasmids would be operable here as well.

EXAMPLE 1

The Tropix® pCMV/SEAP expression vector is first modified so that both Sac1 restriction sites are inactivated. This is done by cleaving the plasmid with BamH1 which results in a 5' cleavage product that contains the plasmid 5' ATG site and about 250 bp ending at the Bam H1 site, and a 3' cleavage product having BamH1 sites at its 5' end and at its 3' end. The 5' cleavage fragment was then amplified from the pCMV/SEAP plasmid using primers that were designed to delete the 5' ATG codon and to create a Sac 1 site on the 5' end. The downstream 3' primer spanned the Bam H1 site that is present within the SEAP coding sequence. Thus after PCR, the amplified 5' fragment has a 5' Sac 1 site and a Bam H1 site. The 5' primer introduced an extra codon (a glutamic acid residue) in front of the first leucine residue of the SEAP secretion signal. Furthermore, the first leucine codon was changed from a CTG to a CTC codon (a silent change). The codon change was made to create the second half of the Sac 1 site:

5'-GAGCTC-X-GGATCC-3' (Seq. ID NO:22) Sac 1 site 5' end of SEAP Bam H1

The modified sequence is then cloned into pGEM3Zf(+) (Promega). The Bam H1-Bam H1 SEAP fragment was subcloned into pAlter-1 (Promega) which is a plasmid that has an f1 origin of replication so it produces a single strand DNA for use in oligo mediated site directed mutagenesis. The Sac 1 sites within the SEAP fragment were mutated by oligo mediated site directed mutagenesis (GAGCTC to GAGCTG—a silent change) and the same change at the second Sac 1 site (GAGCTC to GAGCTG—an amino acid change from Serine to Cysteine) The complete SEAP pGEM3Zf(+) plasmid is then made by subcloning the PCR modified 5' SEAP fragment into the Sac I-Bam H1 sites of pGEM3Zf(+). The resulting plasmid was then linearized with Bam H1 to allow the subcloning of the 3' SEAP Bam H1-Bam H1 from the pAlter-1 plasmid which was used for the oligo mediated site directed mutagenesis to disrupt the two internal Sac I sites. A clone with the correct orientation of the Bam H1-Bam H1 fragment distal to the 5' SEAP fragment was selected after of purified plasmid DNA by restriction enzyme digest. This clone was used in the subsequent subcloning steps for the construction of the HCV/SEAP construct.

The coding sequences for the HCV proteins and NS3 cleavage sites that comprise the final HCV/SEAP polyprotein were generated in two separate PCRs from cDNA of the HCV-BK strain (Accession No. M58335). Takamizawa, A., et al., *J. Virol.* 65:1105–1113 1991. The first amplified fragment starts with the amino acid coding sequence of the HCV polyprotein corresponding to the C-terminal 81 amino acids of the putative E2 region, which are upstream of the beginning of the putative NS2 region or amino acid 729

(ARVCACLWMMLLIAQAEAALENLVVLNSASVAGA-
HGILSFLVFFCAAWYIKGRLVPGATYALYGVWPLL-
LLLLALPPRAYAMDREMAA) (Seq. ID NO:23)

or nucleotide 2187

(GCACGTGTCTGTGCCTGCTTGTGGATGATGCTGC-
TGATAGCCCAGGCCGAGGCCGCCTTGGAGAAC-
CTGGTGGTCCTCAATGCGGCGTCTGTGGCCGGC-
GCACATGGCATCCTCTCCTTCCTTGTGTTCTTCT-
GTGCCGCCTGGTACATCAAAGGCAGGCTGGTCC-
CTGGGGCGGCATATGCTCTTTATGGCGTGTGGCC-
GCTGCTCCTGCTCTTGCTGGCATTACCACCGCG-
AGCTTACGCCATGGACCGGGAGATGGC) (Seq. ID NO:24)

and contains the DNA encoding the HCV polyprotein domains NS2-NS3-NS4A through the first 176 amino acids of the NS4B gene (CASHLPYIEQ GMQLAEQFKQ KALGLLQTAT KQAE-
AAAPVV ESKWRALETF WAKHMWNFIS GIQYLA-
GLST LPGNPAIASL MAFTASITSPLTTQSTLLFN
ILGGWVAAQL APPSAASAFV GAGIAGAAVG
SIGLGKVLVD ILAGYGAGVAGALVAFKVMS
GEMPSTEDLV NLLPAIL) (Seq. ID NO:25)

or amino acid 1886 or nucleotide 5658

(TGCGCCTCGCACCTCCCTTACATCGAGCAGGGAA-
TGCAGCTCGCCGAGCMTTCAAGCAGAAAGCGC-
TCGGGTTACTGCAAACAGCCACCAAACAAGCG-
GAGGCTGCTGCTCCCGTGGTGGAGTCCAAGTG-
GCGAGCCCTTGAGACATTCTGGGCGAAGCACAT-
GTGGAATTTCATCAGCGGGATACAGTACTTAGC-
AGGCTTATCCACTCTGCCTGGGAACCCCGCAAT-
AGCATCATTGATGGCATTCACAGCCTCTATCACC-
AGCCCGCTCACCACCCAAAGTACCCTCCTGTTT-
AACATCTTGGGGGGGTGGGTGGCTGCCCAACTC-
GCCCCCCCCAGCGCCGCTTCGGCTTTCGTGGGC-
GCCGGCATCGCCGGTGCGGCTGTTGGCAGCATA-
GGCCTTGGGAAGGTGCTTGTGGACATTCTGGCG-
GGTTATGGAGCAGGAGTGGCCGGCGCGCTCGT-
GGCCIITAAGGTCATGAGCGGCGAGATGCCCTCC-

ACCGAGGACCTGGTCAATCTACTTCCTGCCATC) (Seq. ID NO:26)

The primers used to amplify the fragment were designed to contain an Eco RI site and an ATG codon in the 5' primer (Seq. ID NO:27) and an Xho I site in the 3' primer (Seq. ID NO:28). The amplified fragment was accordingly subcloned as an Eco RI-Xho I fragment into pET24a(+) plasmid (Novagen). The second fragment amplified from the HCV strain BK cDNA encompasses the putative NS5A/5B cleavage site (EEASEDVVCCSMSYTWTGAL) (Seq. ID NO:29). The 5' primer that was used to amplify the cleavage site was designed to have an Xho I site (Seq. ID NO:30) whereas the 3' primer was designed to have a Sac I site (Seq. ID NO:31). The resulting PCR product was subcloned as an Xho I-Sac I fragment into pET24a(+), which had been digested with Xho I-Hind III, as part of a three way ligation (Seq. ID NO:32). The third fragment in the three way ligation was the Sac I-Hind III fragment from the SEAP pGEM3Zf(+) plasmid. The Sac I-Hind III fragment encompassed the modified SEAP gene and also 30 base pairs of the pGEM3Zf(+) polylinker which included the multiple cloning sites (MCS) between the Bam H1 and HindIII sites. The final HCV/SEAP construct was assembled using pBKCMV as the vector. pBKCMV was digested with Eco RI and Hind III and then used in a three way ligation with the NS5A/5B-SEAP Xho I-Hind III fragment and the Eco RI-Xho I NS2-NS4B fragment.

The control plasmids for the assay (pHCAP3, pHCAP4) were constructed in a similar manner to the HCV/SEAP construct. The control plasmids have either an inactive form of NS3 protease or inactive forms of both NS2 protease and NS3 protease. Inactivation of NS2 and NS3 proteases was accomplished by oligo mediated site directed mutagenesis performed on the PCR amplified NS2-NS4B fragment that had been subcloned into pALTER-1 as an Eco R1-Xho 1 fragment together with the NS5A/5B Xho 1-Sac 1 fragment. In order to inactivate the NS3 protease, the catalytic serine residue was substituted with an alanine by replacing thymidine (<u>T</u>CG) with guanine (<u>G</u>CG) (base 2754). The NS2 protease was inactivated by substitution of the catalytic cysteine residue with an alanine residue (<u>TGT</u>-><u>GCT</u>)(bases 2238–2239). The resulting inactivated NS3 protease and inactivated NS2-NS3 proteases variants of the NS2-NS4B fragment were each subcloned into pBKCMV as separate Eco R1-Xho 1 fragments together with the NS5A/5B-SEAP Xho 1- Hind III fragment.

The pHCAP1 ($NS2^{WT}NS3^{WT}$) (Seq. ID NOS:1–7), pHCAP3 ($NS2^{WT}NS3^{WT}$) (Seq. ID NOS:8–14), and pHCAP4 ($NS_2$MUTN$S_3$ MUT) (Seq. ID NOS:15–21) plasmids were constructed using pTM3 as the vector and the appropriate HCV/SEAP fragment from the corresponding pBKHCV/SEAP constructs. The pBKHCV/SEAP constructs were first digested with Eco R1 and the Eco R1 site was filled in using Klenow fragment in a standard fill in reaction. The pBKHCV/SEAP constructs were then digested with Xba I and the gel purified HCV/SEAP fragment was subcloned into pTM3 that had been digested with Sma 1 and Spe 1. Subcloning the HCV/SEAP fragment into the Sma I site will result in an additional 6 amino acids (MGIPQF) (Seq. ID NO:33) at the N-terminus (codons 1426–1444) if the preferred translational start codon, which is part of the Nco 1 site in pTM3, is used.

The pHCAP1 ($NS2^{WT}NS3^{WT}$), pHCAP3 ($NS2^{WT}NS_3^{WT}$), and pHCAP4 ($NS2^{MUT}NS3^{MUT}$) plasmids have been used to generate recombinant vaccinia viruses as described in the next section.

Construction of the HCV/SEAP Reporter Gene Viral Vectors

Applicants have generated recombinant vaccinia virus using pHCAP1 and the control plasmids, pHCAP3 and pHCAP4. Recombinant vaccinia viruses were generated using standard procedures in which BSC-1 cells were infected with wild type vaccinia virus (strain WR from ATCC) and then transfected with either pHCAP1, pHCAP3, or pHCAP4. Selection of recombinant virus was performed by growth of infected transfected cells in the presence of mycophenolic acid. The recombinant vaccinia viruses are termed vHCAP1, vHCAP3, and vHCAP4 and correspond directly with the pHCAP1, pHCAP3, and pHCAP4 plasmids. Large scale stocks of the vHCAP1, vHCAP3, and vHCAP4 were grown and titered in CV1 cells.

Transfection of Cell Lines Containing the HCV/SEAP Reporter

Figure 2:
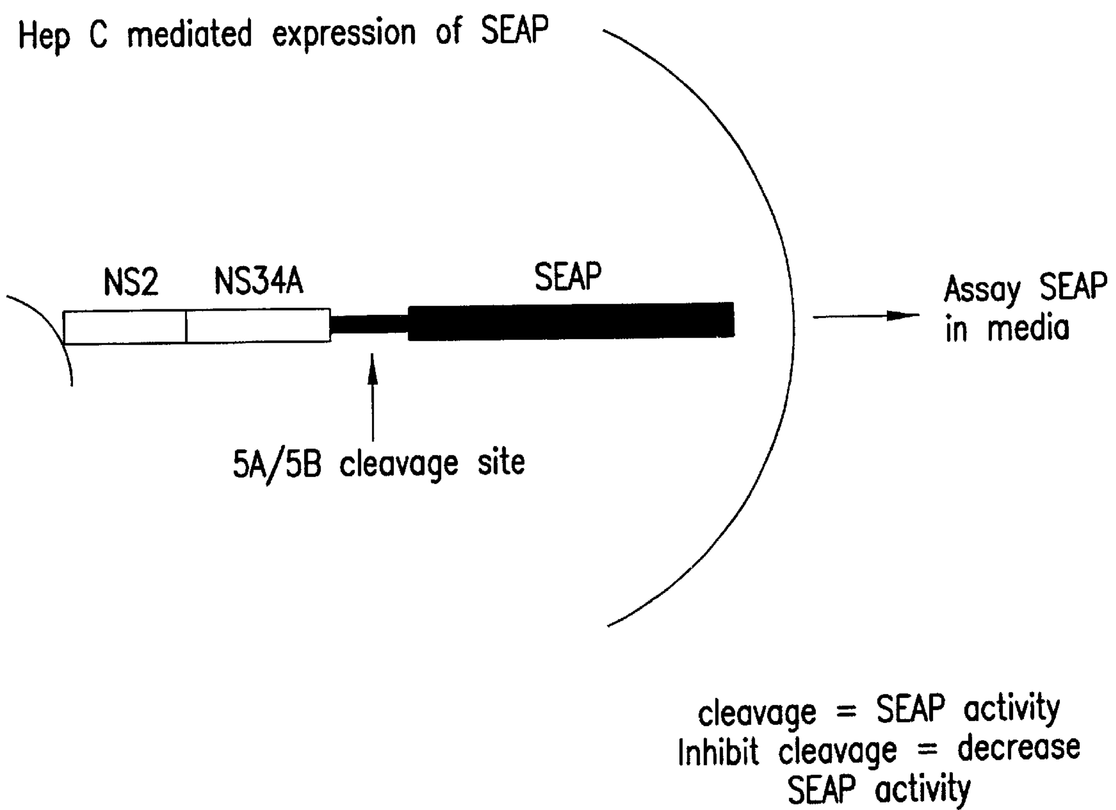
FIG. 2 illustrates schematically how the assay operates.

In the first embodiment HeLa cells are transfected with the Hep C/SEAP reporter gene plasmid, pHCAP1, and co-infection with a vTF7.3, a recombinant vaccinia virus (Fuerst et al., *Proc. Nat. Acad. Sci. USA,* 86:8122–8126 (1986)). vTF7.3 expresses T7 RNA polymerase which is required for transcription of the reporter gene since it is under the control of T7 promoter in the pTM3 plasmid. The pTM3 plasmid is a vaccinia intermediate plasmid which can function as an expression vector in cells when T7 RNA polymerase is provided in trans (FIG. 2).

As described previously, the Hep C/SEAP reporter gene encodes for a polyprotein with the following gene order: HCV (strain BK) NS2-NS3-NS4A-NS4B'-NS5A/5B cleavage site-SEAP. Thus the HCV sequences for the amino acid coding sequence of the HCV polyprotein corresponding to the C-terminal 81 amino acids of the putative E2 region, which are upstream of the start of the putative NS2 region (as defined by Grakoui et al. ) or amino acid 729 and continues through the first 176 amino acids of the NS4B gene or amino acid 1886 (Seq. ID NOS:23–26), and is proximal to the SEAP protein (see FIG. 1). The NS5A/5B cleavage site has been engineered between the end of NS4B' and the second codon of SEAP.

Figure 1B:
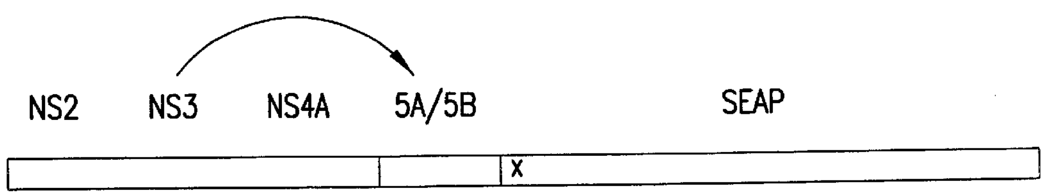
FIG. 1B illustrates schematically the Plasmid/Vaccinia Virus NS3/SEAP assay.
Figure 1B:
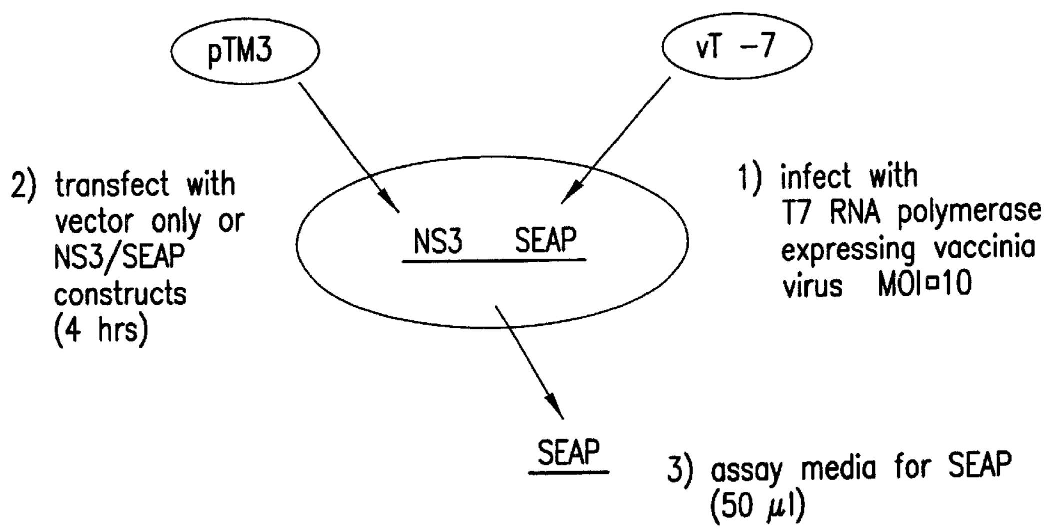

The working theory behind the unique design of the reporter gene construct is that the SEAP polyprotein is tethered, as part of the NS2-NS3-NS4A-NS4B '-NS5A/5B cleavage site-SEAP polyprotein, inside the cell. It has been shown that NS2 is a hydrophobic protein and is associated with the outside of the endoplasmic reticulum (ER). Grakoui, et al. (1993). Thus, in the present invention, SEAP is tethered to the ER via the action of NS2. Release of SEAP from the polyprotein tether will occur upon NS3-mediated cleavage at the NS5A/5B cleavage site. SEAP is then secreted from the cell and can be monitored by assaying media for alkaline phosphatase activity (FIG. 1B). It is assumed that it is NS3-mediated cleavage at the NS5A5B site which is the necessary cleavage to release SEAP from the upstream polyprotein sequences. However NS3-mediated cleavage at other sites within the polyprotein may be responsible for SEAP release and hence its subsequent secretion. Both NS3 and NS3/NS4A, where NS4A is a cofactor for NS3, can mediate cleavage at the NS3/4A and NS4A/4B cleavage sites which are present in polyprotein in addition to the engineered NS5A/5B cleavage site. Thus there may be more than one NS3-mediated cleavage event occurring over the length of the polyprotein before SEAP is available to the cell secretion apparatus and secreted from the cell. Further, in an alternative embodiments the tether may be changed depending upon the chosen cleavage site. In addition, NS2 is an autocatalytic protease; it mediates the cleavage event between it's carboxy-terminal end and the NS3 N-terminus. In the Hep C/SEAP polyprotein, NS2-mediated cleavage at the NS2/NS3 site would release the NS3-NS4A-NS4B'-SEAP polyprotein from the ER.

The above described system can be used to evaluate potent NS3 inhibitors by monitoring the effect of increasing drug concentration on SEAP activity. NS3 inhibition would be detected as a decrease in SEAP activity. Recognizing that a decrease in SEAP activity could also be due to cell cytotoxicity of a given compound or a non-specific effect on vaccinia virus which would adversely effect SEAP transcription, appropriate controls are used as discussed below.

In an alternate embodiment, a "cis-only" cleavage assay is contemplated. In this assay the $NS2^{MUT}NS3^{WT}$ variant of the HCV/SEAP (HCAP2) is used so the polyprotein remains tethered to the outside of the endoplasmic reticulum because the NS2 protease cannot catalyze the cleavage between the C-terminus and the NS3 N-terminus. Thus the only way for SEAP to be released from the tether is if the NS3 protease clips in cis at the NS5A/5B cleavage site. There should not be any trans NS3 mediated cleavage events occurring since NS2 is not available to release the NS3 N-terminus from its tether. The control plasmid or virus for this assay is the $NS2^{MUT}NS3^{MUT}$ variant HCAP4.

DI/DR Assay

Figure 3:
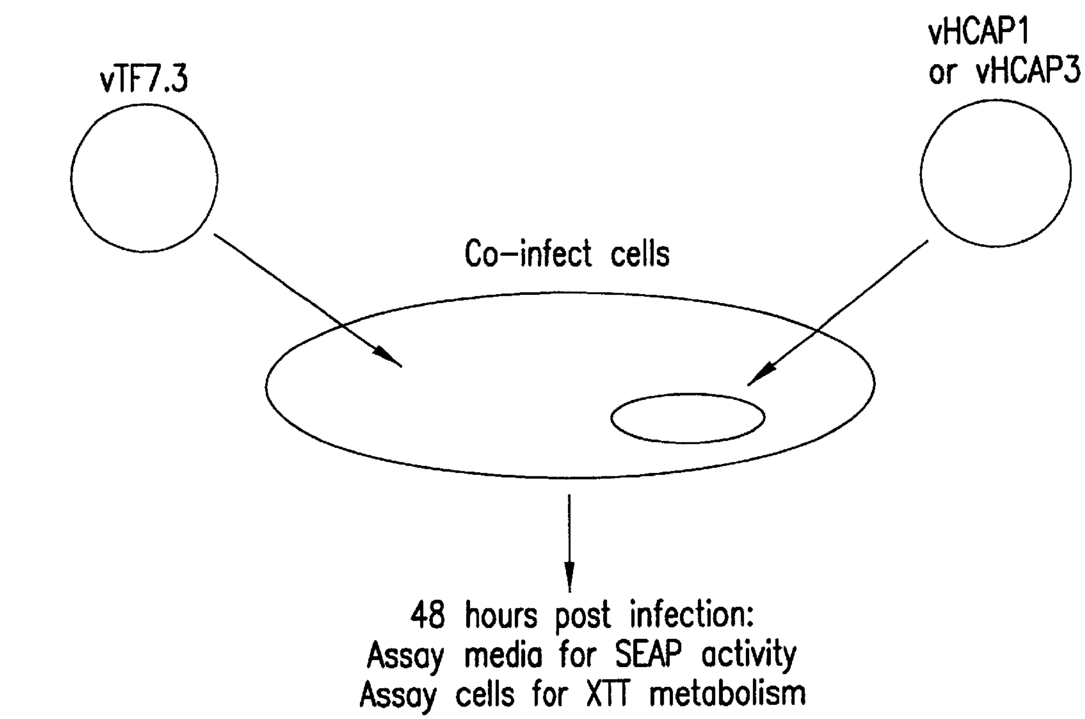
FIG. 3 illustrates schematically the DI/DR Assay.
Figure 3:
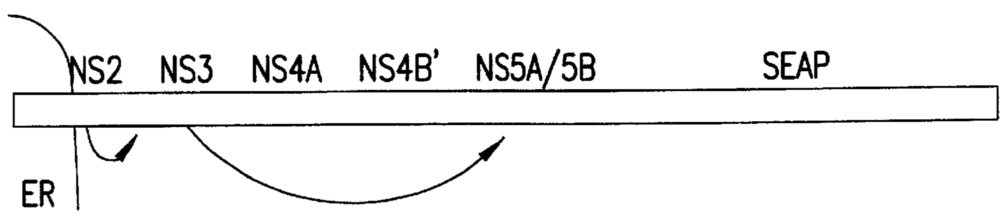
Figure 3:
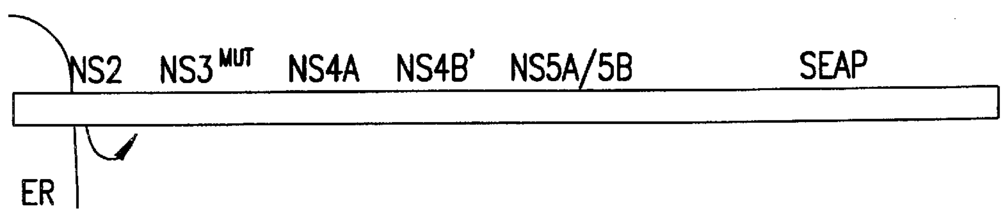

A preferred embodiment involves the co-infection of BHK (ATCC No. CCL-10) or CV1 cells (a COS1 derived line ATCC No. CCL-70) cells with both vHCAP1 and vTF7.3 (ATCC No, VR-2153), with CV1 being more preferred. The latter virus is necessary since the Hep C/SEAP gene remains under control of the T7 RNA polymerase promoter in the vHCAP recombinant viruses. Currently both embodiments which are termed the Hep C/SEAP transfection/infection assay, and the dual recombinant vaccinia virus assay (DI/DR assay) respectively, are useful for HCV protease candidate compound evaluation (FIG. 3).

EXAMPLE 1

Protocol for vTF7.3 Infection/HCV/SEAP Plasmid Transfection Experiment

Day 1

Flat-bottom 96 well plates were seeded with BHK cells at a density of $1\times10^4$ cells/well (equivalent to about 85% confluence) after 24 hours. In general, one 96 well plate was used for investigation of each compound of interest (protease inhibitor), plus an additional plate at the same cell density is used where two rows are designated for each compound of interest at increasing concentrations for investigating the cytotoxicity of the compounds themselves in cells alone. Cytotoxicity was determined by XTT assay (Sigma 4626).

Day 2

The established monolayer was transfected with either pHCAP1, pHCAP3, pHCAP4, or pTM3 plasmids at a concentration of 0.4 μg/well as part of a DNA Lipofectamine (Gibco BRL) transfection mixture. Infections of the established monolayer with vTF7.3 preceded the transfection step. A working stock of vTF7.3 was diluted to a multiplicity of infection (MOI) of 10 with Optimem. The media was aspirated from the wells (2B-10G) 2 rows at a time. A 50 μL aliquot of vTF7.3 inoculum was added per well and gently shaken every 10 minutes. 30 minutes after inoculum addition, the transfection mixes were made by adding 1 mL of Optimem in 3 mL polystyrene tubes. To the media, 48 μg of plasmid DNA was then added to the tubes and mixed, followed by 144 μL of Lipofectamine™, and then the mixture was incubated (R.T.) for 30 minutes. After incubation, 11 mL of Optimem were added to each of the tubes and gently mixed. The vTF7.3 inoculum was aspirated from the wells and 0.1 mL of transfection mix was added to each well and incubated at 34° C. for 4 hours. Compounds/drugs of interest for testing protease inhibition were prepared as stock solutions of 40 mM in 100% DMSO. For assay use, the compounds were diluted to 640 μM (2×) in Optimem with 4% FBS. The compound dilutions were set up in an unused 96 well plate by adding 100 μL Optimem with 4% FBS to wells 4–10 and 150 μL of compound dilutions to all wells in column 3. A serial dilution of the compounds was then performed by transferring 46 μL from well to well across the plate. The transfection mixture was then aspirated from the cells. Then 75 μL of Optimem with 4% FBS was added to the transfected monolayers. Add 75 μL of the 2×compound dilutions to the transfected monolayers and incubated at 34° C. for 48 hours. The cells were checked microscopically at 24 hours and media is collected at 48 hours for measurement of SEAP activity.

SEAP Activity Measurement

After 48 hours, SEAP activity was measured by first transferring 100 μl of media from each well of the 96 well assay plate to a new sterile 96 well plate. Plate(s) were sealed and heated in a heating block at 65 C. for 30 minutes. After 30 minutes, plate(s) were removed and cooled to room temperature. For each heat treated plate, we transferred 50 μl of heat treated media to a Dynex (Dynex 7416) 96 well plate. To each well was added 50 μl of Tropix assay buffer and incubated at room temperature for 5 minutes, followed by an addition to each well of 50 μl of Tropix reaction buffer/CSPD substrate (Tropix), each was mixed, and incubated for an additional 90 minutes at room temperature. Chemiluminescence was read in the Victor multilabel counter from Wallac, Inc. (model number 1420) as one second counts and data is reported as luminescent units/second.

For Examples 1 and 2

XTT Cytotoxicity Assay

XTT (Sigma 4626) was dissolved in phosphate buffered saline (PBS) to a final concentration of 1 mg/mL. 5 mL was prepared per plate. To this solution was added 5 mM PMS (n-methyldibenzopyrazine methyl sulfate salt) (Sigma P9625) to a final concentration of 20 μM. 50 μL of the XTT solution was added per well to the plate set up for cytotoxicity. The plates were incubated at 37 C. in a 5% CO2 incubator for about 3.5 hours and then the color change was quantitated by reading absorbance in a Vmax plate reader (Molecular Devices) at 450 nm/650 nm. Values were corrected by subtracting media-only background and presented as %viable with the untreated cell control representing 100%.

EXAMPLE 2

Representative Experiment and Resulting Data Using Protocol of Example 1

Compounds X, Y, and Z were evaluated in the Vaccinia Virus Infection/Plasmid Transfection assay as outlined in Example 1. BHK cells were seeded into 96 well plates at a density of $1\times10^4$ cells/well and grown overnight to approximately 85% confluency. The SEAP activity was monitored 48 hours post drug addition in cells transfected with either pHCAP1, pHCAP4, pTM3, or no DNA. Concurrently, Compounds X, Y, and Z were evaluated for cell cytotoxicity in a separate dose response assay using XTT to measure cell viability.

For each compound, cells were infected with vTF7.3 followed by the plasmid transfection step. The arrangement of the cells transfected with one of the three plasmids are illustrated in FIG. 10.

Figure 4A:
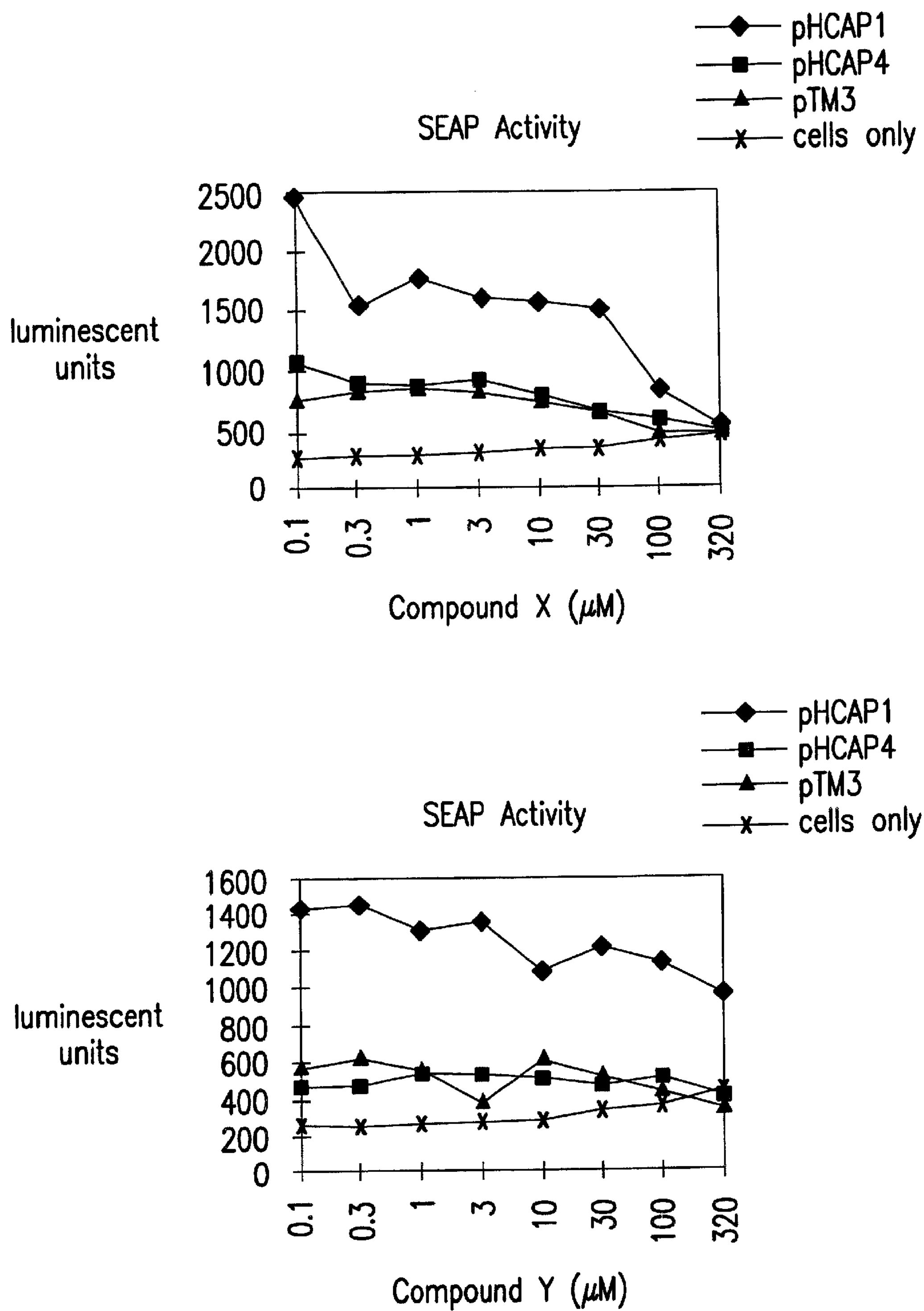
FIGS. 4A and 4B shows the SEAP activity dose response curve for a representative plasmid/virus assay.
Figure 4B:
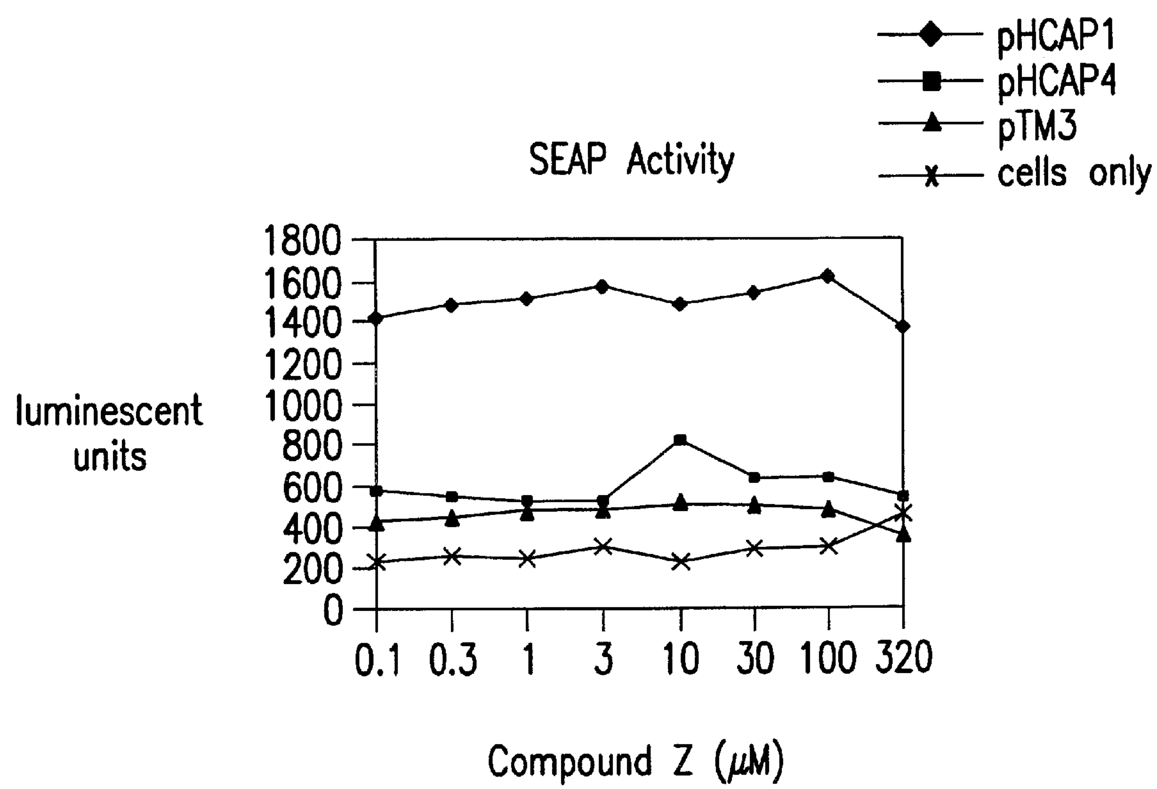

Results for Compounds X, Y, and Z are shown in FIGS. 4A and 4B and Table 1 below. In the three graphs, the amount of SEAP activity detected in cells transfected with the pHCAP1 plasmid ranges from 2 to 7-fold above the amount of SEAP detected in cells transfected with the control plasmids, pHCAP4 and pTM3, or cells only. The $EC_{50}$ (μM) value represents the concentration of drug at which a 50% reduction in SEAP activity is observed relative to the amount of SEAP activity detected in the absence of drug. The $CC_{50}$ (μM) value represents the concentration of drug at which a 50% reduction in cell viability is observed relative to cells in the absence of drug. The ratio of $EC_{50}/CC_{50}$ yields the therapeutic index (TI) which, by convention, should be greater or equal to 10 in order for a compound to be considered as demonstrating antiviral activity.

TABLE 1

| Compound | $EC_{50}$ (μM) | $CC_{50}$ (μM) | Solubility (μM) | TI |
|---|---|---|---|---|
| X | 45 | 178 | =100 | 4 |
| Y | >320 | 112 | =100 | — |
| Z | >320 | 112 | =100 | — |

Within the compound dose range that was examined, only an $EC_{50}$ value for Compound X was obtained. However, since the TI value for Compound X was below 10, it was concluded that Compound X does not represent a candidate inhibitor of NS3 protease activity. Compounds Y and Z did not demonstrate any efficacy in this system and, therefore, are not considered potential candidates (FIGS. 4A and 4B).

For Examples 3 and 4

XTT Cytotoxicity Assay

XTT (Sigma 4626) was dissolved in phosphate buffered saline (PBS) to a final concentration of 1 mg/mL. 5 mL were prepared per plate. To this solution was added 5 mM PMS (n-methyldibenzopyrazine methyl sulfate salt) (Sigma P9625) to a final concentration of 20 μM. This XTT substrate solution was diluted with an equal volume of MEM media containing 4% FBS(V/V). A 100 μL/well of this final solution was added to the original plate which still contains the cell monolayer and about 50 μL incubation media. The plates were Incubated at 37 C. in a 5% CO2 incubator for about 3.5 hours and then the color change was quantitated by reading absorbance in a Vmax plate reader (Molecular Devices) at 450 nm/650 nm. Values were corrected by subtracting media-only background and presented as %viable with the untreated cell control representing 100%.

EXAMPLE 3

Protocol for Dual Infection/Dose Response (DI/DR) Assay

Day 1

Figure 5:
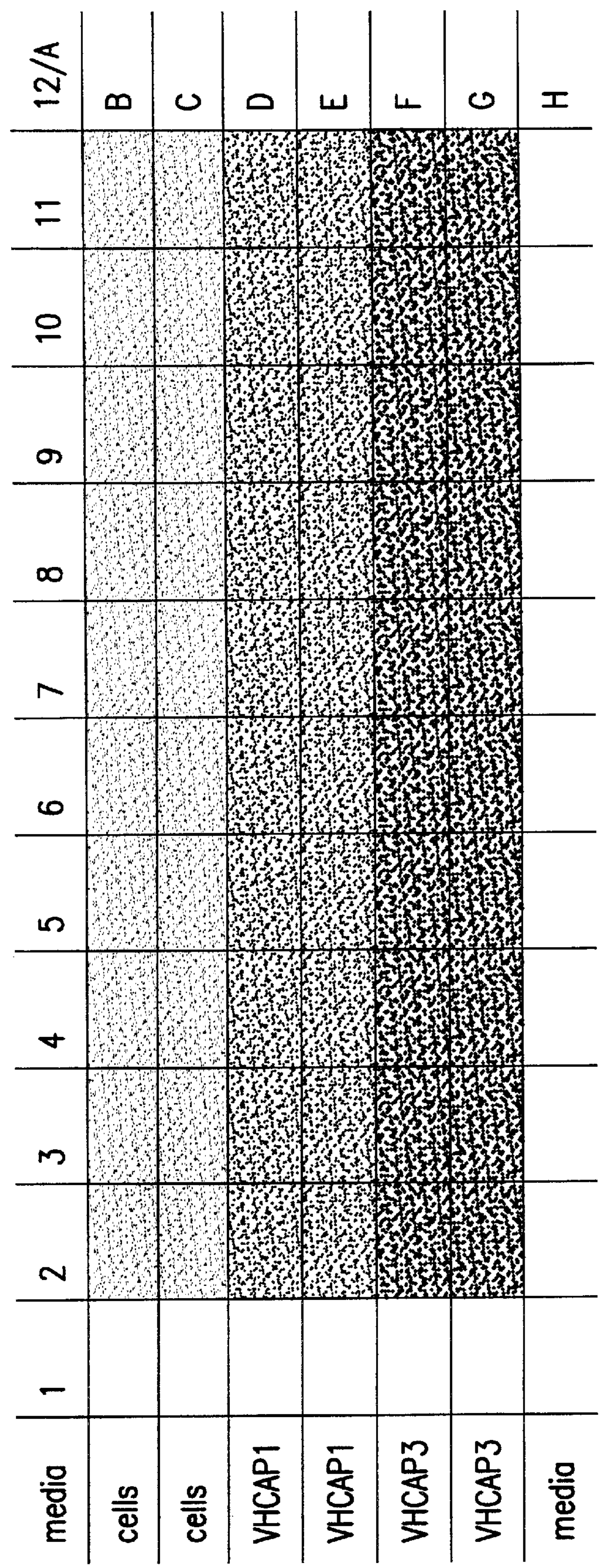
FIG. 5 shows an experimental 96 well plate diagram for the SEAP protocol on Day 1 in Example 3.
Figure 6:
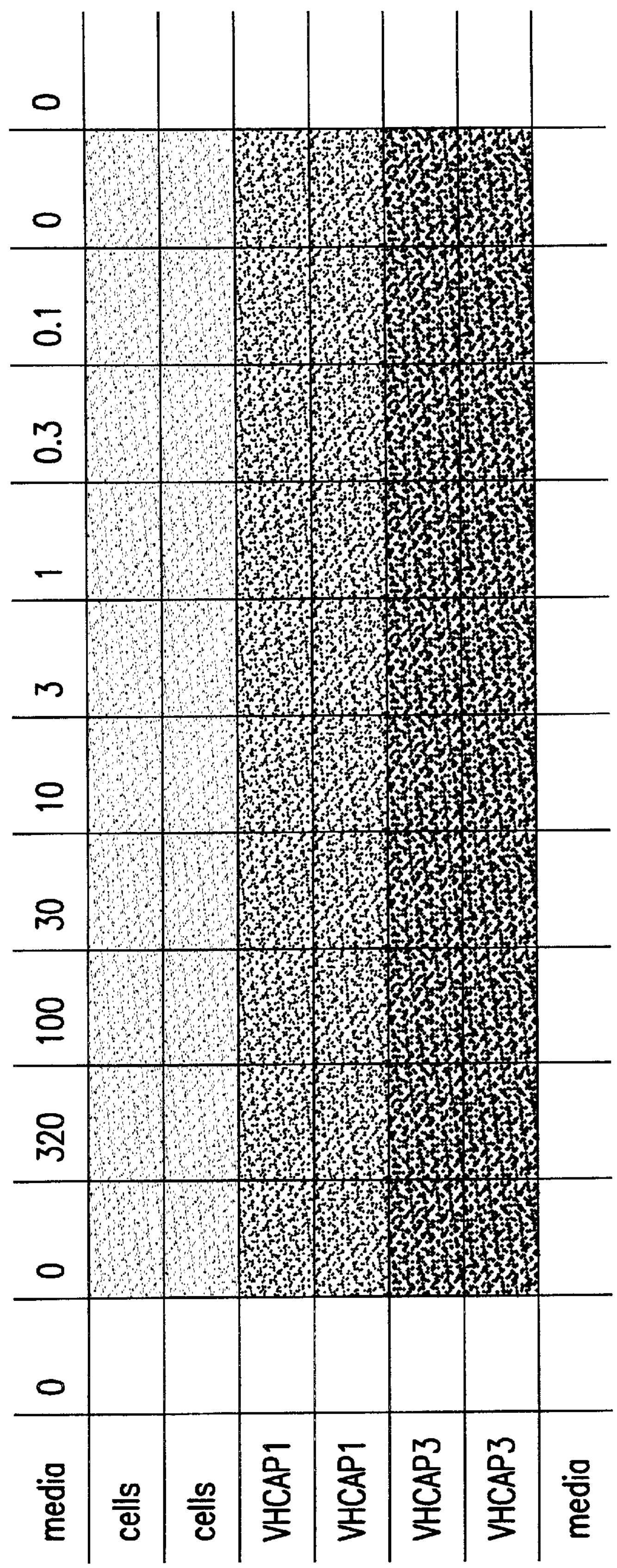
FIG. 6 shows an experimental 96 well plate diagram for the SEAP protocol on Day 2 in Example 3.

Flat-bottom 96-well plates were seeded with CV1 cells at a density of $1\times10^5$ cells per well in MEM media containing 10% FBS with no Phenol Red. The plate was set up as shown in FIG. 5. Media only was placed in all the wells on the edge of the plate and only one compound is evaluated per plate (FIG. 5).

Day 2

Cells were infected with recombinant vaccinia viruses as follows. There should be about $1.5\times10^5$ cells per well after incubation for 24 hours. For every plate needed (a buffer/CPSD substrate was added and mixed. The plate was incubated for 90 minutes at room temperature. The chemiluminescence was then read using a Victor multi-label counter. The XTT assay for measuring cytotoxicity was also performed on Day 4 as described.

EXAMPLE 4

Representative Experiment and Resulting Data Using Protocol of Example 3

Compounds A–I were evaluated in the DI/DR assay using the standard protocol given in Example 3. The data shown in FIG. 7 and FIG. 8 represent assay results obtained at a 48 hour time point post drug addition.

The $EC_{50}$ μM) value represents the concentration of drug at which a 50% reduction in SEAP activity is observed relative to the amount of SEAP activity detected in the absence of drug. However, this latter value, the amount of SEAP activity that is observed in the absence of drug, is first corrected for assay background prior to the calculation of an $EC_{50}$ value. The correction is made since in the inactive NS3 protease construct, vHCAP3, a background level of SEAP activity is detected (see SEAP Activity graph). This background SEAP activity represents non-NS3 protease mediated SEAP activity and therefore should not be affected by the addition of an NS3 protease inhibitor. It is assumed that a fraction of the SEAP activity that is observed in the active NS3 protease construct, vHCAP1, represents non-NS3 protease mediated SEAP activity. Therefore the amount of SEAP activity detected vHCAP1 is corrected for the fraction that corresponds to non-NS3 protease mediated SEAP activity. The correction is as follows: luminescent units of SEAP activity of vHCAP1−luminescent units of SEAP activity of vHCAP3 =Value N (level of NS3 protease dependent SEAP activity). Accordingly, (vHCAP1/SEAP)−N/2=$EC_{50}$ value.

The $CC_{50}$ (μM) value represents the concentration of drug at which a 50% reduction in cell viability is observed relative to cells in the absence of drug. The ratio of $EC_{50}/CC_{50}$ yields the therapeutic index (TI) which, by convention, should be greater or equal to 10 in order for a compound to be considered as demonstrating antiviral activity.

Figure 7:
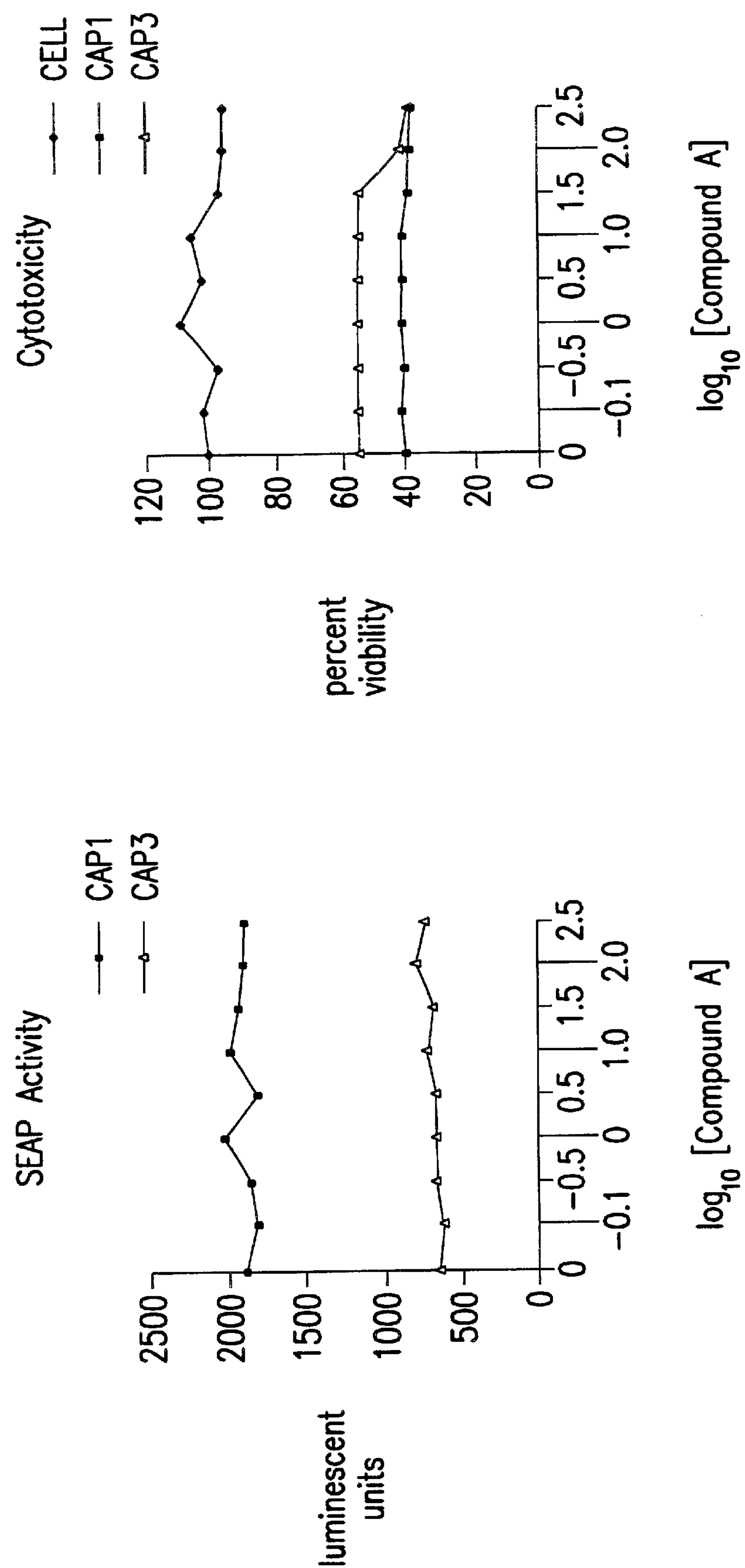
FIG. 7 shows SEAP activity and Cytotoxicity data for Example 4.
Figure 9:
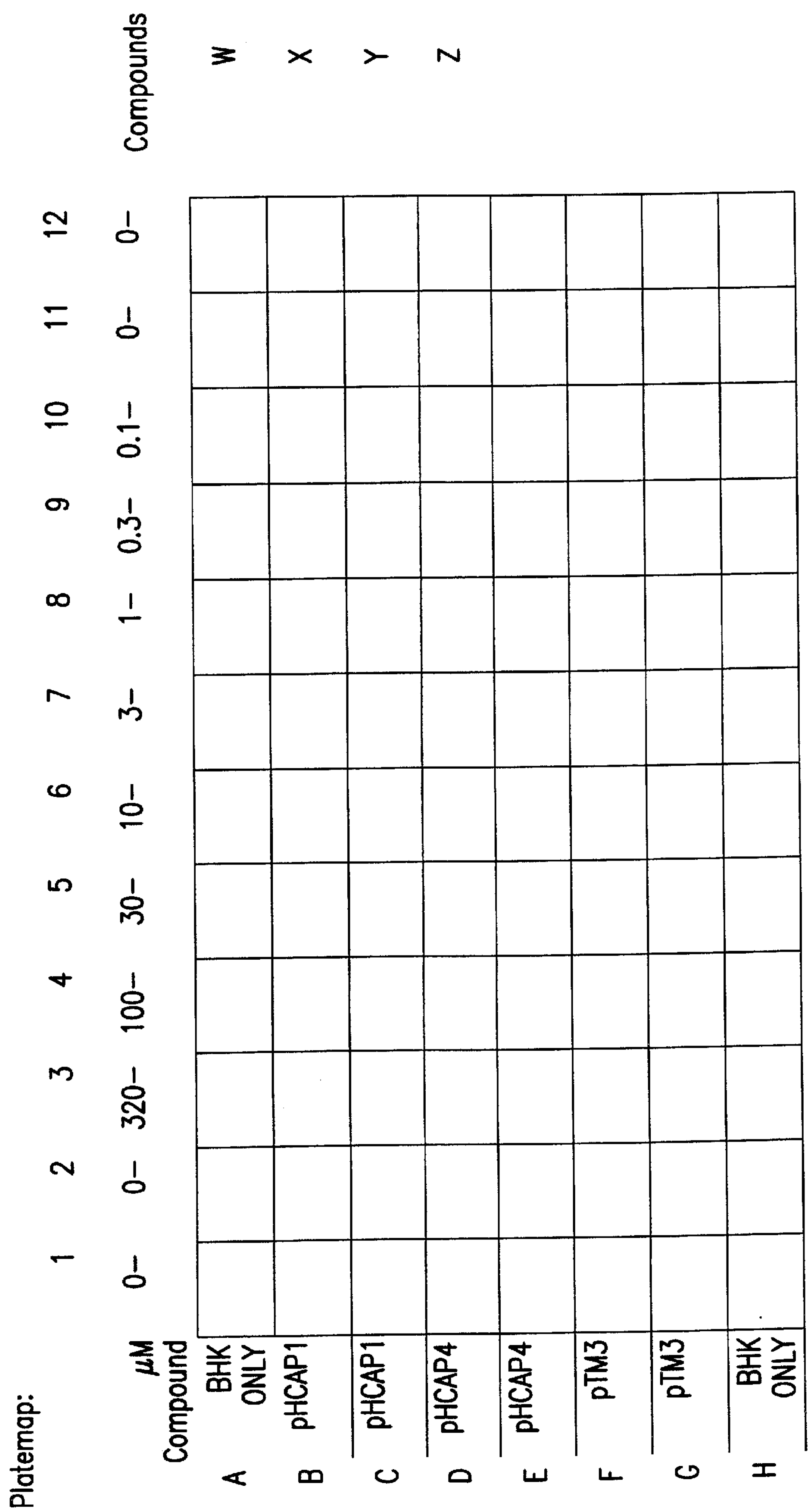
FIG. 9 illustrates the experimental plate set-up for Example 2.

In FIG. 7, increasing concentrations of Compound A were observed to have no affect on SEAP activity. In the cell cytotoxicity component of the assay, it was observed that increasing concentrations of Compound A did not result in a reduction of cell viability of cells alone or cells infected with either vHCAP1/vTF7.3 or vHCAP3/vTF7.3. The results obtained with Compounds B–I (FIG. 8) demonstrate a range of observed cytotoxicities from 15 μM to >320 μM which is the upper limit of drug concentrations tested in the DI/DR assay although it is theoretically possible to test drug concentrations above 320 μM. The $EC_{50}$ values that were observed for Compounds B–I ranged from 18 μM to >320 μM, however, the TI values were under 10. Thus Compounds A–I do not represent potential inhibitors of NS3 protease activity.

We claim:

1. An isolated DNA molecule comprising a recombinant plasmid which comprises a Hepatitis C virus/secreted alkaline phosphatase (SEAP) gene construct operably linked to a promoter, said promoter being compatible with an RNA polymerase, wherein upon co-transfection with a recombinant viral vector, said Hepatitis C virus/SEAP gene construct is under the transcriptional control of said promoter, and wherein said RNA polymerase is acting in trans.

2. The isolated DNA molecule of claim 1, wherein said recombinant plasmid comprises pHCAP1.

3. The isolated DNA molecule of claim 2, wherein said recombinant plasmid comprises SEQ ID No. 1.

4. The isolated DNA molecule of claim 1, wherein said recombinant plasmid comprises pHCAP3.

5. The isolated DNA molecule of claim 4, wherein said recombinant plasmid comprises SEQ ID No. 8.

6. The isolated DNA molecule of claim 1, wherein said recombinant plasmid comprises pHCAP4.

7. The isolated DNA molecule of claim 6, wherein said recombinant plasmid comprises SEQ ID No. 15.

8. An isolated DNA molecule comprising a recombinant viral vector which comprises a Hepatitis C virus/SEAP gene construct operably linked to a promoter, said promoter being compatible with an RNA polymerase, wherein upon co-transfection with a second recombinant viral vector, said Hepatitis C virus/SEAP gene construct is under the transcriptional control of said promoter, and wherein said RNA polymerase is acting in trans.

9. The isolated DNA molecule of claim 8, wherein said recombinant viral vector comprises vHCAP1.

10. The isolated DNA molecule of claim 8, wherein said recombinant viral vector comprises vHCAP3.

11. The isolated DNA molecule of claim 8, wherein said recombinant viral vector comprises vHCAP4.

* * * * *

SEQUENCE LISTING

```
<160> NUMBER OF SEQ ID NOS: 33

<210> SEQ ID NO 1
<211> LENGTH: 13910
<212> TYPE: DNA
<213> ORGANISM: Artificial Sequence
<220> FEATURE:
<223> OTHER INFORMATION: Description of Artificial Sequence: plasmid
      phcap 1
<220> FEATURE:
<221> NAME/KEY: CDS
<222> LOCATION: (497)..(772)
<220> FEATURE:
<221> NAME/KEY: CDS
<222> LOCATION: (1425)..(6500)
<220> FEATURE:
<221> NAME/KEY: CDS
<222> LOCATION: (8579)..(9034)
<220> FEATURE:
<221> NAME/KEY: CDS
<222> LOCATION: (10191)..(10445)
<220> FEATURE:
<221> NAME/KEY: CDS
<222> LOCATION: (11877)..(12734)
<220> FEATURE:
<221> NAME/KEY: misc_feature
<222> LOCATION: (1)..(774)
<223> OTHER INFORMATION: Vaccinia Virus thymidine Kinase gene
      recombination site
<220> FEATURE:
<221> NAME/KEY: promoter
<222> LOCATION: (794)..(816)
<223> OTHER INFORMATION: T7 promoter
<220> FEATURE:
<221> NAME/KEY: misc_feature
<222> LOCATION: (846)..(1424)
<223> OTHER INFORMATION: EMC/Internal Ribosome Entry Site (IRES)
<220> FEATURE:
<221> NAME/KEY: misc_feature
<222> LOCATION: (1426)..(1437)
<223> OTHER INFORMATION: MCS (Multiple Cloning Site)
<220> FEATURE:
<221> NAME/KEY: misc_feature
<222> LOCATION: (1446)..(2318)
<223> OTHER INFORMATION: HCV E2/ NS2 domain
<220> FEATURE:
<221> NAME/KEY: misc_feature
<222> LOCATION: (2319)..(4231)
<223> OTHER INFORMATION: HCV NS3 Domain containing the serine protease
      and helicase enzymes
<220> FEATURE:
<221> NAME/KEY: misc_feature
<222> LOCATION: (4203)..(4260)
<223> OTHER INFORMATION: HCV NS3-NS4A cleavage site
<220> FEATURE:
<221> NAME/KEY: misc_feature
<222> LOCATION: (4375)..(4424)
<223> OTHER INFORMATION: HCV NS4A-4B clevage site
<220> FEATURE:
<221> NAME/KEY: misc_feature
<222> LOCATION: (4233)..(4394)
<223> OTHER INFORMATION: HCV NS4A domain
<220> FEATURE:
<221> NAME/KEY: misc_feature
<222> LOCATION: (4395)..(4919)
<223> OTHER INFORMATION: HCV NS4B Domain
<220> FEATURE:
<221> NAME/KEY: misc_feature
<222> LOCATION: (4920)..(4991)
<223> OTHER INFORMATION: HCV NS5A-NS5B cleavage site
<220> FEATURE:
<221> NAME/KEY: misc_feature
<222> LOCATION: (4992)..(6501)
<223> OTHER INFORMATION: SEAP Protein
<220> FEATURE:
<221> NAME/KEY: misc_feature
```

-continued

```
<222> LOCATION: (7915)..(7945)
<223> OTHER INFORMATION: MCS (Multiple Cloning Site)
<220> FEATURE:
<221> NAME/KEY: terminator
<222> LOCATION: (7938)..(8078)
<223> OTHER INFORMATION: term T7
<220> FEATURE:
<221> NAME/KEY: promoter
<222> LOCATION: (8080)..(8365)
<223> OTHER INFORMATION: Vacinina virus promoter; early/late promoter
<220> FEATURE:
<221> NAME/KEY: misc_feature
<222> LOCATION: (8560)..(11317)
<223> OTHER INFORMATION: E. coli gpt; for selection of recombinants
<220> FEATURE:
<221> NAME/KEY: misc_feature
<222> LOCATION: (11318)..(13909)
<223> OTHER INFORMATION: remaining DNA from 3' end of  Tropix pCMV/SEAP
      plasmid

<400> SEQUENCE: 1

aagcttttgc gatcaataaa tggatcacaa ccagtatctc ttaacgatgt tcttcgcaga     60

tgatgattca ttttttaagt atttggctag tcaagatgat gaatcttcat tatctgatat    120

attgcaaatc actcaatatc tagactttct gttattatta ttgatccaat caaaaaataa    180

attagaagcc gtgggtcatt gttatgaatc tctttcagag gaatacagac aattgacaaa    240

attcacagac tttcaagatt ttaaaaaact gtttaacaag gtccctattg ttacagatgg    300

aagggtcaaa cttaataaag gatatttgtt cgactttgtg attagtttga tgcgattcaa    360

aaaagaatcc tctctagcta ccaccgcaat agatcctgtt agatacatag atcctcgtcg    420

caatatcgca ttttctaacg tgatggatat attaaagtcg aataaagtga acaataatta    480

attctttatt gtcatc atg aac ggc gga cat att cag ttg ata atc ggc ccc    532
                  Met Asn Gly Gly His Ile Gln Leu Ile Ile Gly Pro
                    1               5                  10

atg ttt tca ggt aaa agt aca gaa tta att aga cga gtt aga cgt tat      580
Met Phe Ser Gly Lys Ser Thr Glu Leu Ile Arg Arg Val Arg Arg Tyr
         15                  20                  25

caa ata gct caa tat aaa tgc gtg act ata aaa tat tct aac gat aat      628
Gln Ile Ala Gln Tyr Lys Cys Val Thr Ile Lys Tyr Ser Asn Asp Asn
     30                  35                  40

aga tac gga acg gga cta tgg acg cat gat aag aat aat ttt gaa gca      676
Arg Tyr Gly Thr Gly Leu Trp Thr His Asp Lys Asn Asn Phe Glu Ala
 45                  50                  55                  60

ttg gaa gca act aaa cta tgt gat gtc ttg gaa tca att aca gat ttc      724
Leu Glu Ala Thr Lys Leu Cys Asp Val Leu Glu Ser Ile Thr Asp Phe
                 65                  70                  75

tcc gtg ata ggt atc gat gaa gga cag ttc ttt cca gac att gtt gaa      772
Ser Val Ile Gly Ile Asp Glu Gly Gln Phe Phe Pro Asp Ile Val Glu
             80                  85                  90

ttgatctcga tcccgcgaaa ttaatacgac tcactatagg gagaccacaa cggtttccct    832

ctagcgggat caattccgcc cctctccctc ccccccccct aacgttactg gccgaagccg    892

cttggaataa ggccggtgtg cgtttgtcta tatgttattt tccaccatat tgccgtcttt    952

tggcaatgtg agggcccgga aacctggccc tgtcttcttg acgagcattc ctaggggtct   1012

ttcccctctc gccaaaggaa tgcaaggtct gttgaatgtc gtgaaggaag cagttcctct   1072

ggaagcttct tgaagacaaa caacgtctgt agcgaccctt tgcaggcagc ggaacccccc   1132

acctggcgac aggtgcctct gcggccaaaa gccacgtgta taagatacac ctgcaaaggc   1192

ggcacaaccc cagtgccacg ttgtgagttg gatagttgtg gaaagagtca aatggctctc   1252

ctcaagcgta ttcaacaagg ggctgaagga tgcccagaag gtaccccatt gtatgggatc   1312
```

-continued

```
tgatctgggg cctcggtgca catgctttac atgtgtttag tcgaggttaa aaaacgtcta   1372

ggccccccga accacgggga cgtggttttc ctttgaaaaa cacgataata cc atg gga   1430
                                                          Met Gly

att ccc caa ttc atg gca cgt gtc tgt gcc tgc ttg tgg atg atg ctg     1478
Ile Pro Gln Phe Met Ala Arg Val Cys Ala Cys Leu Trp Met Met Leu
 95                 100                 105                 110

ctg ata gcc cag gcc gag gcc gcc ttg gag aac ctg gtg gtc ctc aat     1526
Leu Ile Ala Gln Ala Glu Ala Ala Leu Glu Asn Leu Val Val Leu Asn
                115                 120                 125

gcg gcg tct gtg gcc ggc gca cat ggc atc ctc tcc ttc ctt gtg ttc     1574
Ala Ala Ser Val Ala Gly Ala His Gly Ile Leu Ser Phe Leu Val Phe
            130                 135                 140

ttc tgt gcc gcc tgg tac atc aaa ggc agg ctg gtc cct ggg gcg gca     1622
Phe Cys Ala Ala Trp Tyr Ile Lys Gly Arg Leu Val Pro Gly Ala Ala
        145                 150                 155

tat gct ctt tat ggc gtg tgg ccg ctg ctc ctg ctc ttg ctg gca tta     1670
Tyr Ala Leu Tyr Gly Val Trp Pro Leu Leu Leu Leu Leu Leu Ala Leu
    160                 165                 170

cca ccg cga gct tac gcc atg gac cgg gag atg gct gca tcg tgc gga     1718
Pro Pro Arg Ala Tyr Ala Met Asp Arg Glu Met Ala Ala Ser Cys Gly
175                 180                 185                 190

ggc gcg gtt ttt gtg ggt ctg gta ctc ctg act ttg tca cca tac tac     1766
Gly Ala Val Phe Val Gly Leu Val Leu Leu Thr Leu Ser Pro Tyr Tyr
                195                 200                 205

aag gtg ttc ctc gct agg ctc ata tgg tgg tta caa tat ttt acc acc     1814
Lys Val Phe Leu Ala Arg Leu Ile Trp Trp Leu Gln Tyr Phe Thr Thr
            210                 215                 220

aga gcc gag gcg cac tta cat gtg tgg atc ccc ccc ctc aac gct cgg     1862
Arg Ala Glu Ala His Leu His Val Trp Ile Pro Pro Leu Asn Ala Arg
        225                 230                 235

gga ggc cgc gat gcc atc atc ctc ctc atg tgc gca gtc cat cca gag     1910
Gly Gly Arg Asp Ala Ile Ile Leu Leu Met Cys Ala Val His Pro Glu
    240                 245                 250

cta atc ttt gac atc acc aaa ctt cta att gcc ata ctc ggt ccg ctc     1958
Leu Ile Phe Asp Ile Thr Lys Leu Leu Ile Ala Ile Leu Gly Pro Leu
255                 260                 265                 270

atg gtg ctc caa gct ggc ata acc aga gtg ccg tac ttc gtg cgc gct     2006
Met Val Leu Gln Ala Gly Ile Thr Arg Val Pro Tyr Phe Val Arg Ala
                275                 280                 285

caa ggg ctc att cat gca tgc atg tta gtg cgg aag gtc gct ggg ggt     2054
Gln Gly Leu Ile His Ala Cys Met Leu Val Arg Lys Val Ala Gly Gly
            290                 295                 300

cat tat gtc caa atg gcc ttc atg aag ctg ggc gcg ctg aca ggc acg     2102
His Tyr Val Gln Met Ala Phe Met Lys Leu Gly Ala Leu Thr Gly Thr
        305                 310                 315

tac att tac aac cat ctt acc ccg cta cgg gat tgg gcc cac gcg ggc     2150
Tyr Ile Tyr Asn His Leu Thr Pro Leu Arg Asp Trp Ala His Ala Gly
    320                 325                 330

cta cga gac ctt gcg gtg gca gtg gag ccc gtc gtc ttc tcc gac atg     2198
Leu Arg Asp Leu Ala Val Ala Val Glu Pro Val Val Phe Ser Asp Met
335                 340                 345                 350

gag acc aag atc atc acc tgg gga gca gac acc gcg gcg tgt ggg gac     2246
Glu Thr Lys Ile Ile Thr Trp Gly Ala Asp Thr Ala Ala Cys Gly Asp
                355                 360                 365

atc atc ttg ggt ctg ccc gtc tcc gcc cga agg gga aag gag ata ctc     2294
Ile Ile Leu Gly Leu Pro Val Ser Ala Arg Arg Gly Lys Glu Ile Leu
            370                 375                 380

ctg ggc ccg gcc gat agt ctt gaa ggg cgg ggg tgg cga ctc ctc gcg     2342
```

-continued

```
Leu Gly Pro Ala Asp Ser Leu Glu Gly Arg Gly Trp Arg Leu Leu Ala
        385                 390                 395

ccc atc acg gcc tac tcc caa cag acg cgg ggc cta ctt ggt tgc atc      2390
Pro Ile Thr Ala Tyr Ser Gln Gln Thr Arg Gly Leu Leu Gly Cys Ile
    400                 405                 410

atc act agc ctt aca ggc cgg gac aag aac cag gtc gag gga gag gtt      2438
Ile Thr Ser Leu Thr Gly Arg Asp Lys Asn Gln Val Glu Gly Glu Val
415                 420                 425                 430

cag gtg gtt tcc acc gca aca caa tcc ttc ctg gcg acc tgc gtc aac      2486
Gln Val Val Ser Thr Ala Thr Gln Ser Phe Leu Ala Thr Cys Val Asn
                435                 440                 445

ggc gtg tgt tgg acc gtt tac cat ggt gct ggc tca aag acc tta gcc      2534
Gly Val Cys Trp Thr Val Tyr His Gly Ala Gly Ser Lys Thr Leu Ala
            450                 455                 460

ggc cca aag ggg cca atc acc cag atg tac act aat gtg gac cag gac      2582
Gly Pro Lys Gly Pro Ile Thr Gln Met Tyr Thr Asn Val Asp Gln Asp
        465                 470                 475

ctc gtc ggc tgg cag gcg ccc ccc ggg gcg cgt tcc ttg aca cca tgc      2630
Leu Val Gly Trp Gln Ala Pro Pro Gly Ala Arg Ser Leu Thr Pro Cys
    480                 485                 490

acc tgt ggc agc tca gac ctt tac ttg gtc acg aga cat gct gac gtc      2678
Thr Cys Gly Ser Ser Asp Leu Tyr Leu Val Thr Arg His Ala Asp Val
495                 500                 505                 510

att ccg gtg cgc cgg cgg ggc gac agt agg ggg agc ctg ctc tcc ccc      2726
Ile Pro Val Arg Arg Arg Gly Asp Ser Arg Gly Ser Leu Leu Ser Pro
                515                 520                 525

agg cct gtc tcc tac ttg aag ggc tct tcg ggt ggt cca ctg ctc tgc      2774
Arg Pro Val Ser Tyr Leu Lys Gly Ser Ser Gly Gly Pro Leu Leu Cys
            530                 535                 540

cct tcg ggg cac gct gtg ggc atc ttc cgg gct gcc gta tgc acc cgg      2822
Pro Ser Gly His Ala Val Gly Ile Phe Arg Ala Ala Val Cys Thr Arg
        545                 550                 555

ggg gtt gcg aag gcg gtg gac ttt gtg ccc gta gag tcc atg gaa act      2870
Gly Val Ala Lys Ala Val Asp Phe Val Pro Val Glu Ser Met Glu Thr
    560                 565                 570

act atg cgg tct ccg gtc ttc acg gac aac tca tcc ccc ccg gcc gta      2918
Thr Met Arg Ser Pro Val Phe Thr Asp Asn Ser Ser Pro Pro Ala Val
575                 580                 585                 590

ccg cag tca ttt caa gtg gcc cac cta cac gct ccc act ggc agc ggc      2966
Pro Gln Ser Phe Gln Val Ala His Leu His Ala Pro Thr Gly Ser Gly
                595                 600                 605

aag agt act aaa gtg ccg gct gca tat gca gcc caa ggg tac aag gtg      3014
Lys Ser Thr Lys Val Pro Ala Ala Tyr Ala Ala Gln Gly Tyr Lys Val
            610                 615                 620

ctc gtc ctc aat ccg tcc gtt gcc gct acc tta ggg ttt ggg gcg tat      3062
Leu Val Leu Asn Pro Ser Val Ala Ala Thr Leu Gly Phe Gly Ala Tyr
        625                 630                 635

atg tct aag gca cac ggt att gac ccc aac atc aga act ggg gta agg      3110
Met Ser Lys Ala His Gly Ile Asp Pro Asn Ile Arg Thr Gly Val Arg
    640                 645                 650

acc att acc aca ggc gcc ccc gtc aca tac tct acc tat ggc aag ttt      3158
Thr Ile Thr Thr Gly Ala Pro Val Thr Tyr Ser Thr Tyr Gly Lys Phe
655                 660                 665                 670

ctt gcc gat ggt ggt tgc tct ggg ggc gct tat gac atc ata ata tgt      3206
Leu Ala Asp Gly Gly Cys Ser Gly Gly Ala Tyr Asp Ile Ile Ile Cys
                675                 680                 685

gat gag tgc cat tca act gac tcg act aca atc ttg ggc atc ggc aca      3254
Asp Glu Cys His Ser Thr Asp Ser Thr Thr Ile Leu Gly Ile Gly Thr
            690                 695                 700
```

-continued

```
gtc ctg gac caa gcg gag acg gct gga gcg cgg ctt gtc gtg ctc gcc     3302
Val Leu Asp Gln Ala Glu Thr Ala Gly Ala Arg Leu Val Val Leu Ala
        705                 710                 715

acc gct acg cct ccg gga tcg gtc acc gtg cca cac cca aac atc gag     3350
Thr Ala Thr Pro Pro Gly Ser Val Thr Val Pro His Pro Asn Ile Glu
    720                 725                 730

gag gtg gcc ctg tct aat act gga gag atc ccc ttc tat ggc aaa gcc     3398
Glu Val Ala Leu Ser Asn Thr Gly Glu Ile Pro Phe Tyr Gly Lys Ala
735                 740                 745                 750

atc ccc att gaa gcc atc agg ggg gga agg cat ctc att ttc tgt cat     3446
Ile Pro Ile Glu Ala Ile Arg Gly Gly Arg His Leu Ile Phe Cys His
                755                 760                 765

tcc aag aag aag tgc gac gag ctc gcc gca aag ctg tca ggc ctc gga     3494
Ser Lys Lys Lys Cys Asp Glu Leu Ala Ala Lys Leu Ser Gly Leu Gly
            770                 775                 780

atc aac gct gtg gcg tat tac cgg ggg ctc gat gtg tcc gtc ata cca     3542
Ile Asn Ala Val Ala Tyr Tyr Arg Gly Leu Asp Val Ser Val Ile Pro
        785                 790                 795

act atc gga gac gtc gtt gtc gtg gca aca gac gct ctg atg acg ggc     3590
Thr Ile Gly Asp Val Val Val Val Ala Thr Asp Ala Leu Met Thr Gly
    800                 805                 810

tat acg ggc gac ttt gac tca gtg atc gac tgt aac aca tgt gtc acc     3638
Tyr Thr Gly Asp Phe Asp Ser Val Ile Asp Cys Asn Thr Cys Val Thr
815                 820                 825                 830

cag aca gtc gac ttc agc ttg gat ccc acc ttc acc att gag acg acg     3686
Gln Thr Val Asp Phe Ser Leu Asp Pro Thr Phe Thr Ile Glu Thr Thr
                835                 840                 845

acc gtg cct caa gac gca gtg tcg cgc tcg cag cgg cgg ggt agg act     3734
Thr Val Pro Gln Asp Ala Val Ser Arg Ser Gln Arg Arg Gly Arg Thr
            850                 855                 860

ggc agg ggt agg aga ggc atc tac agg ttt gtg act ccg gga gaa cgg     3782
Gly Arg Gly Arg Arg Gly Ile Tyr Arg Phe Val Thr Pro Gly Glu Arg
        865                 870                 875

ccc tcg ggc atg ttc gat tcc tcg gtc ctg tgt gag tgc tat gac gcg     3830
Pro Ser Gly Met Phe Asp Ser Ser Val Leu Cys Glu Cys Tyr Asp Ala
    880                 885                 890

ggc tgt gct tgg tac gag ctc acc ccc gcc gag acc tcg gtt agg ttg     3878
Gly Cys Ala Trp Tyr Glu Leu Thr Pro Ala Glu Thr Ser Val Arg Leu
895                 900                 905                 910

cgg gcc tac ctg aac aca cca ggg ttg ccc gtt tgc cag gac cac ctg     3926
Arg Ala Tyr Leu Asn Thr Pro Gly Leu Pro Val Cys Gln Asp His Leu
                915                 920                 925

gag ttc tgg gag agt gtc ttc aca ggc ctc acc cat ata gat gca cac     3974
Glu Phe Trp Glu Ser Val Phe Thr Gly Leu Thr His Ile Asp Ala His
            930                 935                 940

ttc ttg tcc cag acc aag cag gca gga gac aac ttc ccc tac ctg gta     4022
Phe Leu Ser Gln Thr Lys Gln Ala Gly Asp Asn Phe Pro Tyr Leu Val
        945                 950                 955

gca tac caa gcc acg gtg tgc gcc agg gct cag gcc cca cct cca tca     4070
Ala Tyr Gln Ala Thr Val Cys Ala Arg Ala Gln Ala Pro Pro Pro Ser
    960                 965                 970

tgg gat caa atg tgg aag tgt ctc ata cgg ctg aaa cct acg ctg cac     4118
Trp Asp Gln Met Trp Lys Cys Leu Ile Arg Leu Lys Pro Thr Leu His
975                 980                 985                 990

ggg cca aca ccc ttg ctg tac agg ctg gga gcc gtc caa aat gag gtc     4166
Gly Pro Thr Pro Leu Leu Tyr Arg Leu Gly Ala Val Gln Asn Glu Val
                995                 1000                1005

acc ctc acc cac ccc ata acc aaa tac atc atg gca tgc atg tcg gct     4214
Thr Leu Thr His Pro Ile Thr Lys Tyr Ile Met Ala Cys Met Ser Ala
            1010                1015                1020
```

-continued

```
gac ctg gag gtc gtc act agc acc tgg gtg ctg gtg ggc gga gtc ctt     4262
Asp Leu Glu Val Val Thr Ser Thr Trp Val Leu Val Gly Gly Val Leu
       1025                1030                1035

gca gct ctg gcc gcg tat tgc ctg aca aca ggc agt gtg gtc att gtg     4310
Ala Ala Leu Ala Ala Tyr Cys Leu Thr Thr Gly Ser Val Val Ile Val
   1040                1045                1050

ggt agg att atc ttg tcc ggg agg ccg gcc att gtt ccc gac agg gag     4358
Gly Arg Ile Ile Leu Ser Gly Arg Pro Ala Ile Val Pro Asp Arg Glu
1055                1060                1065                1070

ctt ctc tac cag gag ttc gat gaa atg gaa gag tgc gcc tcg cac ctc     4406
Leu Leu Tyr Gln Glu Phe Asp Glu Met Glu Glu Cys Ala Ser His Leu
               1075                1080                1085

cct tac atc gag cag gga atg cag ctc gcc gag caa ttc aag cag aaa     4454
Pro Tyr Ile Glu Gln Gly Met Gln Leu Ala Glu Gln Phe Lys Gln Lys
           1090                1095                1100

gcg ctc ggg tta ctg caa aca gcc acc aaa caa gcg gag gct gct gct     4502
Ala Leu Gly Leu Leu Gln Thr Ala Thr Lys Gln Ala Glu Ala Ala Ala
       1105                1110                1115

ccc gtg gtg gag tcc aag tgg cga gcc ctt gag aca ttc tgg gcg aag     4550
Pro Val Val Glu Ser Lys Trp Arg Ala Leu Glu Thr Phe Trp Ala Lys
   1120                1125                1130

cac atg tgg aat ttc atc agc ggg ata cag tac tta gca ggc tta tcc     4598
His Met Trp Asn Phe Ile Ser Gly Ile Gln Tyr Leu Ala Gly Leu Ser
1135                1140                1145                1150

act ctg cct ggg aac ccc gca ata gca tca ttg atg gca ttc aca gcc     4646
Thr Leu Pro Gly Asn Pro Ala Ile Ala Ser Leu Met Ala Phe Thr Ala
               1155                1160                1165

tct atc acc agc ccg ctc acc acc caa agt acc ctc ctg ttt aac atc     4694
Ser Ile Thr Ser Pro Leu Thr Thr Gln Ser Thr Leu Leu Phe Asn Ile
           1170                1175                1180

ttg ggg ggg tgg gtg gct gcc caa ctc gcc ccc ccc agc gcc gct tcg     4742
Leu Gly Gly Trp Val Ala Ala Gln Leu Ala Pro Pro Ser Ala Ala Ser
       1185                1190                1195

gct ttc gtg ggc gcc ggc atc gcc ggt gcg gct gtt ggc agc ata ggc     4790
Ala Phe Val Gly Ala Gly Ile Ala Gly Ala Ala Val Gly Ser Ile Gly
   1200                1205                1210

ctt ggg aag gtg ctt gtg gac att ctg gcg ggt tat gga gca gga gtg     4838
Leu Gly Lys Val Leu Val Asp Ile Leu Ala Gly Tyr Gly Ala Gly Val
1215                1220                1225                1230

gcc ggc gcg ctc gtg gcc ttt aag gtc atg agc ggc gag atg ccc tcc     4886
Ala Gly Ala Leu Val Ala Phe Lys Val Met Ser Gly Glu Met Pro Ser
               1235                1240                1245

acc gag gac ctg gtc aat cta ctt cct gcc atc ctc gag gaa gct agt     4934
Thr Glu Asp Leu Val Asn Leu Leu Pro Ala Ile Leu Glu Glu Ala Ser
           1250                1255                1260

gag gat gtc gtc tgc tgc tca atg tcc tac aca tgg aca ggc gcc ttg     4982
Glu Asp Val Val Cys Cys Ser Met Ser Tyr Thr Trp Thr Gly Ala Leu
       1265                1270                1275

gag ctg ctg ctg ctg ctg ctg ctg ggc ctg agg cta cag ctc tcc ctg     5030
Glu Leu Leu Leu Leu Leu Leu Leu Gly Leu Arg Leu Gln Leu Ser Leu
   1280                1285                1290

ggc atc atc cca gtt gag gag gag aac ccg gac ttc tgg aac cgc gag     5078
Gly Ile Ile Pro Val Glu Glu Glu Asn Pro Asp Phe Trp Asn Arg Glu
1295                1300                1305                1310

gca gcc gag gcc ctg ggt gcc gcc aag aag ctg cag cct gca cag aca     5126
Ala Ala Glu Ala Leu Gly Ala Ala Lys Lys Leu Gln Pro Ala Gln Thr
               1315                1320                1325

gcc gcc aag aac ctc atc atc ttc ctg ggc gat ggg atg ggg gtg tct     5174
Ala Ala Lys Asn Leu Ile Ile Phe Leu Gly Asp Gly Met Gly Val Ser
```

-continued

```
        1330                1335                1340

acg gtg aca gct gcc agg atc cta aaa ggg cag aag aag gac aaa ctg     5222
Thr Val Thr Ala Ala Arg Ile Leu Lys Gly Gln Lys Lys Asp Lys Leu
    1345                1350                1355

ggg cct gag ata ccc ctg gcc atg gac cgc ttc cca tat gtg gct ctg     5270
Gly Pro Glu Ile Pro Leu Ala Met Asp Arg Phe Pro Tyr Val Ala Leu
  1360                1365                1370

tcc aag aca tac aat gta gac aaa cat gtg cca gac agt gga gcc aca     5318
Ser Lys Thr Tyr Asn Val Asp Lys His Val Pro Asp Ser Gly Ala Thr
1375                1380                1385                1390

gcc acg gcc tac ctg tgc ggg gtc aag ggc aac ttc cag acc att ggc     5366
Ala Thr Ala Tyr Leu Cys Gly Val Lys Gly Asn Phe Gln Thr Ile Gly
            1395                1400                1405

ttg agt gca gcc gcc cgc ttt aac cag tgc aac acg aca cgc ggc aac     5414
Leu Ser Ala Ala Ala Arg Phe Asn Gln Cys Asn Thr Thr Arg Gly Asn
        1410                1415                1420

gag gtc atc tcc gtg atg aat cgg gcc aag aaa gca ggg aag tca gtg     5462
Glu Val Ile Ser Val Met Asn Arg Ala Lys Lys Ala Gly Lys Ser Val
    1425                1430                1435

gga gtg gta acc acc aca cga gtg cag cac gcc tcg cca gcc ggc acc     5510
Gly Val Val Thr Thr Thr Arg Val Gln His Ala Ser Pro Ala Gly Thr
  1440                1445                1450

tac gcc cac acg gtg aac cgc aac tgg tac tcg gac gcc gac gtg cct     5558
Tyr Ala His Thr Val Asn Arg Asn Trp Tyr Ser Asp Ala Asp Val Pro
1455                1460                1465                1470

gcc tcg gcc cgc cag gag ggg tgc cag gac atc gct acg cag ctc atc     5606
Ala Ser Ala Arg Gln Glu Gly Cys Gln Asp Ile Ala Thr Gln Leu Ile
            1475                1480                1485

tcc aac atg gac att gac gtg atc cta ggt gga ggc cga aag tac atg     5654
Ser Asn Met Asp Ile Asp Val Ile Leu Gly Gly Gly Arg Lys Tyr Met
        1490                1495                1500

ttt ccc atg gga acc cca gac cct gag tac cca gat gac tac agc caa     5702
Phe Pro Met Gly Thr Pro Asp Pro Glu Tyr Pro Asp Asp Tyr Ser Gln
    1505                1510                1515

ggt ggg acc agg ctg gac ggg aag aat ctg gtg cag gaa tgg ctg gcg     5750
Gly Gly Thr Arg Leu Asp Gly Lys Asn Leu Val Gln Glu Trp Leu Ala
  1520                1525                1530

aag cgc cag ggt gcc cgg tat gtg tgg aac cgc act gag ctg atg cag     5798
Lys Arg Gln Gly Ala Arg Tyr Val Trp Asn Arg Thr Glu Leu Met Gln
1535                1540                1545                1550

gct tcc ctg gac ccg tct gtg acc cat ctc atg ggt ctc ttt gag cct     5846
Ala Ser Leu Asp Pro Ser Val Thr His Leu Met Gly Leu Phe Glu Pro
            1555                1560                1565

gga gac atg aaa tac gag atc cac cga gac tcc aca ctg gac ccc tcc     5894
Gly Asp Met Lys Tyr Glu Ile His Arg Asp Ser Thr Leu Asp Pro Ser
        1570                1575                1580

ctg atg gag atg aca gag gct gcc ctg cgc ctg ctg agc agg aac ccc     5942
Leu Met Glu Met Thr Glu Ala Ala Leu Arg Leu Leu Ser Arg Asn Pro
    1585                1590                1595

cgc ggc ttc ttc ctc ttc gtg gag ggt ggt cgc atc gac cat ggt cat     5990
Arg Gly Phe Phe Leu Phe Val Glu Gly Gly Arg Ile Asp His Gly His
  1600                1605                1610

cat gaa agc agg gct tac cgg gca ctg act gag acg atc atg ttc gac     6038
His Glu Ser Arg Ala Tyr Arg Ala Leu Thr Glu Thr Ile Met Phe Asp
1615                1620                1625                1630

gac gcc att gag agg gcg ggc cag ctc acc agc gag gag gac acg ctg     6086
Asp Ala Ile Glu Arg Ala Gly Gln Leu Thr Ser Glu Glu Asp Thr Leu
            1635                1640                1645

agc ctc gtc act gcc gac cac tcc cac gtc ttc tcc ttc gga ggc tac     6134
```

-continued

```
Ser Leu Val Thr Ala Asp His Ser His Val Phe Ser Phe Gly Gly Tyr
          1650                1655                1660

ccc ctg cga ggg agc tgc atc ttc ggg ctg gcc cct ggc aag gcc cgg     6182
Pro Leu Arg Gly Ser Cys Ile Phe Gly Leu Ala Pro Gly Lys Ala Arg
       1665                1670                1675

gac agg aag gcc tac acg gtc ctc cta tac gga aac ggt cca ggc tat     6230
Asp Arg Lys Ala Tyr Thr Val Leu Leu Tyr Gly Asn Gly Pro Gly Tyr
   1680                1685                1690

gtg ctc aag gac ggc gcc cgg ccg gat gtt acc gag agc gag agc ggg     6278
Val Leu Lys Asp Gly Ala Arg Pro Asp Val Thr Glu Ser Glu Ser Gly
1695                1700                1705                1710

agc ccc gag tat cgg cag cag tca gca gtg ccc ctg gac gaa gag acc     6326
Ser Pro Glu Tyr Arg Gln Gln Ser Ala Val Pro Leu Asp Glu Glu Thr
              1715                1720                1725

cac gca ggc gag gac gtg gcg gtg ttc gcg cgc ggc ccg cag gcg cac     6374
His Ala Gly Glu Asp Val Ala Val Phe Ala Arg Gly Pro Gln Ala His
          1730                1735                1740

ctg gtt cac ggc gtg cag gag cag acc ttc ata gcg cac gtc atg gcc     6422
Leu Val His Gly Val Gln Glu Gln Thr Phe Ile Ala His Val Met Ala
       1745                1750                1755

ttc gcc gcc tgc ctg gag ccc tac acc gcc tgc gac ctg gcg ccc ccc     6470
Phe Ala Ala Cys Leu Glu Pro Tyr Thr Ala Cys Asp Leu Ala Pro Pro
   1760                1765                1770

gcc ggc acc acc gac gcc gcg cac ccg ggt taacccgtgg tccccgcgtt       6520
Ala Gly Thr Thr Asp Ala Ala His Pro Gly
1775                1780

gcttcctctg ctggccggga catcaggtgg cccccgctga attggaatcg atattgttac   6580

aacaccccaa catcttcgac gcgggcgtgg caggtcttcc cgacgatgac gccggtgaac   6640

ttcccgccgc cgttgttgtt ttggagcacg gaaagacgat gacggaaaaa gagatcgtgg   6700

attacgtcgc cagtcaagta acaaccgcga aaaagttgcg cggaggagtt gtgtttgtgg   6760

acgaagtacc gaaaggtctt accggaaaac tcgacgcaag aaaaatcaga gagatcctca   6820

taaaggccaa gaagggcgga aagtccaaat tgtaaaatgt aactgtattc agcgatgacg   6880

aaattcttag ctattgtaat actgcgatga gtggcagggc ggggcgtaat ttttttaagg   6940

cagttattgg tgcccttaaa cgcctggtgc tacgcctgaa taagtgataa taagcggatg   7000

aatggcagaa attcgccgga tctttgtgaa ggaaccttac ttctgtggtg tgacataatt   7060

ggacaaacta cctacagaga tttaaagctc taaggtaaat ataaaatttt taagtgtata   7120

atgtgttaaa ctactgattc taattgtttg tgtattttag attccaacct atggaactga   7180

tgaatgggag cagtggtgga atgcctttaa tgaggaaaac ctgttttgct cagaagaaat   7240

gccatctagt gatgatgagg ctactgctga ctctcaacat tctactcctc caaaaaagaa   7300

gagaaaggta gaagacccca aggactttcc ttcagaattg ctaagttttt tgagtcatgc   7360

tgtgtttagt aatagaactc ttgcttgctt tgctatttac accacaaagg aaaaagctgc   7420

actgctatac aagaaaatta tggaaaaata ttctgtaacc tttataagta ggcataacag   7480

ttataatcat aacatactgt tttttcttac tccacacagg catagagtgt ctgctattaa   7540

taactatgct caaaaattgt gtacctttag ctttttaatt tgtaaagggg ttaataagga   7600

atatttgatg tatagtgcct tgactagaga tcataatcag ccataccaca tttgtagagg   7660

ttttacttgc tttaaaaaac ctcccacacc tcccctgaa cctgaaacat aaaatgaatg    7720

caattgttgt tgttaacttg tttattgcag cttataatgg ttacaaataa agcaatagca   7780

tcacaaattt cacaaataaa gcattttttt cactgcattc tagttgtggt ttgtccaaac   7840
```

-continued

```
tcatcaatgt atcttatcat gtctggatcc tctagagtcg acctgcaggc atgcaagctt   7900

ctcgagagta cttctagtgg atccctgcag ctcgagaggc ctaattaatt aagtcgacga   7960

tccggctgct aacaaagccc gaaaggaagc tgagttggct gctgccaccg ctgagcaata   8020

actagcataa ccccttgggg cctctaaacg ggtcttgagg ggttttttgc tgaaaggagg   8080

aactatatcc ggagttaact cgacatatac tatatagtaa taccaatact caagactacg   8140

aaactgatac aatctcttat catgtgggta atgttctcga tgtcgaatag ccatatgccg   8200

gtagttgcga tatacataaa ctgatcacta attccaaacc cacccgcttt ttatagtaag   8260

tttttcaccc ataaataata aatacaataa ttaatttctc gtaaaagtag aaaatatatt   8320

ctaatttatt gcacggtaag gaagtagaat cataaagaac agtgacggat cgatccccca   8380

agcttggaca caagacaggc ttgcgagata tgtttgagaa taccacttta tcccgcgtca   8440

gggagaggca gtgcgtaaaa agacgcggac tcatgtgaaa tactggtttt tagtgcgcca   8500

gatctctata atctcgcgca acctattttc ccctcgaaca ctttttaagc cgtagataaa   8560

caggctggga cacttcac atg agc gaa aaa tac atc gtc acc tgg gac atg   8611
                    Met Ser Glu Lys Tyr Ile Val Thr Trp Asp Met
                   1785                1790                1795

ttg cag atc cat gca cgt aaa ctc gca agc cga ctg atg cct tct gaa   8659
Leu Gln Ile His Ala Arg Lys Leu Ala Ser Arg Leu Met Pro Ser Glu
               1800                1805                1810

caa tgg aaa ggc att att gcc gta agc cgt ggc ggt ctg gta ccg ggt   8707
Gln Trp Lys Gly Ile Ile Ala Val Ser Arg Gly Gly Leu Val Pro Gly
           1815                1820                1825

gcg tta ctg gcg cgt gaa ctg ggt att cgt cat gtc gat acc gtt tgt   8755
Ala Leu Leu Ala Arg Glu Leu Gly Ile Arg His Val Asp Thr Val Cys
       1830                1835                1840

att tcc agc tac gat cac gac aac cag cgc gag ctt aaa gtg ctg aaa   8803
Ile Ser Ser Tyr Asp His Asp Asn Gln Arg Glu Leu Lys Val Leu Lys
   1845                1850                1855

cgc gca gaa ggc gat ggc gaa ggc ttc atc gtt att gat gac ctg gtg   8851
Arg Ala Glu Gly Asp Gly Glu Gly Phe Ile Val Ile Asp Asp Leu Val
1860                1865                1870                1875

gat acc ggt ggt act gcg gtt gcg att cgt gaa atg tat cca aaa gcg   8899
Asp Thr Gly Gly Thr Ala Val Ala Ile Arg Glu Met Tyr Pro Lys Ala
               1880                1885                1890

cac ttt gtc acc atc ttc gca aaa ccg gct ggt cgt ccg ctg gtt gat   8947
His Phe Val Thr Ile Phe Ala Lys Pro Ala Gly Arg Pro Leu Val Asp
           1895                1900                1905

gac tat gtt gtt gat atc ccg caa gat acc tgg att gaa cag ccg tgg   8995
Asp Tyr Val Val Asp Ile Pro Gln Asp Thr Trp Ile Glu Gln Pro Trp
       1910                1915                1920

gat atg ggc gtc gta ttc gtc ccg cca atc tcc ggt cgc taatcttttc     9044
Asp Met Gly Val Val Phe Val Pro Pro Ile Ser Gly Arg
   1925                1930                1935

aacgcctggc actgccgggc gttgttcttt ttaacttcag gcgggttaca atagtttcca   9104

gtaagtattc tggaggctgc atccatgaca caggcaaacc tgagcgaaac cctgttcaaa   9164

ccccgcttta aacatcctga aacctcgacg ctagtccgcc gctttaatca cggcgcacaa   9224

ccgcctgtgc agtcggccct tgatggtaaa accatccctc actggtatcg catgattaac   9284

cgtctgatgt ggatctggcg cggcattgac ccacgcgaaa tcctcgacgt ccaggcacgt   9344

attgtgatga gcgatgccga acgtaccgac gatgatttat acgatacggt gattggctac   9404

cgtggcggca actggattta tgagtgggcc ccggatcttt gtgaaggaac cttacttctg   9464

tggtgtgaca taattggaca aactacctac agagatttaa agctctaagg taaatataaa   9524
```

-continued

```
atttttaagt gtataatgtg ttaaactact gattctaatt gtttgtgtat tttagattcc   9584

aacctatgga actgatgaat gggagcagtg gtggaatgcc tttaatgagg aaaacctgtt   9644

ttgctcagaa gaaatgccat ctagtgatga tgaggctact gctgactctc aacattctac   9704

tcctccaaaa aagaagagaa aggtagaaga ccccaaggac tttccttcag aattgctaag   9764

ttttttgagt catgctgtgt ttagtaatag aactcttgct tgctttgcta tttacaccac   9824

aaaggaaaaa gctgcactgc tatacaagaa aattatggaa aaatattctg taacctttat   9884

aagtaggcat aacagttata atcataacat actgtttttt cttactccac acaggcatag   9944

agtgtctgct attaataact atgctcaaaa attgtgtacc tttagctttt taatttgtaa  10004

aggggttaat aaggaatatt tgatgtatag tgccttgact agagatcata atcagccata  10064

ccacatttgt agaggtttta cttgctttaa aaaacctccc acacctcccc ctgaacctga  10124

aacataaaat gaatgcaatt gttgttgtta agcttggggg aattgcatgc tccggatcga  10184

gatcaa ttc tgt gag cgt atg gca aac gaa gga aaa ata gtt ata gta     10232
       Phe Cys Glu Arg Met Ala Asn Glu Gly Lys Ile Val Ile Val
                   1940                1945                1950

gcc gca ctc gat ggg aca ttt caa cgt aaa ccg ttt aat aat att ttg    10280
Ala Ala Leu Asp Gly Thr Phe Gln Arg Lys Pro Phe Asn Asn Ile Leu
               1955                1960                1965

aat ctt att cca tta tct gaa atg gtg gta aaa cta act gct gtg tgt    10328
Asn Leu Ile Pro Leu Ser Glu Met Val Val Lys Leu Thr Ala Val Cys
           1970                1975                1980

atg aaa tgc ttt aag gag gct tcc ttt tct aaa cga ttg ggt gag gaa    10376
Met Lys Cys Phe Lys Glu Ala Ser Phe Ser Lys Arg Leu Gly Glu Glu
       1985                1990                1995

acc gag ata gaa ata ata gga ggt aat gat atg tat caa tcg gtg tgt    10424
Thr Glu Ile Glu Ile Ile Gly Gly Asn Asp Met Tyr Gln Ser Val Cys
   2000                2005                2010

aga aag tgt tac atc gac tca taatattata ttttttatct aaaaaactaa       10475
Arg Lys Cys Tyr Ile Asp Ser
2015                2020

aaataaacat tgattaaatt ttaatataat acttaaaaat ggatgttgtg tcgttagata  10535

aaccgtttat gtattttgag gaaattgata atgagttaga ttacgaacca gaaagtgcaa  10595

atgaggtcgc aaaaaaactg ccgtatcaag gacagttaaa actattacta ggagaattat  10655

tttttcttag taagttacag cgacacggta tattagatgg tgccaccgta gtgtatatag  10715

gatctgctcc cggtacacat atacgttatt tgagagatca tttctataat ttaggagtga  10775

tcatcaaatg gatgctaatt gacggccgcc atcatgatcc tattttaaat ggattgcgtg  10835

atgtgactct agtgactcgg ttcgttgatg aggaatatct acgatccatc aaaaaacaac  10895

tgcatccttc taagattatt ttaatttctg atgtgagatc caaacgagga ggaaatgaac  10955

ctagtacggc ggatttacta agtaattacg ctctacaaaa tgtcatgatt agtattttaa  11015

accccgtggc gtctagtctt aaatggagat gcccgtttcc agatcaatgg atcaaggact  11075

tttatatccc acacggtaat aaaatgttac aacctttgc tccttcatat tcagggccgt   11135

cgttttacaa cgtcgtgact gggaaaaccc tggcgttacc caacttaatc gccttgcagc  11195

acatccccct ttcgccagct ggcgtaatag cgaagaggcc cgcaccgatc gcccttccca  11255

acagttgcgc agcctgaatg gcgaatggcg cgacgcgccc tgtagcggcg cattaagcgc  11315

ggcgggtgtg gtggttacgc gcagcgtgac cgctacactt gccagcgccc tagcgcccgc  11375

tcctttcgct ttcttccctt cctttctcgc cacgttcgcc ggctttcccc gtcaagctct  11435
```

-continued

```
aaatcggggg ctccctttag ggttccgatt tagtgcttta cggcacctcg accccaaaaa  11495

acttgattag ggtgatggtt cacgtagtgg gccatcgccc tgatagacgg tttttcgccc  11555

tttgacgttg gagtccacgt tctttaatag tggactcttg ttccaaactg gaacaacact  11615

caaccctatc tcggtctatt cttttgattt ataagggatt ttgccgattt cggcctattg  11675

gttaaaaaat gagctgattt aacaaaaatt taacgcgaat tttaacaaaa tattaacgtt  11735

tacaatttcc caggtggcac ttttcgggga aatgtgcgcg gaacccctat ttgtttattt  11795

ttctaaatac attcaaatat gtatccgctc atgagacaat aaccctgata aatgcttcaa  11855

taatattgaa aaaggaagag t atg agt att caa cat ttc cgt gtc gcc ctt    11906
                        Met Ser Ile Gln His Phe Arg Val Ala Leu
                                    2025                2030

att ccc ttt ttt gcg gca ttt tgc ctt cct gtt ttt gct cac cca gaa    11954
Ile Pro Phe Phe Ala Ala Phe Cys Leu Pro Val Phe Ala His Pro Glu
            2035                2040                2045

acg ctg gtg aaa gta aaa gat gct gaa gat cag ttg ggt gca cga gtg    12002
Thr Leu Val Lys Val Lys Asp Ala Glu Asp Gln Leu Gly Ala Arg Val
        2050                2055                2060

ggt tac atc gaa ctg gat ctc aac agc ggt aag atc ctt gag agt ttt    12050
Gly Tyr Ile Glu Leu Asp Leu Asn Ser Gly Lys Ile Leu Glu Ser Phe
    2065                2070                2075

cgc ccc gaa gaa cgt ttt cca atg atg agc act ttt aaa gtt ctg cta    12098
Arg Pro Glu Glu Arg Phe Pro Met Met Ser Thr Phe Lys Val Leu Leu
2080                2085                2090                2095

tgt ggc gcg gta tta tcc cgt att gac gcc ggg caa gag caa ctc ggt    12146
Cys Gly Ala Val Leu Ser Arg Ile Asp Ala Gly Gln Glu Gln Leu Gly
                2100                2105                2110

cgc cgc ata cac tat tct cag aat gac ttg gtt gag tac tca cca gtc    12194
Arg Arg Ile His Tyr Ser Gln Asn Asp Leu Val Glu Tyr Ser Pro Val
            2115                2120                2125

aca gaa aag cat ctt acg gat ggc atg aca gta aga gaa tta tgc agt    12242
Thr Glu Lys His Leu Thr Asp Gly Met Thr Val Arg Glu Leu Cys Ser
        2130                2135                2140

gct gcc ata acc atg agt gat aac act gcg gcc aac tta ctt ctg aca    12290
Ala Ala Ile Thr Met Ser Asp Asn Thr Ala Ala Asn Leu Leu Leu Thr
    2145                2150                2155

acg atc gga gga ccg aag gag cta acc gct ttt ttg cac aac atg ggg    12338
Thr Ile Gly Gly Pro Lys Glu Leu Thr Ala Phe Leu His Asn Met Gly
2160                2165                2170                2175

gat cat gta act cgc ctt gat cgt tgg gaa ccg gag ctg aat gaa gcc    12386
Asp His Val Thr Arg Leu Asp Arg Trp Glu Pro Glu Leu Asn Glu Ala
                2180                2185                2190

ata cca aac gac gag cgt gac acc acg atg cct gta gca atg gca aca    12434
Ile Pro Asn Asp Glu Arg Asp Thr Thr Met Pro Val Ala Met Ala Thr
            2195                2200                2205

acg ttg cgc aaa cta tta act ggc gaa cta ctt act cta gct tcc cgg    12482
Thr Leu Arg Lys Leu Leu Thr Gly Glu Leu Leu Thr Leu Ala Ser Arg
        2210                2215                2220

caa caa tta ata gac tgg atg gag gcg gat aaa gtt gca gga cca ctt    12530
Gln Gln Leu Ile Asp Trp Met Glu Ala Asp Lys Val Ala Gly Pro Leu
    2225                2230                2235

ctg cgc tcg gcc ctt ccg gct ggc tgg ttt att gct gat aaa tct gga    12578
Leu Arg Ser Ala Leu Pro Ala Gly Trp Phe Ile Ala Asp Lys Ser Gly
2240                2245                2250                2255

gcc ggt gag cgt ggg tct cgc ggt atc att gca gca ctg ggg cca gat    12626
Ala Gly Glu Arg Gly Ser Arg Gly Ile Ile Ala Ala Leu Gly Pro Asp
                2260                2265                2270

ggt aag ccc tcc cgt atc gta gtt atc tac acg acg ggg agt cag gca    12674
```

-continued

```
Gly Lys Pro Ser Arg Ile Val Val Ile Tyr Thr Thr Gly Ser Gln Ala
           2275                2280                2285

act atg gat gaa cga aat aga cag atc gct gag ata ggt gcc tca ctg    12722
Thr Met Asp Glu Arg Asn Arg Gln Ile Ala Glu Ile Gly Ala Ser Leu
       2290                2295                2300

att aag cat tgg taactgtcag accaagttta ctcatatata ctttagattg       12774
Ile Lys His Trp
   2305

atttaaaact tcatttttaa tttaaaagga tctaggtgaa gatccttttt gataatctca  12834

tgaccaaaat cccttaacgt gagttttcgt tccactgagc gtcagacccc gtagaaaaga  12894

tcaaaggatc ttcttgagat cctttttttc tgcgcgtaat ctgctgcttg caaacaaaaa  12954

aaccaccgct accagcggtg gtttgtttgc cggatcaaga gctaccaact ctttttccga  13014

aggtaactgg cttcagcaga gcgcagatac caaatactgt ccttctagtg tagccgtagt  13074

taggccacca cttcaagaac tctgtagcac cgcctacata cctcgctctg ctaatcctgt  13134

taccagtggc tgctgccagt ggcgataagt cgtgtcttac cgggttggac tcaagacgat  13194

agttaccgga taaggcgcag cggtcgggct gaacgggggg ttcgtgcaca cagcccagct  13254

tggagcgaac gacctacacc gaactgagat acctacagcg tgagctatga gaaagcgcca  13314

cgcttcccga agggagaaag gcggacaggt atccggtaag cggcagggtc ggaacaggag  13374

agcgcacgag ggagcttcca gggggaaacg cctggtatct ttatagtcct gtcgggtttc  13434

gccacctctg acttgagcgt cgatttttgt gatgctcgtc aggggggcgg agcctatgga  13494

aaaacgccag caacgcggcc tttttacggt tcctggcctt ttgctggcct tttgctcaca  13554

tgttctttcc tgcgttatcc cctgattctg tggataaccg tattaccgcc tttgagtgag  13614

ctgataccgc tcgccgcagc cgaacgaccg agcgcagcga gtcagtgagc gaggaagcgg  13674

aagagcgccc aatacgcaaa ccgcctctcc ccgcgcgttg gccgattcat taatgcagct  13734

ggcacgacag gtttcccgac tggaaagcgg gcagtgagcg caacgcaatt aatgtgagtt  13794

agctcactca ttaggcaccc caggctttac actttatgct tccggctcgt atgttgtgtg  13854

gaattgtgag cggataacaa tttcacacag gaaacagcta tgaccatgat tacgcc      13910


<210> SEQ ID NO 2
<211> LENGTH: 2307
<212> TYPE: PRT
<213> ORGANISM: Artificial Sequence
<220> FEATURE:
<223> OTHER INFORMATION: :

<400> SEQUENCE: 2

Met Asn Gly Gly His Ile Gln Leu Ile Ile Gly Pro Met Phe Ser Gly
  1               5                  10                  15

Lys Ser Thr Glu Leu Ile Arg Arg Val Arg Arg Tyr Gln Ile Ala Gln
             20                  25                  30

Tyr Lys Cys Val Thr Ile Lys Tyr Ser Asn Asp Asn Arg Tyr Gly Thr
         35                  40                  45

Gly Leu Trp Thr His Asp Lys Asn Asn Phe Glu Ala Leu Glu Ala Thr
     50                  55                  60

Lys Leu Cys Asp Val Leu Glu Ser Ile Thr Asp Phe Ser Val Ile Gly
 65                  70                  75                  80

Ile Asp Glu Gly Gln Phe Phe Pro Asp Ile Val Glu Met Gly Ile Pro
                 85                  90                  95

Gln Phe Met Ala Arg Val Cys Ala Cys Leu Trp Met Met Leu Leu Ile
            100                 105                 110
```

-continued

```
Ala Gln Ala Glu Ala Ala Leu Glu Asn Leu Val Val Leu Asn Ala Ala
        115                 120                 125

Ser Val Ala Gly Ala His Gly Ile Leu Ser Phe Leu Val Phe Phe Cys
    130                 135                 140

Ala Ala Trp Tyr Ile Lys Gly Arg Leu Val Pro Gly Ala Ala Tyr Ala
145                 150                 155                 160

Leu Tyr Gly Val Trp Pro Leu Leu Leu Leu Leu Leu Ala Leu Pro Pro
                165                 170                 175

Arg Ala Tyr Ala Met Asp Arg Glu Met Ala Ala Ser Cys Gly Gly Ala
            180                 185                 190

Val Phe Val Gly Leu Val Leu Leu Thr Leu Ser Pro Tyr Tyr Lys Val
        195                 200                 205

Phe Leu Ala Arg Leu Ile Trp Trp Leu Gln Tyr Phe Thr Thr Arg Ala
    210                 215                 220

Glu Ala His Leu His Val Trp Ile Pro Pro Leu Asn Ala Arg Gly Gly
225                 230                 235                 240

Arg Asp Ala Ile Ile Leu Leu Met Cys Ala Val His Pro Glu Leu Ile
                245                 250                 255

Phe Asp Ile Thr Lys Leu Leu Ile Ala Ile Leu Gly Pro Leu Met Val
            260                 265                 270

Leu Gln Ala Gly Ile Thr Arg Val Pro Tyr Phe Val Arg Ala Gln Gly
        275                 280                 285

Leu Ile His Ala Cys Met Leu Val Arg Lys Val Ala Gly Gly His Tyr
    290                 295                 300

Val Gln Met Ala Phe Met Lys Leu Gly Ala Leu Thr Gly Thr Tyr Ile
305                 310                 315                 320

Tyr Asn His Leu Thr Pro Leu Arg Asp Trp Ala His Ala Gly Leu Arg
                325                 330                 335

Asp Leu Ala Val Ala Val Glu Pro Val Val Phe Ser Asp Met Glu Thr
            340                 345                 350

Lys Ile Ile Thr Trp Gly Ala Asp Thr Ala Ala Cys Gly Asp Ile Ile
        355                 360                 365

Leu Gly Leu Pro Val Ser Ala Arg Arg Gly Lys Glu Ile Leu Leu Gly
    370                 375                 380

Pro Ala Asp Ser Leu Glu Gly Arg Gly Trp Arg Leu Leu Ala Pro Ile
385                 390                 395                 400

Thr Ala Tyr Ser Gln Gln Thr Arg Gly Leu Leu Gly Cys Ile Ile Thr
                405                 410                 415

Ser Leu Thr Gly Arg Asp Lys Asn Gln Val Glu Gly Glu Val Gln Val
            420                 425                 430

Val Ser Thr Ala Thr Gln Ser Phe Leu Ala Thr Cys Val Asn Gly Val
        435                 440                 445

Cys Trp Thr Val Tyr His Gly Ala Gly Ser Lys Thr Leu Ala Gly Pro
    450                 455                 460

Lys Gly Pro Ile Thr Gln Met Tyr Thr Asn Val Asp Gln Asp Leu Val
465                 470                 475                 480

Gly Trp Gln Ala Pro Pro Gly Ala Arg Ser Leu Thr Pro Cys Thr Cys
                485                 490                 495

Gly Ser Ser Asp Leu Tyr Leu Val Thr Arg His Ala Asp Val Ile Pro
            500                 505                 510

Val Arg Arg Arg Gly Asp Ser Arg Gly Ser Leu Leu Ser Pro Arg Pro
        515                 520                 525
```

-continued

```
Val Ser Tyr Leu Lys Gly Ser Ser Gly Gly Pro Leu Leu Cys Pro Ser
    530                 535                 540

Gly His Ala Val Gly Ile Phe Arg Ala Ala Val Cys Thr Arg Gly Val
545                 550                 555                 560

Ala Lys Ala Val Asp Phe Val Pro Val Glu Ser Met Glu Thr Thr Met
                565                 570                 575

Arg Ser Pro Val Phe Thr Asp Asn Ser Ser Pro Pro Ala Val Pro Gln
            580                 585                 590

Ser Phe Gln Val Ala His Leu His Ala Pro Thr Gly Ser Gly Lys Ser
        595                 600                 605

Thr Lys Val Pro Ala Ala Tyr Ala Ala Gln Gly Tyr Lys Val Leu Val
    610                 615                 620

Leu Asn Pro Ser Val Ala Ala Thr Leu Gly Phe Gly Ala Tyr Met Ser
625                 630                 635                 640

Lys Ala His Gly Ile Asp Pro Asn Ile Arg Thr Gly Val Arg Thr Ile
                645                 650                 655

Thr Thr Gly Ala Pro Val Thr Tyr Ser Thr Tyr Gly Lys Phe Leu Ala
            660                 665                 670

Asp Gly Gly Cys Ser Gly Gly Ala Tyr Asp Ile Ile Ile Cys Asp Glu
        675                 680                 685

Cys His Ser Thr Asp Ser Thr Thr Ile Leu Gly Ile Gly Thr Val Leu
    690                 695                 700

Asp Gln Ala Glu Thr Ala Gly Ala Arg Leu Val Val Leu Ala Thr Ala
705                 710                 715                 720

Thr Pro Pro Gly Ser Val Thr Val Pro His Pro Asn Ile Glu Glu Val
                725                 730                 735

Ala Leu Ser Asn Thr Gly Glu Ile Pro Phe Tyr Gly Lys Ala Ile Pro
            740                 745                 750

Ile Glu Ala Ile Arg Gly Gly Arg His Leu Ile Phe Cys His Ser Lys
        755                 760                 765

Lys Lys Cys Asp Glu Leu Ala Ala Lys Leu Ser Gly Leu Gly Ile Asn
    770                 775                 780

Ala Val Ala Tyr Tyr Arg Gly Leu Asp Val Ser Val Ile Pro Thr Ile
785                 790                 795                 800

Gly Asp Val Val Val Val Ala Thr Asp Ala Leu Met Thr Gly Tyr Thr
                805                 810                 815

Gly Asp Phe Asp Ser Val Ile Asp Cys Asn Thr Cys Val Thr Gln Thr
            820                 825                 830

Val Asp Phe Ser Leu Asp Pro Thr Phe Thr Ile Glu Thr Thr Thr Val
        835                 840                 845

Pro Gln Asp Ala Val Ser Arg Ser Gln Arg Arg Gly Arg Thr Gly Arg
    850                 855                 860

Gly Arg Arg Gly Ile Tyr Arg Phe Val Thr Pro Gly Glu Arg Pro Ser
865                 870                 875                 880

Gly Met Phe Asp Ser Ser Val Leu Cys Glu Cys Tyr Asp Ala Gly Cys
                885                 890                 895

Ala Trp Tyr Glu Leu Thr Pro Ala Glu Thr Ser Val Arg Leu Arg Ala
            900                 905                 910

Tyr Leu Asn Thr Pro Gly Leu Pro Val Cys Gln Asp His Leu Glu Phe
        915                 920                 925

Trp Glu Ser Val Phe Thr Gly Leu Thr His Ile Asp Ala His Phe Leu
    930                 935                 940

Ser Gln Thr Lys Gln Ala Gly Asp Asn Phe Pro Tyr Leu Val Ala Tyr
```

-continued

```
945                 950                 955                 960

Gln Ala Thr Val Cys Ala Arg Ala Gln Ala Pro Pro Pro Ser Trp Asp
                965                 970                 975

Gln Met Trp Lys Cys Leu Ile Arg Leu Lys Pro Thr Leu His Gly Pro
            980                 985                 990

Thr Pro Leu Leu Tyr Arg Leu Gly Ala Val Gln Asn Glu Val Thr Leu
        995                 1000                1005

Thr His Pro Ile Thr Lys Tyr Ile Met Ala Cys Met Ser Ala Asp Leu
   1010                1015                1020

Glu Val Val Thr Ser Thr Trp Val Leu Val Gly Gly Val Leu Ala Ala
1025                1030                1035                1040

Leu Ala Ala Tyr Cys Leu Thr Thr Gly Ser Val Val Ile Val Gly Arg
                1045                1050                1055

Ile Ile Leu Ser Gly Arg Pro Ala Ile Val Pro Asp Arg Glu Leu Leu
            1060                1065                1070

Tyr Gln Glu Phe Asp Glu Met Glu Glu Cys Ala Ser His Leu Pro Tyr
        1075                1080                1085

Ile Glu Gln Gly Met Gln Leu Ala Glu Gln Phe Lys Gln Lys Ala Leu
   1090                1095                1100

Gly Leu Leu Gln Thr Ala Thr Lys Gln Ala Glu Ala Ala Ala Pro Val
1105                1110                1115                1120

Val Glu Ser Lys Trp Arg Ala Leu Glu Thr Phe Trp Ala Lys His Met
                1125                1130                1135

Trp Asn Phe Ile Ser Gly Ile Gln Tyr Leu Ala Gly Leu Ser Thr Leu
            1140                1145                1150

Pro Gly Asn Pro Ala Ile Ala Ser Leu Met Ala Phe Thr Ala Ser Ile
        1155                1160                1165

Thr Ser Pro Leu Thr Thr Gln Ser Thr Leu Leu Phe Asn Ile Leu Gly
   1170                1175                1180

Gly Trp Val Ala Ala Gln Leu Ala Pro Pro Ser Ala Ala Ser Ala Phe
1185                1190                1195                1200

Val Gly Ala Gly Ile Ala Gly Ala Ala Val Gly Ser Ile Gly Leu Gly
                1205                1210                1215

Lys Val Leu Val Asp Ile Leu Ala Gly Tyr Gly Ala Gly Val Ala Gly
            1220                1225                1230

Ala Leu Val Ala Phe Lys Val Met Ser Gly Glu Met Pro Ser Thr Glu
        1235                1240                1245

Asp Leu Val Asn Leu Leu Pro Ala Ile Leu Glu Glu Ala Ser Glu Asp
   1250                1255                1260

Val Val Cys Cys Ser Met Ser Tyr Thr Trp Thr Gly Ala Leu Glu Leu
1265                1270                1275                1280

Leu Leu Leu Leu Leu Leu Gly Leu Arg Leu Gln Leu Ser Leu Gly Ile
                1285                1290                1295

Ile Pro Val Glu Glu Glu Asn Pro Asp Phe Trp Asn Arg Glu Ala Ala
            1300                1305                1310

Glu Ala Leu Gly Ala Ala Lys Lys Leu Gln Pro Ala Gln Thr Ala Ala
        1315                1320                1325

Lys Asn Leu Ile Ile Phe Leu Gly Asp Gly Met Gly Val Ser Thr Val
   1330                1335                1340

Thr Ala Ala Arg Ile Leu Lys Gly Gln Lys Lys Asp Lys Leu Gly Pro
1345                1350                1355                1360

Glu Ile Pro Leu Ala Met Asp Arg Phe Pro Tyr Val Ala Leu Ser Lys
                1365                1370                1375
```

-continued

```
Thr Tyr Asn Val Asp Lys His Val Pro Asp Ser Gly Ala Thr Ala Thr
            1380                1385                1390

Ala Tyr Leu Cys Gly Val Lys Gly Asn Phe Gln Thr Ile Gly Leu Ser
        1395                1400                1405

Ala Ala Ala Arg Phe Asn Gln Cys Asn Thr Thr Arg Gly Asn Glu Val
    1410                1415                1420

Ile Ser Val Met Asn Arg Ala Lys Lys Ala Gly Lys Ser Val Gly Val
1425                1430                1435                1440

Val Thr Thr Thr Arg Val Gln His Ala Ser Pro Ala Gly Thr Tyr Ala
                1445                1450                1455

His Thr Val Asn Arg Asn Trp Tyr Ser Asp Ala Asp Val Pro Ala Ser
            1460                1465                1470

Ala Arg Gln Glu Gly Cys Gln Asp Ile Ala Thr Gln Leu Ile Ser Asn
        1475                1480                1485

Met Asp Ile Asp Val Ile Leu Gly Gly Gly Arg Lys Tyr Met Phe Pro
    1490                1495                1500

Met Gly Thr Pro Asp Pro Glu Tyr Pro Asp Asp Tyr Ser Gln Gly Gly
1505                1510                1515                1520

Thr Arg Leu Asp Gly Lys Asn Leu Val Gln Glu Trp Leu Ala Lys Arg
                1525                1530                1535

Gln Gly Ala Arg Tyr Val Trp Asn Arg Thr Glu Leu Met Gln Ala Ser
            1540                1545                1550

Leu Asp Pro Ser Val Thr His Leu Met Gly Leu Phe Glu Pro Gly Asp
        1555                1560                1565

Met Lys Tyr Glu Ile His Arg Asp Ser Thr Leu Asp Pro Ser Leu Met
    1570                1575                1580

Glu Met Thr Glu Ala Ala Leu Arg Leu Leu Ser Arg Asn Pro Arg Gly
1585                1590                1595                1600

Phe Phe Leu Phe Val Glu Gly Gly Arg Ile Asp His Gly His His Glu
                1605                1610                1615

Ser Arg Ala Tyr Arg Ala Leu Thr Glu Thr Ile Met Phe Asp Asp Ala
            1620                1625                1630

Ile Glu Arg Ala Gly Gln Leu Thr Ser Glu Glu Asp Thr Leu Ser Leu
        1635                1640                1645

Val Thr Ala Asp His Ser His Val Phe Ser Phe Gly Gly Tyr Pro Leu
    1650                1655                1660

Arg Gly Ser Cys Ile Phe Gly Leu Ala Pro Gly Lys Ala Arg Asp Arg
1665                1670                1675                1680

Lys Ala Tyr Thr Val Leu Leu Tyr Gly Asn Gly Pro Gly Tyr Val Leu
                1685                1690                1695

Lys Asp Gly Ala Arg Pro Asp Val Thr Glu Ser Glu Ser Gly Ser Pro
            1700                1705                1710

Glu Tyr Arg Gln Gln Ser Ala Val Pro Leu Asp Glu Glu Thr His Ala
        1715                1720                1725

Gly Glu Asp Val Ala Val Phe Ala Arg Gly Pro Gln Ala His Leu Val
    1730                1735                1740

His Gly Val Gln Glu Gln Thr Phe Ile Ala His Val Met Ala Phe Ala
1745                1750                1755                1760

Ala Cys Leu Glu Pro Tyr Thr Ala Cys Asp Leu Ala Pro Pro Ala Gly
                1765                1770                1775

Thr Thr Asp Ala Ala His Pro Gly Met Ser Glu Lys Tyr Ile Val Thr
            1780                1785                1790
```

-continued

```
Trp Asp Met Leu Gln Ile His Ala Arg Lys Leu Ala Ser Arg Leu Met
       1795                1800                1805

Pro Ser Glu Gln Trp Lys Gly Ile Ile Ala Val Ser Arg Gly Gly Leu
   1810                1815                1820

Val Pro Gly Ala Leu Leu Ala Arg Glu Leu Gly Ile Arg His Val Asp
1825                1830                1835                1840

Thr Val Cys Ile Ser Ser Tyr Asp His Asp Asn Gln Arg Glu Leu Lys
               1845                1850                1855

Val Leu Lys Arg Ala Glu Gly Asp Gly Glu Gly Phe Ile Val Ile Asp
           1860                1865                1870

Asp Leu Val Asp Thr Gly Gly Thr Ala Val Ala Ile Arg Glu Met Tyr
       1875                1880                1885

Pro Lys Ala His Phe Val Thr Ile Phe Ala Lys Pro Ala Gly Arg Pro
   1890                1895                1900

Leu Val Asp Asp Tyr Val Val Asp Ile Pro Gln Asp Thr Trp Ile Glu
1905                1910                1915                1920

Gln Pro Trp Asp Met Gly Val Val Phe Val Pro Pro Ile Ser Gly Arg
               1925                1930                1935

Phe Cys Glu Arg Met Ala Asn Glu Gly Lys Ile Val Ile Val Ala Ala
           1940                1945                1950

Leu Asp Gly Thr Phe Gln Arg Lys Pro Phe Asn Asn Ile Leu Asn Leu
       1955                1960                1965

Ile Pro Leu Ser Glu Met Val Val Lys Leu Thr Ala Val Cys Met Lys
   1970                1975                1980

Cys Phe Lys Glu Ala Ser Phe Ser Lys Arg Leu Gly Glu Glu Thr Glu
1985                1990                1995                2000

Ile Glu Ile Ile Gly Gly Asn Asp Met Tyr Gln Ser Val Cys Arg Lys
               2005                2010                2015

Cys Tyr Ile Asp Ser Met Ser Ile Gln His Phe Arg Val Ala Leu Ile
           2020                2025                2030

Pro Phe Phe Ala Ala Phe Cys Leu Pro Val Phe Ala His Pro Glu Thr
       2035                2040                2045

Leu Val Lys Val Lys Asp Ala Glu Asp Gln Leu Gly Ala Arg Val Gly
   2050                2055                2060

Tyr Ile Glu Leu Asp Leu Asn Ser Gly Lys Ile Leu Glu Ser Phe Arg
2065                2070                2075                2080

Pro Glu Glu Arg Phe Pro Met Met Ser Thr Phe Lys Val Leu Leu Cys
               2085                2090                2095

Gly Ala Val Leu Ser Arg Ile Asp Ala Gly Gln Glu Gln Leu Gly Arg
           2100                2105                2110

Arg Ile His Tyr Ser Gln Asn Asp Leu Val Glu Tyr Ser Pro Val Thr
       2115                2120                2125

Glu Lys His Leu Thr Asp Gly Met Thr Val Arg Glu Leu Cys Ser Ala
   2130                2135                2140

Ala Ile Thr Met Ser Asp Asn Thr Ala Ala Asn Leu Leu Leu Thr Thr
2145                2150                2155                2160

Ile Gly Gly Pro Lys Glu Leu Thr Ala Phe Leu His Asn Met Gly Asp
               2165                2170                2175

His Val Thr Arg Leu Asp Arg Trp Glu Pro Glu Leu Asn Glu Ala Ile
           2180                2185                2190

Pro Asn Asp Glu Arg Asp Thr Thr Met Pro Val Ala Met Ala Thr Thr
       2195                2200                2205

Leu Arg Lys Leu Leu Thr Gly Glu Leu Leu Thr Leu Ala Ser Arg Gln
```

```
2210                2215                2220

Gln Leu Ile Asp Trp Met Glu Ala Asp Lys Val Ala Gly Pro Leu Leu
2225                2230                2235                2240

Arg Ser Ala Leu Pro Ala Gly Trp Phe Ile Ala Asp Lys Ser Gly Ala
                2245                2250                2255

Gly Glu Arg Gly Ser Arg Gly Ile Ile Ala Ala Leu Gly Pro Asp Gly
            2260                2265                2270

Lys Pro Ser Arg Ile Val Val Ile Tyr Thr Thr Gly Ser Gln Ala Thr
        2275                2280                2285

Met Asp Glu Arg Asn Arg Gln Ile Ala Glu Ile Gly Ala Ser Leu Ile
    2290                2295                2300

Lys His Trp
2305


<210> SEQ ID NO 3
<211> LENGTH: 92
<212> TYPE: PRT
<213> ORGANISM: Artificial Sequence
<220> FEATURE:
<223> OTHER INFORMATION: :

<400> SEQUENCE: 3

Met Asn Gly Gly His Ile Gln Leu Ile Ile Gly Pro Met Phe Ser Gly
  1               5                  10                  15

Lys Ser Thr Glu Leu Ile Arg Arg Val Arg Arg Tyr Gln Ile Ala Gln
             20                  25                  30

Tyr Lys Cys Val Thr Ile Lys Tyr Ser Asn Asp Asn Arg Tyr Gly Thr
         35                  40                  45

Gly Leu Trp Thr His Asp Lys Asn Asn Phe Glu Ala Leu Glu Ala Thr
     50                  55                  60

Lys Leu Cys Asp Val Leu Glu Ser Ile Thr Asp Phe Ser Val Ile Gly
 65                  70                  75                  80

Ile Asp Glu Gly Gln Phe Phe Pro Asp Ile Val Glu
                 85                  90


<210> SEQ ID NO 4
<211> LENGTH: 1692
<212> TYPE: PRT
<213> ORGANISM: Artificial Sequence
<220> FEATURE:
<223> OTHER INFORMATION: :

<400> SEQUENCE: 4

Met Gly Ile Pro Gln Phe Met Ala Arg Val Cys Ala Cys Leu Trp Met
  1               5                  10                  15

Met Leu Leu Ile Ala Gln Ala Glu Ala Ala Leu Glu Asn Leu Val Val
             20                  25                  30

Leu Asn Ala Ala Ser Val Ala Gly Ala His Gly Ile Leu Ser Phe Leu
         35                  40                  45

Val Phe Phe Cys Ala Ala Trp Tyr Ile Lys Gly Arg Leu Val Pro Gly
     50                  55                  60

Ala Ala Tyr Ala Leu Tyr Gly Val Trp Pro Leu Leu Leu Leu Leu Leu
 65                  70                  75                  80

Ala Leu Pro Pro Arg Ala Tyr Ala Met Asp Arg Glu Met Ala Ala Ser
                 85                  90                  95

Cys Gly Gly Ala Val Phe Val Gly Leu Val Leu Leu Thr Leu Ser Pro
            100                 105                 110
```

-continued

```
Tyr Tyr Lys Val Phe Leu Ala Arg Leu Ile Trp Trp Leu Gln Tyr Phe
        115                 120                 125

Thr Thr Arg Ala Glu Ala His Leu His Val Trp Ile Pro Pro Leu Asn
    130                 135                 140

Ala Arg Gly Gly Arg Asp Ala Ile Ile Leu Leu Met Cys Ala Val His
145                 150                 155                 160

Pro Glu Leu Ile Phe Asp Ile Thr Lys Leu Leu Ile Ala Ile Leu Gly
                165                 170                 175

Pro Leu Met Val Leu Gln Ala Gly Ile Thr Arg Val Pro Tyr Phe Val
            180                 185                 190

Arg Ala Gln Gly Leu Ile His Ala Cys Met Leu Val Arg Lys Val Ala
        195                 200                 205

Gly Gly His Tyr Val Gln Met Ala Phe Met Lys Leu Gly Ala Leu Thr
    210                 215                 220

Gly Thr Tyr Ile Tyr Asn His Leu Thr Pro Leu Arg Asp Trp Ala His
225                 230                 235                 240

Ala Gly Leu Arg Asp Leu Ala Val Ala Val Glu Pro Val Val Phe Ser
                245                 250                 255

Asp Met Glu Thr Lys Ile Ile Thr Trp Gly Ala Asp Thr Ala Ala Cys
            260                 265                 270

Gly Asp Ile Ile Leu Gly Leu Pro Val Ser Ala Arg Arg Gly Lys Glu
        275                 280                 285

Ile Leu Leu Gly Pro Ala Asp Ser Leu Glu Gly Arg Gly Trp Arg Leu
    290                 295                 300

Leu Ala Pro Ile Thr Ala Tyr Ser Gln Gln Thr Arg Gly Leu Leu Gly
305                 310                 315                 320

Cys Ile Ile Thr Ser Leu Thr Gly Arg Asp Lys Asn Gln Val Glu Gly
                325                 330                 335

Glu Val Gln Val Val Ser Thr Ala Thr Gln Ser Phe Leu Ala Thr Cys
            340                 345                 350

Val Asn Gly Val Cys Trp Thr Val Tyr His Gly Ala Gly Ser Lys Thr
        355                 360                 365

Leu Ala Gly Pro Lys Gly Pro Ile Thr Gln Met Tyr Thr Asn Val Asp
    370                 375                 380

Gln Asp Leu Val Gly Trp Gln Ala Pro Pro Gly Ala Arg Ser Leu Thr
385                 390                 395                 400

Pro Cys Thr Cys Gly Ser Ser Asp Leu Tyr Leu Val Thr Arg His Ala
                405                 410                 415

Asp Val Ile Pro Val Arg Arg Arg Gly Asp Ser Arg Gly Ser Leu Leu
            420                 425                 430

Ser Pro Arg Pro Val Ser Tyr Leu Lys Gly Ser Ser Gly Gly Pro Leu
        435                 440                 445

Leu Cys Pro Ser Gly His Ala Val Gly Ile Phe Arg Ala Ala Val Cys
    450                 455                 460

Thr Arg Gly Val Ala Lys Ala Val Asp Phe Val Pro Val Glu Ser Met
465                 470                 475                 480

Glu Thr Thr Met Arg Ser Pro Val Phe Thr Asp Asn Ser Ser Pro Pro
                485                 490                 495

Ala Val Pro Gln Ser Phe Gln Val Ala His Leu His Ala Pro Thr Gly
            500                 505                 510

Ser Gly Lys Ser Thr Lys Val Pro Ala Ala Tyr Ala Ala Gln Gly Tyr
        515                 520                 525

Lys Val Leu Val Leu Asn Pro Ser Val Ala Ala Thr Leu Gly Phe Gly
```

-continued

```
    530                 535                 540

Ala Tyr Met Ser Lys Ala His Gly Ile Asp Pro Asn Ile Arg Thr Gly
545                 550                 555                 560

Val Arg Thr Ile Thr Thr Gly Ala Pro Val Thr Tyr Ser Thr Tyr Gly
                565                 570                 575

Lys Phe Leu Ala Asp Gly Gly Cys Ser Gly Gly Ala Tyr Asp Ile Ile
            580                 585                 590

Ile Cys Asp Glu Cys His Ser Thr Asp Ser Thr Thr Ile Leu Gly Ile
        595                 600                 605

Gly Thr Val Leu Asp Gln Ala Glu Thr Ala Gly Ala Arg Leu Val Val
    610                 615                 620

Leu Ala Thr Ala Thr Pro Pro Gly Ser Val Thr Val Pro His Pro Asn
625                 630                 635                 640

Ile Glu Glu Val Ala Leu Ser Asn Thr Gly Glu Ile Pro Phe Tyr Gly
                645                 650                 655

Lys Ala Ile Pro Ile Glu Ala Ile Arg Gly Gly Arg His Leu Ile Phe
            660                 665                 670

Cys His Ser Lys Lys Lys Cys Asp Glu Leu Ala Ala Lys Leu Ser Gly
        675                 680                 685

Leu Gly Ile Asn Ala Val Ala Tyr Tyr Arg Gly Leu Asp Val Ser Val
    690                 695                 700

Ile Pro Thr Ile Gly Asp Val Val Val Val Ala Thr Asp Ala Leu Met
705                 710                 715                 720

Thr Gly Tyr Thr Gly Asp Phe Asp Ser Val Ile Asp Cys Asn Thr Cys
                725                 730                 735

Val Thr Gln Thr Val Asp Phe Ser Leu Asp Pro Thr Phe Thr Ile Glu
            740                 745                 750

Thr Thr Thr Val Pro Gln Asp Ala Val Ser Arg Ser Gln Arg Arg Gly
        755                 760                 765

Arg Thr Gly Arg Gly Arg Arg Gly Ile Tyr Arg Phe Val Thr Pro Gly
    770                 775                 780

Glu Arg Pro Ser Gly Met Phe Asp Ser Ser Val Leu Cys Glu Cys Tyr
785                 790                 795                 800

Asp Ala Gly Cys Ala Trp Tyr Glu Leu Thr Pro Ala Glu Thr Ser Val
                805                 810                 815

Arg Leu Arg Ala Tyr Leu Asn Thr Pro Gly Leu Pro Val Cys Gln Asp
            820                 825                 830

His Leu Glu Phe Trp Glu Ser Val Phe Thr Gly Leu Thr His Ile Asp
        835                 840                 845

Ala His Phe Leu Ser Gln Thr Lys Gln Ala Gly Asp Asn Phe Pro Tyr
    850                 855                 860

Leu Val Ala Tyr Gln Ala Thr Val Cys Ala Arg Ala Gln Ala Pro Pro
865                 870                 875                 880

Pro Ser Trp Asp Gln Met Trp Lys Cys Leu Ile Arg Leu Lys Pro Thr
                885                 890                 895

Leu His Gly Pro Thr Pro Leu Leu Tyr Arg Leu Gly Ala Val Gln Asn
            900                 905                 910

Glu Val Thr Leu Thr His Pro Ile Thr Lys Tyr Ile Met Ala Cys Met
        915                 920                 925

Ser Ala Asp Leu Glu Val Val Thr Ser Thr Trp Val Leu Val Gly Gly
    930                 935                 940

Val Leu Ala Ala Leu Ala Ala Tyr Cys Leu Thr Thr Gly Ser Val Val
945                 950                 955                 960
```

-continued

```
Ile Val Gly Arg Ile Ile Leu Ser Gly Arg Pro Ala Ile Val Pro Asp
            965                 970                 975

Arg Glu Leu Leu Tyr Gln Glu Phe Asp Glu Met Glu Glu Cys Ala Ser
        980                 985                 990

His Leu Pro Tyr Ile Glu Gln Gly Met Gln Leu Ala Glu Gln Phe Lys
    995                1000                1005

Gln Lys Ala Leu Gly Leu Leu Gln Thr Ala Thr Lys Gln Ala Glu Ala
  1010                1015                1020

Ala Ala Pro Val Val Glu Ser Lys Trp Arg Ala Leu Glu Thr Phe Trp
1025                1030                1035                1040

Ala Lys His Met Trp Asn Phe Ile Ser Gly Ile Gln Tyr Leu Ala Gly
            1045                1050                1055

Leu Ser Thr Leu Pro Gly Asn Pro Ala Ile Ala Ser Leu Met Ala Phe
        1060                1065                1070

Thr Ala Ser Ile Thr Ser Pro Leu Thr Thr Gln Ser Thr Leu Leu Phe
    1075                1080                1085

Asn Ile Leu Gly Gly Trp Val Ala Ala Gln Leu Ala Pro Pro Ser Ala
  1090                1095                1100

Ala Ser Ala Phe Val Gly Ala Gly Ile Ala Gly Ala Ala Val Gly Ser
1105                1110                1115                1120

Ile Gly Leu Gly Lys Val Leu Val Asp Ile Leu Ala Gly Tyr Gly Ala
            1125                1130                1135

Gly Val Ala Gly Ala Leu Val Ala Phe Lys Val Met Ser Gly Glu Met
        1140                1145                1150

Pro Ser Thr Glu Asp Leu Val Asn Leu Leu Pro Ala Ile Leu Glu Glu
    1155                1160                1165

Ala Ser Glu Asp Val Val Cys Cys Ser Met Ser Tyr Thr Trp Thr Gly
  1170                1175                1180

Ala Leu Glu Leu Leu Leu Leu Leu Leu Leu Gly Leu Arg Leu Gln Leu
1185                1190                1195                1200

Ser Leu Gly Ile Ile Pro Val Glu Glu Glu Asn Pro Asp Phe Trp Asn
            1205                1210                1215

Arg Glu Ala Ala Glu Ala Leu Gly Ala Ala Lys Lys Leu Gln Pro Ala
        1220                1225                1230

Gln Thr Ala Ala Lys Asn Leu Ile Ile Phe Leu Gly Asp Gly Met Gly
    1235                1240                1245

Val Ser Thr Val Thr Ala Ala Arg Ile Leu Lys Gly Gln Lys Lys Asp
  1250                1255                1260

Lys Leu Gly Pro Glu Ile Pro Leu Ala Met Asp Arg Phe Pro Tyr Val
1265                1270                1275                1280

Ala Leu Ser Lys Thr Tyr Asn Val Asp Lys His Val Pro Asp Ser Gly
            1285                1290                1295

Ala Thr Ala Thr Ala Tyr Leu Cys Gly Val Lys Gly Asn Phe Gln Thr
        1300                1305                1310

Ile Gly Leu Ser Ala Ala Ala Arg Phe Asn Gln Cys Asn Thr Thr Arg
    1315                1320                1325

Gly Asn Glu Val Ile Ser Val Met Asn Arg Ala Lys Lys Ala Gly Lys
  1330                1335                1340

Ser Val Gly Val Val Thr Thr Thr Arg Val Gln His Ala Ser Pro Ala
1345                1350                1355                1360

Gly Thr Tyr Ala His Thr Val Asn Arg Asn Trp Tyr Ser Asp Ala Asp
            1365                1370                1375
```

-continued

```
Val Pro Ala Ser Ala Arg Gln Glu Gly Cys Gln Asp Ile Ala Thr Gln
            1380                1385                1390

Leu Ile Ser Asn Met Asp Ile Asp Val Ile Leu Gly Gly Gly Arg Lys
        1395                1400                1405

Tyr Met Phe Pro Met Gly Thr Pro Asp Pro Glu Tyr Pro Asp Asp Tyr
    1410                1415                1420

Ser Gln Gly Gly Thr Arg Leu Asp Gly Lys Asn Leu Val Gln Glu Trp
1425                1430                1435                1440

Leu Ala Lys Arg Gln Gly Ala Arg Tyr Val Trp Asn Arg Thr Glu Leu
                1445                1450                1455

Met Gln Ala Ser Leu Asp Pro Ser Val Thr His Leu Met Gly Leu Phe
            1460                1465                1470

Glu Pro Gly Asp Met Lys Tyr Glu Ile His Arg Asp Ser Thr Leu Asp
        1475                1480                1485

Pro Ser Leu Met Glu Met Thr Glu Ala Ala Leu Arg Leu Leu Ser Arg
    1490                1495                1500

Asn Pro Arg Gly Phe Phe Leu Phe Val Glu Gly Gly Arg Ile Asp His
1505                1510                1515                1520

Gly His His Glu Ser Arg Ala Tyr Arg Ala Leu Thr Glu Thr Ile Met
                1525                1530                1535

Phe Asp Asp Ala Ile Glu Arg Ala Gly Gln Leu Thr Ser Glu Glu Asp
            1540                1545                1550

Thr Leu Ser Leu Val Thr Ala Asp His Ser His Val Phe Ser Phe Gly
        1555                1560                1565

Gly Tyr Pro Leu Arg Gly Ser Cys Ile Phe Gly Leu Ala Pro Gly Lys
    1570                1575                1580

Ala Arg Asp Arg Lys Ala Tyr Thr Val Leu Leu Tyr Gly Asn Gly Pro
1585                1590                1595                1600

Gly Tyr Val Leu Lys Asp Gly Ala Arg Pro Asp Val Thr Glu Ser Glu
                1605                1610                1615

Ser Gly Ser Pro Glu Tyr Arg Gln Gln Ser Ala Val Pro Leu Asp Glu
            1620                1625                1630

Glu Thr His Ala Gly Glu Asp Val Ala Val Phe Ala Arg Gly Pro Gln
        1635                1640                1645

Ala His Leu Val His Gly Val Gln Glu Gln Thr Phe Ile Ala His Val
    1650                1655                1660

Met Ala Phe Ala Ala Cys Leu Glu Pro Tyr Thr Ala Cys Asp Leu Ala
1665                1670                1675                1680

Pro Pro Ala Gly Thr Thr Asp Ala Ala His Pro Gly
                1685                1690


<210> SEQ ID NO 5
<211> LENGTH: 152
<212> TYPE: PRT
<213> ORGANISM: Artificial Sequence
<220> FEATURE:
<223> OTHER INFORMATION: :

<400> SEQUENCE: 5

Met Ser Glu Lys Tyr Ile Val Thr Trp Asp Met Leu Gln Ile His Ala
  1               5                  10                  15

Arg Lys Leu Ala Ser Arg Leu Met Pro Ser Glu Gln Trp Lys Gly Ile
             20                  25                  30

Ile Ala Val Ser Arg Gly Gly Leu Val Pro Gly Ala Leu Leu Ala Arg
         35                  40                  45
```

-continued

Glu Leu Gly Ile Arg His Val Asp Thr Val Cys Ile Ser Ser Tyr Asp
50 55 60

His Asp Asn Gln Arg Glu Leu Lys Val Leu Lys Arg Ala Glu Gly Asp
65 70 75 80

Gly Glu Gly Phe Ile Val Ile Asp Asp Leu Val Asp Thr Gly Gly Thr
85 90 95

Ala Val Ala Ile Arg Glu Met Tyr Pro Lys Ala His Phe Val Thr Ile
100 105 110

Phe Ala Lys Pro Ala Gly Arg Pro Leu Val Asp Asp Tyr Val Val Asp
115 120 125

Ile Pro Gln Asp Thr Trp Ile Glu Gln Pro Trp Asp Met Gly Val Val
130 135 140

Phe Val Pro Pro Ile Ser Gly Arg
145 150

<210> SEQ ID NO 6
<211> LENGTH: 85
<212> TYPE: PRT
<213> ORGANISM: Artificial Sequence
<220> FEATURE:
<223> OTHER INFORMATION: :

<400> SEQUENCE: 6

Phe Cys Glu Arg Met Ala Asn Glu Gly Lys Ile Val Ile Val Ala Ala
1 5 10 15

Leu Asp Gly Thr Phe Gln Arg Lys Pro Phe Asn Asn Ile Leu Asn Leu
20 25 30

Ile Pro Leu Ser Glu Met Val Val Lys Leu Thr Ala Val Cys Met Lys
35 40 45

Cys Phe Lys Glu Ala Ser Phe Ser Lys Arg Leu Gly Glu Glu Thr Glu
50 55 60

Ile Glu Ile Ile Gly Gly Asn Asp Met Tyr Gln Ser Val Cys Arg Lys
65 70 75 80

Cys Tyr Ile Asp Ser
85

<210> SEQ ID NO 7
<211> LENGTH: 286
<212> TYPE: PRT
<213> ORGANISM: Artificial Sequence
<220> FEATURE:
<223> OTHER INFORMATION: :

<400> SEQUENCE: 7

Met Ser Ile Gln His Phe Arg Val Ala Leu Ile Pro Phe Phe Ala Ala
1 5 10 15

Phe Cys Leu Pro Val Phe Ala His Pro Glu Thr Leu Val Lys Val Lys
20 25 30

Asp Ala Glu Asp Gln Leu Gly Ala Arg Val Gly Tyr Ile Glu Leu Asp
35 40 45

Leu Asn Ser Gly Lys Ile Leu Glu Ser Phe Arg Pro Glu Glu Arg Phe
50 55 60

Pro Met Met Ser Thr Phe Lys Val Leu Leu Cys Gly Ala Val Leu Ser
65 70 75 80

Arg Ile Asp Ala Gly Gln Glu Gln Leu Gly Arg Arg Ile His Tyr Ser
85 90 95

Gln Asn Asp Leu Val Glu Tyr Ser Pro Val Thr Glu Lys His Leu Thr
100 105 110

```
Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp
        275                 280                 285


<210> SEQ ID NO 8
<211> LENGTH: 13910
<212> TYPE: DNA
<213> ORGANISM: Artificial Sequence
<220> FEATURE:
<223> OTHER INFORMATION: Description of Artificial Sequence: plasmid
      phcap 3
<220> FEATURE:
<221> NAME/KEY: CDS
<222> LOCATION: (497)..(772)
<220> FEATURE:
<221> NAME/KEY: CDS
<222> LOCATION: (1425)..(6500)
<220> FEATURE:
<221> NAME/KEY: CDS
<222> LOCATION: (8579)..(9034)
<220> FEATURE:
<221> NAME/KEY: CDS
<222> LOCATION: (10191)..(10445)
<220> FEATURE:
<221> NAME/KEY: CDS
<222> LOCATION: (11877)..(12734)
<220> FEATURE:
<221> NAME/KEY: misc_feature
<222> LOCATION: (1)..(774)
<223> OTHER INFORMATION: Vaccinia Virus thymidine Kinase gene
      recombination site
<220> FEATURE:
<221> NAME/KEY: promoter
<222> LOCATION: (794)..(816)
<223> OTHER INFORMATION: T7 promoter
<220> FEATURE:
<221> NAME/KEY: misc_feature
<222> LOCATION: (846)..(1424)
<223> OTHER INFORMATION: EMC/Internal Ribosome Entry Site (IRES)
<220> FEATURE:
<221> NAME/KEY: misc_feature
<222> LOCATION: (1426)..(1437)
<223> OTHER INFORMATION: MCS (Multiple Cloning Site)
<220> FEATURE:
<221> NAME/KEY: misc_feature
<222> LOCATION: (1446)..(2318)
<223> OTHER INFORMATION: HCV E2/ NS2 domain
<220> FEATURE:
```

-continued

```
<221> NAME/KEY: misc_feature
<222> LOCATION: (2319)..(4231)
<223> OTHER INFORMATION: HCV NS3 Domain containing the serine protease
      and helicase enzymes
<220> FEATURE:
<221> NAME/KEY: misc_feature
<222> LOCATION: (4203)..(4260)
<223> OTHER INFORMATION: HCV NS3-NS4A cleavage site
<220> FEATURE:
<221> NAME/KEY: misc_feature
<222> LOCATION: (4375)..(4424)
<223> OTHER INFORMATION: HCV NS4A-4B clevage site
<220> FEATURE:
<221> NAME/KEY: misc_feature
<222> LOCATION: (4233)..(4394)
<223> OTHER INFORMATION: HCV NS4A domain
<220> FEATURE:
<221> NAME/KEY: misc_feature
<222> LOCATION: (4395)..(4919)
<223> OTHER INFORMATION: HCV NS4B Domain
<220> FEATURE:
<221> NAME/KEY: misc_feature
<222> LOCATION: (4920)..(4991)
<223> OTHER INFORMATION: HCV NS5A-NS5B cleavage site
<220> FEATURE:
<221> NAME/KEY: misc_feature
<222> LOCATION: (4992)..(6501)
<223> OTHER INFORMATION: SEAP Protein
<220> FEATURE:
<221> NAME/KEY: misc_feature
<222> LOCATION: (7915)..(7945)
<223> OTHER INFORMATION: MCS (Multiple Cloning Site)
<220> FEATURE:
<221> NAME/KEY: terminator
<222> LOCATION: (7938)..(8078)
<223> OTHER INFORMATION: term T7
<220> FEATURE:
<221> NAME/KEY: promoter
<222> LOCATION: (8080)..(8365)
<223> OTHER INFORMATION: Vacinina virus promoter; early/late promoter
<220> FEATURE:
<221> NAME/KEY: misc_feature
<222> LOCATION: (8560)..(11317)
<223> OTHER INFORMATION: E. coli gpt; for selection of recombinants
<220> FEATURE:
<221> NAME/KEY: misc_feature
<222> LOCATION: (11318)..(13909)
<223> OTHER INFORMATION: remaining DNA from 3' end of  Tropix pCMV/SEAP
      plasmid

<400> SEQUENCE: 8

aagcttttgc gatcaataaa tggatcacaa ccagtatctc ttaacgatgt tcttcgcaga     60

tgatgattca ttttttaagt atttggctag tcaagatgat gaatcttcat tatctgatat    120

attgcaaatc actcaatatc tagactttct gttattatta ttgatccaat caaaaaataa    180

attagaagcc gtgggtcatt gttatgaatc tctttcagag gaatacagac aattgacaaa    240

attcacagac tttcaagatt ttaaaaaact gtttaacaag gtccctattg ttacagatgg    300

aagggtcaaa cttaataaag gatatttgtt cgactttgtg attagtttga tgcgattcaa    360

aaaagaatcc tctctagcta ccaccgcaat agatcctgtt agatacatag atcctcgtcg    420

caatatcgca ttttctaacg tgatggatat attaaagtcg aataaagtga acaataatta    480

attctttatt gtcatc atg aac ggc gga cat att cag ttg ata atc ggc ccc    532
                  Met Asn Gly Gly His Ile Gln Leu Ile Ile Gly Pro
                    1               5                  10

atg ttt tca ggt aaa agt aca gaa tta att aga cga gtt aga cgt tat      580
Met Phe Ser Gly Lys Ser Thr Glu Leu Ile Arg Arg Val Arg Arg Tyr
         15                  20                  25

caa ata gct caa tat aaa tgc gtg act ata aaa tat tct aac gat aat      628
Gln Ile Ala Gln Tyr Lys Cys Val Thr Ile Lys Tyr Ser Asn Asp Asn
     30                  35                  40
```

-continued

```
aga tac gga acg gga cta tgg acg cat gat aag aat aat ttt gaa gca      676
Arg Tyr Gly Thr Gly Leu Trp Thr His Asp Lys Asn Asn Phe Glu Ala
 45                 50                  55                  60

ttg gaa gca act aaa cta tgt gat gtc ttg gaa tca att aca gat ttc      724
Leu Glu Ala Thr Lys Leu Cys Asp Val Leu Glu Ser Ile Thr Asp Phe
                65                  70                  75

tcc gtg ata ggt atc gat gaa gga cag ttc ttt cca gac att gtt gaa      772
Ser Val Ile Gly Ile Asp Glu Gly Gln Phe Phe Pro Asp Ile Val Glu
            80                  85                  90

ttgatctcga tcccgcgaaa ttaatacgac tcactatagg gagaccacaa cggtttccct    832

ctagcgggat caattccgcc cctctccctc ccccccccct aacgttactg gccgaagccg    892

cttggaataa ggccggtgtg cgtttgtcta tatgttattt tccaccatat tgccgtcttt    952

tggcaatgtg agggcccgga aacctggccc tgtcttcttg acgagcattc ctaggggtct   1012

ttcccctctc gccaaaggaa tgcaaggtct gttgaatgtc gtgaaggaag cagttcctct   1072

ggaagcttct tgaagacaaa caacgtctgt agcgaccctt tgcaggcagc ggaacccccc   1132

acctggcgac aggtgcctct gcggccaaaa gccacgtgta taagatacac ctgcaaaggc   1192

ggcacaaccc cagtgccacg ttgtgagttg gatagttgtg gaaagagtca aatggctctc   1252

ctcaagcgta ttcaacaagg ggctgaagga tgcccagaag gtaccccatt gtatgggatc   1312

tgatctgggg cctcggtgca catgctttac atgtgtttag tcgaggttaa aaaacgtcta   1372

ggccccccga accacgggga cgtggttttc ctttgaaaaa cacgataata cc atg gga   1430
                                                          Met Gly

att ccc caa ttc atg gca cgt gtc tgt gcc tgc ttg tgg atg atg ctg     1478
Ile Pro Gln Phe Met Ala Arg Val Cys Ala Cys Leu Trp Met Met Leu
 95                 100                 105                 110

ctg ata gcc cag gcc gag gcc gcc ttg gag aac ctg gtg gtc ctc aat     1526
Leu Ile Ala Gln Ala Glu Ala Ala Leu Glu Asn Leu Val Val Leu Asn
                115                 120                 125

gcg gcg tct gtg gcc ggc gca cat ggc atc ctc tcc ttc ctt gtg ttc     1574
Ala Ala Ser Val Ala Gly Ala His Gly Ile Leu Ser Phe Leu Val Phe
            130                 135                 140

ttc tgt gcc gcc tgg tac atc aaa ggc agg ctg gtc cct ggg gcg gca     1622
Phe Cys Ala Ala Trp Tyr Ile Lys Gly Arg Leu Val Pro Gly Ala Ala
        145                 150                 155

tat gct ctt tat ggc gtg tgg ccg ctg ctc ctg ctc ttg ctg gca tta     1670
Tyr Ala Leu Tyr Gly Val Trp Pro Leu Leu Leu Leu Leu Leu Ala Leu
    160                 165                 170

cca ccg cga gct tac gcc atg gac cgg gag atg gct gca tcg tgc gga     1718
Pro Pro Arg Ala Tyr Ala Met Asp Arg Glu Met Ala Ala Ser Cys Gly
175                 180                 185                 190

ggc gcg gtt ttt gtg ggt ctg gta ctc ctg act ttg tca cca tac tac     1766
Gly Ala Val Phe Val Gly Leu Val Leu Leu Thr Leu Ser Pro Tyr Tyr
                195                 200                 205

aag gtg ttc ctc gct agg ctc ata tgg tgg tta caa tat ttt acc acc     1814
Lys Val Phe Leu Ala Arg Leu Ile Trp Trp Leu Gln Tyr Phe Thr Thr
            210                 215                 220

aga gcc gag gcg cac tta cat gtg tgg atc ccc ccc ctc aac gct cgg     1862
Arg Ala Glu Ala His Leu His Val Trp Ile Pro Pro Leu Asn Ala Arg
        225                 230                 235

gga ggc cgc gat gcc atc atc ctc ctc atg tgc gca gtc cat cca gag     1910
Gly Gly Arg Asp Ala Ile Ile Leu Leu Met Cys Ala Val His Pro Glu
    240                 245                 250

cta atc ttt gac atc acc aaa ctt cta att gcc ata ctc ggt ccg ctc     1958
Leu Ile Phe Asp Ile Thr Lys Leu Leu Ile Ala Ile Leu Gly Pro Leu
255                 260                 265                 270
```

```
atg gtg ctc caa gct ggc ata acc aga gtg ccg tac ttc gtg cgc gct     2006
Met Val Leu Gln Ala Gly Ile Thr Arg Val Pro Tyr Phe Val Arg Ala
                275                 280                 285

caa ggg ctc att cat gca tgc atg tta gtg cgg aag gtc gct ggg ggt     2054
Gln Gly Leu Ile His Ala Cys Met Leu Val Arg Lys Val Ala Gly Gly
            290                 295                 300

cat tat gtc caa atg gcc ttc atg aag ctg ggc gcg ctg aca ggc acg     2102
His Tyr Val Gln Met Ala Phe Met Lys Leu Gly Ala Leu Thr Gly Thr
        305                 310                 315

tac att tac aac cat ctt acc ccg cta cgg gat tgg gcc cac gcg ggc     2150
Tyr Ile Tyr Asn His Leu Thr Pro Leu Arg Asp Trp Ala His Ala Gly
    320                 325                 330

cta cga gac ctt gcg gtg gca gtg gag ccc gtc gtc ttc tcc gac atg     2198
Leu Arg Asp Leu Ala Val Ala Val Glu Pro Val Val Phe Ser Asp Met
335                 340                 345                 350

gag acc aag atc atc acc tgg gga gca gac acc gcg gcg tgt ggg gac     2246
Glu Thr Lys Ile Ile Thr Trp Gly Ala Asp Thr Ala Ala Cys Gly Asp
                355                 360                 365

atc atc ttg ggt ctg ccc gtc tcc gcc cga agg gga aag gag ata ctc     2294
Ile Ile Leu Gly Leu Pro Val Ser Ala Arg Arg Gly Lys Glu Ile Leu
            370                 375                 380

ctg ggc ccg gcc gat agt ctt gaa ggg cgg ggg tgg cga ctc ctc gcg     2342
Leu Gly Pro Ala Asp Ser Leu Glu Gly Arg Gly Trp Arg Leu Leu Ala
        385                 390                 395

ccc atc acg gcc tac tcc caa cag acg cgg ggc cta ctt ggt tgc atc     2390
Pro Ile Thr Ala Tyr Ser Gln Gln Thr Arg Gly Leu Leu Gly Cys Ile
    400                 405                 410

atc act agc ctt aca ggc cgg gac aag aac cag gtc gag gga gag gtt     2438
Ile Thr Ser Leu Thr Gly Arg Asp Lys Asn Gln Val Glu Gly Glu Val
415                 420                 425                 430

cag gtg gtt tcc acc gca aca caa tcc ttc ctg gcg acc tgc gtc aac     2486
Gln Val Val Ser Thr Ala Thr Gln Ser Phe Leu Ala Thr Cys Val Asn
                435                 440                 445

ggc gtg tgt tgg acc gtt tac cat ggt gct ggc tca aag acc tta gcc     2534
Gly Val Cys Trp Thr Val Tyr His Gly Ala Gly Ser Lys Thr Leu Ala
            450                 455                 460

ggc cca aag ggg cca atc acc cag atg tac act aat gtg gac cag gac     2582
Gly Pro Lys Gly Pro Ile Thr Gln Met Tyr Thr Asn Val Asp Gln Asp
        465                 470                 475

ctc gtc ggc tgg cag gcg ccc ccc ggg gcg cgt tcc ttg aca cca tgc     2630
Leu Val Gly Trp Gln Ala Pro Pro Gly Ala Arg Ser Leu Thr Pro Cys
    480                 485                 490

acc tgt ggc agc tca gac ctt tac ttg gtc acg aga cat gct gac gtc     2678
Thr Cys Gly Ser Ser Asp Leu Tyr Leu Val Thr Arg His Ala Asp Val
495                 500                 505                 510

att ccg gtg cgc cgg cgg ggc gac agt agg ggg agc ctg ctc tcc ccc     2726
Ile Pro Val Arg Arg Arg Gly Asp Ser Arg Gly Ser Leu Leu Ser Pro
                515                 520                 525

agg cct gtc tcc tac ttg aag ggc tct gcg ggt ggt cca ctg ctc tgc     2774
Arg Pro Val Ser Tyr Leu Lys Gly Ser Ala Gly Gly Pro Leu Leu Cys
            530                 535                 540

cct tcg ggg cac gct gtg ggc atc ttc cgg gct gcc gta tgc acc cgg     2822
Pro Ser Gly His Ala Val Gly Ile Phe Arg Ala Ala Val Cys Thr Arg
        545                 550                 555

ggg gtt gcg aag gcg gtg gac ttt gtg ccc gta gag tcc atg gaa act     2870
Gly Val Ala Lys Ala Val Asp Phe Val Pro Val Glu Ser Met Glu Thr
    560                 565                 570

act atg cgg tct ccg gtc ttc acg gac aac tca tcc ccc ccg gcc gta     2918
Thr Met Arg Ser Pro Val Phe Thr Asp Asn Ser Ser Pro Pro Ala Val
```

-continued

```
575                 580                 585                 590

ccg cag tca ttt caa gtg gcc cac cta cac gct ccc act ggc agc ggc     2966
Pro Gln Ser Phe Gln Val Ala His Leu His Ala Pro Thr Gly Ser Gly
                595                 600                 605

aag agt act aaa gtg ccg gct gca tat gca gcc caa ggg tac aag gtg     3014
Lys Ser Thr Lys Val Pro Ala Ala Tyr Ala Ala Gln Gly Tyr Lys Val
            610                 615                 620

ctc gtc ctc aat ccg tcc gtt gcc gct acc tta ggg ttt ggg gcg tat     3062
Leu Val Leu Asn Pro Ser Val Ala Ala Thr Leu Gly Phe Gly Ala Tyr
        625                 630                 635

atg tct aag gca cac ggt att gac ccc aac atc aga act ggg gta agg     3110
Met Ser Lys Ala His Gly Ile Asp Pro Asn Ile Arg Thr Gly Val Arg
    640                 645                 650

acc att acc aca ggc gcc ccc gtc aca tac tct acc tat ggc aag ttt     3158
Thr Ile Thr Thr Gly Ala Pro Val Thr Tyr Ser Thr Tyr Gly Lys Phe
655                 660                 665                 670

ctt gcc gat ggt ggt tgc tct ggg ggc gct tat gac atc ata ata tgt     3206
Leu Ala Asp Gly Gly Cys Ser Gly Gly Ala Tyr Asp Ile Ile Ile Cys
                675                 680                 685

gat gag tgc cat tca act gac tcg act aca atc ttg ggc atc ggc aca     3254
Asp Glu Cys His Ser Thr Asp Ser Thr Thr Ile Leu Gly Ile Gly Thr
            690                 695                 700

gtc ctg gac caa gcg gag acg gct gga gcg cgg ctt gtc gtg ctc gcc     3302
Val Leu Asp Gln Ala Glu Thr Ala Gly Ala Arg Leu Val Val Leu Ala
        705                 710                 715

acc gct acg cct ccg gga tcg gtc acc gtg cca cac cca aac atc gag     3350
Thr Ala Thr Pro Pro Gly Ser Val Thr Val Pro His Pro Asn Ile Glu
    720                 725                 730

gag gtg gcc ctg tct aat act gga gag atc ccc ttc tat ggc aaa gcc     3398
Glu Val Ala Leu Ser Asn Thr Gly Glu Ile Pro Phe Tyr Gly Lys Ala
735                 740                 745                 750

atc ccc att gaa gcc atc agg ggg gga agg cat ctc att ttc tgt cat     3446
Ile Pro Ile Glu Ala Ile Arg Gly Gly Arg His Leu Ile Phe Cys His
                755                 760                 765

tcc aag aag aag tgc gac gag ctc gcc gca aag ctg tca ggc ctc gga     3494
Ser Lys Lys Lys Cys Asp Glu Leu Ala Ala Lys Leu Ser Gly Leu Gly
            770                 775                 780

atc aac gct gtg gcg tat tac cgg ggg ctc gat gtg tcc gtc ata cca     3542
Ile Asn Ala Val Ala Tyr Tyr Arg Gly Leu Asp Val Ser Val Ile Pro
        785                 790                 795

act atc gga gac gtc gtt gtc gtg gca aca gac gct ctg atg acg ggc     3590
Thr Ile Gly Asp Val Val Val Val Ala Thr Asp Ala Leu Met Thr Gly
    800                 805                 810

tat acg ggc gac ttt gac tca gtg atc gac tgt aac aca tgt gtc acc     3638
Tyr Thr Gly Asp Phe Asp Ser Val Ile Asp Cys Asn Thr Cys Val Thr
815                 820                 825                 830

cag aca gtc gac ttc agc ttg gat ccc acc ttc acc att gag acg acg     3686
Gln Thr Val Asp Phe Ser Leu Asp Pro Thr Phe Thr Ile Glu Thr Thr
                835                 840                 845

acc gtg cct caa gac gca gtg tcg cgc tcg cag cgg cgg ggt agg act     3734
Thr Val Pro Gln Asp Ala Val Ser Arg Ser Gln Arg Arg Gly Arg Thr
            850                 855                 860

ggc agg ggt agg aga ggc atc tac agg ttt gtg act ccg gga gaa cgg     3782
Gly Arg Gly Arg Arg Gly Ile Tyr Arg Phe Val Thr Pro Gly Glu Arg
        865                 870                 875

ccc tcg ggc atg ttc gat tcc tcg gtc ctg tgt gag tgc tat gac gcg     3830
Pro Ser Gly Met Phe Asp Ser Ser Val Leu Cys Glu Cys Tyr Asp Ala
    880                 885                 890

ggc tgt gct tgg tac gag ctc acc ccc gcc gag acc tcg gtt agg ttg     3878
```

-continued

```
Gly Cys Ala Trp Tyr Glu Leu Thr Pro Ala Glu Thr Ser Val Arg Leu
895                 900                 905                 910

cgg gcc tac ctg aac aca cca ggg ttg ccc gtt tgc cag gac cac ctg     3926
Arg Ala Tyr Leu Asn Thr Pro Gly Leu Pro Val Cys Gln Asp His Leu
                915                 920                 925

gag ttc tgg gag agt gtc ttc aca ggc ctc acc cat ata gat gca cac     3974
Glu Phe Trp Glu Ser Val Phe Thr Gly Leu Thr His Ile Asp Ala His
            930                 935                 940

ttc ttg tcc cag acc aag cag gca gga gac aac ttc ccc tac ctg gta     4022
Phe Leu Ser Gln Thr Lys Gln Ala Gly Asp Asn Phe Pro Tyr Leu Val
        945                 950                 955

gca tac caa gcc acg gtg tgc gcc agg gct cag gcc cca cct cca tca     4070
Ala Tyr Gln Ala Thr Val Cys Ala Arg Ala Gln Ala Pro Pro Pro Ser
    960                 965                 970

tgg gat caa atg tgg aag tgt ctc ata cgg ctg aaa cct acg ctg cac     4118
Trp Asp Gln Met Trp Lys Cys Leu Ile Arg Leu Lys Pro Thr Leu His
975                 980                 985                 990

ggg cca aca ccc ttg ctg tac agg ctg gga gcc gtc caa aat gag gtc     4166
Gly Pro Thr Pro Leu Leu Tyr Arg Leu Gly Ala Val Gln Asn Glu Val
                995                1000                1005

acc ctc acc cac ccc ata acc aaa tac atc atg gca tgc atg tcg gct     4214
Thr Leu Thr His Pro Ile Thr Lys Tyr Ile Met Ala Cys Met Ser Ala
           1010                1015                1020

gac ctg gag gtc gtc act agc acc tgg gtg ctg gtg ggc gga gtc ctt     4262
Asp Leu Glu Val Val Thr Ser Thr Trp Val Leu Val Gly Gly Val Leu
       1025                1030                1035

gca gct ctg gcc gcg tat tgc ctg aca aca ggc agt gtg gtc att gtg     4310
Ala Ala Leu Ala Ala Tyr Cys Leu Thr Thr Gly Ser Val Val Ile Val
   1040                1045                1050

ggt agg att atc ttg tcc ggg agg ccg gcc att gtt ccc gac agg gag     4358
Gly Arg Ile Ile Leu Ser Gly Arg Pro Ala Ile Val Pro Asp Arg Glu
1055               1060                1065                1070

ctt ctc tac cag gag ttc gat gaa atg gaa gag tgc gcc tcg cac ctc     4406
Leu Leu Tyr Gln Glu Phe Asp Glu Met Glu Glu Cys Ala Ser His Leu
               1075                1080                1085

cct tac atc gag cag gga atg cag ctc gcc gag caa ttc aag cag aaa     4454
Pro Tyr Ile Glu Gln Gly Met Gln Leu Ala Glu Gln Phe Lys Gln Lys
           1090                1095                1100

gcg ctc ggg tta ctg caa aca gcc acc aaa caa gcg gag gct gct gct     4502
Ala Leu Gly Leu Leu Gln Thr Ala Thr Lys Gln Ala Glu Ala Ala Ala
       1105                1110                1115

ccc gtg gtg gag tcc aag tgg cga gcc ctt gag aca ttc tgg gcg aag     4550
Pro Val Val Glu Ser Lys Trp Arg Ala Leu Glu Thr Phe Trp Ala Lys
   1120                1125                1130

cac atg tgg aat ttc atc agc ggg ata cag tac tta gca ggc tta tcc     4598
His Met Trp Asn Phe Ile Ser Gly Ile Gln Tyr Leu Ala Gly Leu Ser
1135               1140                1145                1150

act ctg cct ggg aac ccc gca ata gca tca ttg atg gca ttc aca gcc     4646
Thr Leu Pro Gly Asn Pro Ala Ile Ala Ser Leu Met Ala Phe Thr Ala
               1155                1160                1165

tct atc acc agc ccg ctc acc acc caa agt acc ctc ctg ttt aac atc     4694
Ser Ile Thr Ser Pro Leu Thr Thr Gln Ser Thr Leu Leu Phe Asn Ile
           1170                1175                1180

ttg ggg ggg tgg gtg gct gcc caa ctc gcc ccc ccc agc gcc gct tcg     4742
Leu Gly Gly Trp Val Ala Ala Gln Leu Ala Pro Pro Ser Ala Ala Ser
       1185                1190                1195

gct ttc gtg ggc gcc ggc atc gcc ggt gcg gct gtt ggc agc ata ggc     4790
Ala Phe Val Gly Ala Gly Ile Ala Gly Ala Ala Val Gly Ser Ile Gly
   1200                1205                1210
```

-continued

```
ctt ggg aag gtg ctt gtg gac att ctg gcg ggt tat gga gca gga gtg     4838
Leu Gly Lys Val Leu Val Asp Ile Leu Ala Gly Tyr Gly Ala Gly Val
1215                1220                1225                1230

gcc ggc gcg ctc gtg gcc ttt aag gtc atg agc ggc gag atg ccc tcc     4886
Ala Gly Ala Leu Val Ala Phe Lys Val Met Ser Gly Glu Met Pro Ser
                1235                1240                1245

acc gag gac ctg gtc aat cta ctt cct gcc atc ctc gag gaa gct agt     4934
Thr Glu Asp Leu Val Asn Leu Leu Pro Ala Ile Leu Glu Glu Ala Ser
            1250                1255                1260

gag gat gtc gtc tgc tgc tca atg tcc tac aca tgg aca ggc gcc ttg     4982
Glu Asp Val Val Cys Cys Ser Met Ser Tyr Thr Trp Thr Gly Ala Leu
        1265                1270                1275

gag ctg ctg ctg ctg ctg ctg ctg ggc ctg agg cta cag ctc tcc ctg     5030
Glu Leu Leu Leu Leu Leu Leu Leu Gly Leu Arg Leu Gln Leu Ser Leu
    1280                1285                1290

ggc atc atc cca gtt gag gag gag aac ccg gac ttc tgg aac cgc gag     5078
Gly Ile Ile Pro Val Glu Glu Glu Asn Pro Asp Phe Trp Asn Arg Glu
1295                1300                1305                1310

gca gcc gag gcc ctg ggt gcc gcc aag aag ctg cag cct gca cag aca     5126
Ala Ala Glu Ala Leu Gly Ala Ala Lys Lys Leu Gln Pro Ala Gln Thr
                1315                1320                1325

gcc gcc aag aac ctc atc atc ttc ctg ggc gat ggg atg ggg gtg tct     5174
Ala Ala Lys Asn Leu Ile Ile Phe Leu Gly Asp Gly Met Gly Val Ser
            1330                1335                1340

acg gtg aca gct gcc agg atc cta aaa ggg cag aag aag gac aaa ctg     5222
Thr Val Thr Ala Ala Arg Ile Leu Lys Gly Gln Lys Lys Asp Lys Leu
        1345                1350                1355

ggg cct gag ata ccc ctg gcc atg gac cgc ttc cca tat gtg gct ctg     5270
Gly Pro Glu Ile Pro Leu Ala Met Asp Arg Phe Pro Tyr Val Ala Leu
    1360                1365                1370

tcc aag aca tac aat gta gac aaa cat gtg cca gac agt gga gcc aca     5318
Ser Lys Thr Tyr Asn Val Asp Lys His Val Pro Asp Ser Gly Ala Thr
1375                1380                1385                1390

gcc acg gcc tac ctg tgc ggg gtc aag ggc aac ttc cag acc att ggc     5366
Ala Thr Ala Tyr Leu Cys Gly Val Lys Gly Asn Phe Gln Thr Ile Gly
                1395                1400                1405

ttg agt gca gcc gcc cgc ttt aac cag tgc aac acg aca cgc ggc aac     5414
Leu Ser Ala Ala Ala Arg Phe Asn Gln Cys Asn Thr Thr Arg Gly Asn
            1410                1415                1420

gag gtc atc tcc gtg atg aat cgg gcc aag aaa gca ggg aag tca gtg     5462
Glu Val Ile Ser Val Met Asn Arg Ala Lys Lys Ala Gly Lys Ser Val
        1425                1430                1435

gga gtg gta acc acc aca cga gtg cag cac gcc tcg cca gcc ggc acc     5510
Gly Val Val Thr Thr Thr Arg Val Gln His Ala Ser Pro Ala Gly Thr
    1440                1445                1450

tac gcc cac acg gtg aac cgc aac tgg tac tcg gac gcc gac gtg cct     5558
Tyr Ala His Thr Val Asn Arg Asn Trp Tyr Ser Asp Ala Asp Val Pro
1455                1460                1465                1470

gcc tcg gcc cgc cag gag ggg tgc cag gac atc gct acg cag ctc atc     5606
Ala Ser Ala Arg Gln Glu Gly Cys Gln Asp Ile Ala Thr Gln Leu Ile
                1475                1480                1485

tcc aac atg gac att gac gtg atc cta ggt gga ggc cga aag tac atg     5654
Ser Asn Met Asp Ile Asp Val Ile Leu Gly Gly Gly Arg Lys Tyr Met
            1490                1495                1500

ttt ccc atg gga acc cca gac cct gag tac cca gat gac tac agc caa     5702
Phe Pro Met Gly Thr Pro Asp Pro Glu Tyr Pro Asp Asp Tyr Ser Gln
        1505                1510                1515

ggt ggg acc agg ctg gac ggg aag aat ctg gtg cag gaa tgg ctg gcg     5750
Gly Gly Thr Arg Leu Asp Gly Lys Asn Leu Val Gln Glu Trp Leu Ala
    1520                1525                1530
```

-continued

```
aag cgc cag ggt gcc cgg tat gtg tgg aac cgc act gag ctg atg cag     5798
Lys Arg Gln Gly Ala Arg Tyr Val Trp Asn Arg Thr Glu Leu Met Gln
1535                1540                1545                1550

gct tcc ctg gac ccg tct gtg acc cat ctc atg ggt ctc ttt gag cct     5846
Ala Ser Leu Asp Pro Ser Val Thr His Leu Met Gly Leu Phe Glu Pro
               1555                1560                1565

gga gac atg aaa tac gag atc cac cga gac tcc aca ctg gac ccc tcc     5894
Gly Asp Met Lys Tyr Glu Ile His Arg Asp Ser Thr Leu Asp Pro Ser
           1570                1575                1580

ctg atg gag atg aca gag gct gcc ctg cgc ctg ctg agc agg aac ccc     5942
Leu Met Glu Met Thr Glu Ala Ala Leu Arg Leu Leu Ser Arg Asn Pro
       1585                1590                1595

cgc ggc ttc ttc ctc ttc gtg gag ggt ggt cgc atc gac cat ggt cat     5990
Arg Gly Phe Phe Leu Phe Val Glu Gly Gly Arg Ile Asp His Gly His
   1600                1605                1610

cat gaa agc agg gct tac cgg gca ctg act gag acg atc atg ttc gac     6038
His Glu Ser Arg Ala Tyr Arg Ala Leu Thr Glu Thr Ile Met Phe Asp
1615                1620                1625                1630

gac gcc att gag agg gcg ggc cag ctc acc agc gag gag gac acg ctg     6086
Asp Ala Ile Glu Arg Ala Gly Gln Leu Thr Ser Glu Glu Asp Thr Leu
               1635                1640                1645

agc ctc gtc act gcc gac cac tcc cac gtc ttc tcc ttc gga ggc tac     6134
Ser Leu Val Thr Ala Asp His Ser His Val Phe Ser Phe Gly Gly Tyr
           1650                1655                1660

ccc ctg cga ggg agc tgc atc ttc ggg ctg gcc cct ggc aag gcc cgg     6182
Pro Leu Arg Gly Ser Cys Ile Phe Gly Leu Ala Pro Gly Lys Ala Arg
       1665                1670                1675

gac agg aag gcc tac acg gtc ctc cta tac gga aac ggt cca ggc tat     6230
Asp Arg Lys Ala Tyr Thr Val Leu Leu Tyr Gly Asn Gly Pro Gly Tyr
   1680                1685                1690

gtg ctc aag gac ggc gcc cgg ccg gat gtt acc gag agc gag agc ggg     6278
Val Leu Lys Asp Gly Ala Arg Pro Asp Val Thr Glu Ser Glu Ser Gly
1695                1700                1705                1710

agc ccc gag tat cgg cag cag tca gca gtg ccc ctg gac gaa gag acc     6326
Ser Pro Glu Tyr Arg Gln Gln Ser Ala Val Pro Leu Asp Glu Glu Thr
               1715                1720                1725

cac gca ggc gag gac gtg gcg gtg ttc gcg cgc ggc ccg cag gcg cac     6374
His Ala Gly Glu Asp Val Ala Val Phe Ala Arg Gly Pro Gln Ala His
           1730                1735                1740

ctg gtt cac ggc gtg cag gag cag acc ttc ata gcg cac gtc atg gcc     6422
Leu Val His Gly Val Gln Glu Gln Thr Phe Ile Ala His Val Met Ala
       1745                1750                1755

ttc gcc gcc tgc ctg gag ccc tac acc gcc tgc gac ctg gcg ccc ccc     6470
Phe Ala Ala Cys Leu Glu Pro Tyr Thr Ala Cys Asp Leu Ala Pro Pro
   1760                1765                1770

gcc ggc acc acc gac gcc gcg cac ccg ggt taacccgtgg tccccgcgtt      6520
Ala Gly Thr Thr Asp Ala Ala His Pro Gly
1775                1780

gcttcctctg ctggccggga catcaggtgg cccccgctga attggaatcg atattgttac   6580

aacaccccaa catcttcgac gcgggcgtgg caggtcttcc cgacgatgac gccggtgaac   6640

ttcccgccgc cgttgttgtt ttggagcacg gaaagacgat gacggaaaaa gagatcgtgg   6700

attacgtcgc cagtcaagta acaaccgcga aaaagttgcg cggaggagtt gtgtttgtgg   6760

acgaagtacc gaaaggtctt accggaaaac tcgacgcaag aaaaatcaga gagatcctca   6820

taaaggccaa gaagggcgga aagtccaaat tgtaaaatgt aactgtattc agcgatgacg   6880

aaattcttag ctattgtaat actgcgatga gtggcagggc ggggcgtaat ttttttaagg   6940
```

-continued

```
cagttattgg tgcccttaaa cgcctggtgc tacgcctgaa taagtgataa taagcggatg   7000

aatggcagaa attcgccgga tctttgtgaa ggaaccttac ttctgtggtg tgacataatt   7060

ggacaaacta cctacagaga tttaaagctc taaggtaaat ataaaatttt taagtgtata   7120

atgtgttaaa ctactgattc taattgtttg tgtattttag attccaacct atggaactga   7180

tgaatgggag cagtggtgga atgcctttaa tgaggaaaac ctgttttgct cagaagaaat   7240

gccatctagt gatgatgagg ctactgctga ctctcaacat tctactcctc caaaaaagaa   7300

gagaaaggta gaagacccca aggactttcc ttcagaattg ctaagttttt tgagtcatgc   7360

tgtgtttagt aatagaactc ttgcttgctt tgctatttac accacaaagg aaaaagctgc   7420

actgctatac aagaaaatta tggaaaaata ttctgtaacc tttataagta ggcataacag   7480

ttataatcat aacatactgt tttttcttac tccacacagg catagagtgt ctgctattaa   7540

taactatgct caaaaattgt gtacctttag ctttttaatt tgtaaagggg ttaataagga   7600

atatttgatg tatagtgcct tgactagaga tcataatcag ccataccaca tttgtagagg   7660

ttttacttgc tttaaaaaac ctcccacacc tcccccgaa cctgaaacat aaaatgaatg   7720

caattgttgt tgttaacttg tttattgcag cttataatgg ttacaaataa agcaatagca   7780

tcacaaattt cacaaataaa gcattttttt cactgcattc tagttgtggt ttgtccaaac   7840

tcatcaatgt atcttatcat gtctggatcc tctagagtcg acctgcaggc atgcaagctt   7900

ctcgagagta cttctagtgg atccctgcag ctcgagaggc ctaattaatt aagtcgacga   7960

tccggctgct aacaaagccc gaaaggaagc tgagttggct gctgccaccg ctgagcaata   8020

actagcataa ccccttgggg cctctaaacg ggtcttgagg ggttttttgc tgaaaggagg   8080

aactatatcc ggagttaact cgacatatac tatatagtaa taccaatact caagactacg   8140

aaactgatac aatctcttat catgtgggta atgttctcga tgtcgaatag ccatatgccg   8200

gtagttgcga tatacataaa ctgatcacta attccaaacc cacccgcttt ttatagtaag   8260

tttttcaccc ataaataata aatacaataa ttaatttctc gtaaaagtag aaaatatatt   8320

ctaatttatt gcacggtaag gaagtagaat cataaagaac agtgacggat cgatccccca   8380

agcttggaca caagacaggc ttgcgagata tgtttgagaa taccacttta tcccgcgtca   8440

gggagaggca gtgcgtaaaa agacgcggac tcatgtgaaa tactggtttt tagtgcgcca   8500

gatctctata atctcgcgca acctattttc ccctcgaaca ctttttaagc cgtagataaa   8560

caggctggga cacttcac atg agc gaa aaa tac atc gtc acc tgg gac atg    8611
                    Met Ser Glu Lys Tyr Ile Val Thr Trp Asp Met
                   1785                1790                1795

ttg cag atc cat gca cgt aaa ctc gca agc cga ctg atg cct tct gaa    8659
Leu Gln Ile His Ala Arg Lys Leu Ala Ser Arg Leu Met Pro Ser Glu
               1800                1805                1810

caa tgg aaa ggc att att gcc gta agc cgt ggc ggt ctg gta ccg ggt    8707
Gln Trp Lys Gly Ile Ile Ala Val Ser Arg Gly Gly Leu Val Pro Gly
           1815                1820                1825

gcg tta ctg gcg cgt gaa ctg ggt att cgt cat gtc gat acc gtt tgt    8755
Ala Leu Leu Ala Arg Glu Leu Gly Ile Arg His Val Asp Thr Val Cys
       1830                1835                1840

att tcc agc tac gat cac gac aac cag cgc gag ctt aaa gtg ctg aaa    8803
Ile Ser Ser Tyr Asp His Asp Asn Gln Arg Glu Leu Lys Val Leu Lys
   1845                1850                1855

cgc gca gaa ggc gat ggc gaa ggc ttc atc gtt att gat gac ctg gtg    8851
Arg Ala Glu Gly Asp Gly Glu Gly Phe Ile Val Ile Asp Asp Leu Val
1860                1865                1870                1875

gat acc ggt ggt act gcg gtt gcg att cgt gaa atg tat cca aaa gcg    8899
```

-continued

```
Asp Thr Gly Gly Thr Ala Val Ala Ile Arg Glu Met Tyr Pro Lys Ala
               1880                1885                1890

cac ttt gtc acc atc ttc gca aaa ccg gct ggt cgt ccg ctg gtt gat     8947
His Phe Val Thr Ile Phe Ala Lys Pro Ala Gly Arg Pro Leu Val Asp
           1895                1900                1905

gac tat gtt gtt gat atc ccg caa gat acc tgg att gaa cag ccg tgg     8995
Asp Tyr Val Val Asp Ile Pro Gln Asp Thr Trp Ile Glu Gln Pro Trp
       1910                1915                1920

gat atg ggc gtc gta ttc gtc ccg cca atc tcc ggt cgc taatcttttc      9044
Asp Met Gly Val Val Phe Val Pro Pro Ile Ser Gly Arg
   1925                1930                1935

aacgcctggc actgccgggc gttgttcttt ttaacttcag gcgggttaca atagtttcca   9104

gtaagtattc tggaggctgc atccatgaca caggcaaacc tgagcgaaac cctgttcaaa   9164

ccccgcttta aacatcctga aacctcgacg ctagtccgcc gctttaatca cggcgcacaa   9224

ccgcctgtgc agtcggccct tgatggtaaa accatccctc actggtatcg catgattaac   9284

cgtctgatgt ggatctggcg cggcattgac ccacgcgaaa tcctcgacgt ccaggcacgt   9344

attgtgatga gcgatgccga acgtaccgac gatgatttat acgatacggt gattggctac   9404

cgtggcggca actggattta tgagtgggcc ccggatcttt gtgaaggaac cttacttctg   9464

tggtgtgaca taattggaca aactacctac agagatttaa agctctaagg taaatataaa   9524

atttttaagt gtataatgtg ttaaactact gattctaatt gtttgtgtat tttagattcc   9584

aacctatgga actgatgaat gggagcagtg gtggaatgcc tttaatgagg aaaacctgtt   9644

ttgctcagaa gaaatgccat ctagtgatga tgaggctact gctgactctc aacattctac   9704

tcctccaaaa aagaagagaa aggtagaaga ccccaaggac tttccttcag aattgctaag   9764

tttttgagt catgctgtgt ttagtaatag aactcttgct tgctttgcta tttacaccac    9824

aaaggaaaaa gctgcactgc tatacaagaa aattatggaa aaatattctg taacctttat   9884

aagtaggcat aacagttata atcataacat actgtttttt cttactccac acaggcatag   9944

agtgtctgct attaataact atgctcaaaa attgtgtacc tttagctttt taatttgtaa  10004

aggggttaat aaggaatatt tgatgtatag tgccttgact agagatcata atcagccata  10064

ccacatttgt agaggtttta cttgctttaa aaaacctccc acacctcccc ctgaacctga  10124

aacataaaat gaatgcaatt gttgttgtta agcttggggg aattgcatgc tccggatcga  10184

gatcaa ttc tgt gag cgt atg gca aac gaa gga aaa ata gtt ata gta     10232
       Phe Cys Glu Arg Met Ala Asn Glu Gly Lys Ile Val Ile Val
                  1940                1945                1950

gcc gca ctc gat ggg aca ttt caa cgt aaa ccg ttt aat aat att ttg    10280
Ala Ala Leu Asp Gly Thr Phe Gln Arg Lys Pro Phe Asn Asn Ile Leu
               1955                1960                1965

aat ctt att cca tta tct gaa atg gtg gta aaa cta act gct gtg tgt    10328
Asn Leu Ile Pro Leu Ser Glu Met Val Val Lys Leu Thr Ala Val Cys
           1970                1975                1980

atg aaa tgc ttt aag gag gct tcc ttt tct aaa cga ttg ggt gag gaa    10376
Met Lys Cys Phe Lys Glu Ala Ser Phe Ser Lys Arg Leu Gly Glu Glu
       1985                1990                1995

acc gag ata gaa ata ata gga ggt aat gat atg tat caa tcg gtg tgt    10424
Thr Glu Ile Glu Ile Ile Gly Gly Asn Asp Met Tyr Gln Ser Val Cys
   2000                2005                2010

aga aag tgt tac atc gac tca taatattata ttttttatct aaaaaactaa       10475
Arg Lys Cys Tyr Ile Asp Ser
2015                2020

aaataaacat tgattaaatt ttaatataat acttaaaaat ggatgttgtg tcgttagata  10535
```

-continued

```
aaccgtttat gtattttgag gaaattgata atgagttaga ttacgaacca gaaagtgcaa  10595

atgaggtcgc aaaaaaactg ccgtatcaag gacagttaaa actattacta ggagaattat  10655

tttttcttag taagttacag cgacacggta tattagatgg tgccaccgta gtgtatatag  10715

gatctgctcc cggtacacat atacgttatt tgagagatca tttctataat ttaggagtga  10775

tcatcaaatg gatgctaatt gacggccgcc atcatgatcc tattttaaat ggattgcgtg  10835

atgtgactct agtgactcgg ttcgttgatg aggaatatct acgatccatc aaaaaacaac  10895

tgcatccttc taagattatt ttaatttctg atgtgagatc caaacgagga ggaaatgaac  10955

ctagtacggc ggatttacta agtaattacg ctctacaaaa tgtcatgatt agtattttaa  11015

accccgtggc gtctagtctt aaatggagat gcccgtttcc agatcaatgg atcaaggact  11075

tttatatccc acacggtaat aaaatgttac aaccttttgc tccttcatat tcagggccgt  11135

cgttttacaa cgtcgtgact gggaaaaccc tggcgttacc caacttaatc gccttgcagc  11195

acatccccct ttcgccagct ggcgtaatag cgaagaggcc cgcaccgatc gcccttccca  11255

acagttgcgc agcctgaatg gcgaatggcg cgacgcgccc tgtagcggcg cattaagcgc  11315

ggcgggtgtg gtggttacgc gcagcgtgac cgctacactt gccagcgccc tagcgcccgc  11375

tcctttcgct ttcttccctt cctttctcgc cacgttcgcc ggctttcccc gtcaagctct  11435

aaatcggggg ctccctttag ggttccgatt tagtgcttta cggcacctcg accccaaaaa  11495

acttgattag ggtgatggtt cacgtagtgg gccatcgccc tgatagacgg tttttcgccc  11555

tttgacgttg gagtccacgt tctttaatag tggactcttg ttccaaactg gaacaacact  11615

caaccctatc tcggtctatt cttttgattt ataagggatt ttgccgattt cggcctattg  11675

gttaaaaaat gagctgattt aacaaaaatt taacgcgaat tttaacaaaa tattaacgtt  11735

tacaatttcc caggtggcac ttttcgggga aatgtgcgcg gaacccctat ttgtttattt  11795

ttctaaatac attcaaatat gtatccgctc atgagacaat aaccctgata aatgcttcaa  11855

taatattgaa aaaggaagag t atg agt att caa cat ttc cgt gtc gcc ctt    11906
                        Met Ser Ile Gln His Phe Arg Val Ala Leu
                                     2025                2030

att ccc ttt ttt gcg gca ttt tgc ctt cct gtt ttt gct cac cca gaa    11954
Ile Pro Phe Phe Ala Ala Phe Cys Leu Pro Val Phe Ala His Pro Glu
           2035                2040                2045

acg ctg gtg aaa gta aaa gat gct gaa gat cag ttg ggt gca cga gtg    12002
Thr Leu Val Lys Val Lys Asp Ala Glu Asp Gln Leu Gly Ala Arg Val
       2050                2055                2060

ggt tac atc gaa ctg gat ctc aac agc ggt aag atc ctt gag agt ttt    12050
Gly Tyr Ile Glu Leu Asp Leu Asn Ser Gly Lys Ile Leu Glu Ser Phe
   2065                2070                2075

cgc ccc gaa gaa cgt ttt cca atg atg agc act ttt aaa gtt ctg cta    12098
Arg Pro Glu Glu Arg Phe Pro Met Met Ser Thr Phe Lys Val Leu Leu
2080                2085                2090                2095

tgt ggc gcg gta tta tcc cgt att gac gcc ggg caa gag caa ctc ggt    12146
Cys Gly Ala Val Leu Ser Arg Ile Asp Ala Gly Gln Glu Gln Leu Gly
                2100                2105                2110

cgc cgc ata cac tat tct cag aat gac ttg gtt gag tac tca cca gtc    12194
Arg Arg Ile His Tyr Ser Gln Asn Asp Leu Val Glu Tyr Ser Pro Val
           2115                2120                2125

aca gaa aag cat ctt acg gat ggc atg aca gta aga gaa tta tgc agt    12242
Thr Glu Lys His Leu Thr Asp Gly Met Thr Val Arg Glu Leu Cys Ser
       2130                2135                2140

gct gcc ata acc atg agt gat aac act gcg gcc aac tta ctt ctg aca    12290
Ala Ala Ile Thr Met Ser Asp Asn Thr Ala Ala Asn Leu Leu Leu Thr
   2145                2150                2155
```

-continued

```
acg atc gga gga ccg aag gag cta acc gct ttt ttg cac aac atg ggg    12338
Thr Ile Gly Gly Pro Lys Glu Leu Thr Ala Phe Leu His Asn Met Gly
2160                2165                2170                2175

gat cat gta act cgc ctt gat cgt tgg gaa ccg gag ctg aat gaa gcc    12386
Asp His Val Thr Arg Leu Asp Arg Trp Glu Pro Glu Leu Asn Glu Ala
               2180                2185                2190

ata cca aac gac gag cgt gac acc acg atg cct gta gca atg gca aca    12434
Ile Pro Asn Asp Glu Arg Asp Thr Thr Met Pro Val Ala Met Ala Thr
           2195                2200                2205

acg ttg cgc aaa cta tta act ggc gaa cta ctt act cta gct tcc cgg    12482
Thr Leu Arg Lys Leu Leu Thr Gly Glu Leu Leu Thr Leu Ala Ser Arg
       2210                2215                2220

caa caa tta ata gac tgg atg gag gcg gat aaa gtt gca gga cca ctt    12530
Gln Gln Leu Ile Asp Trp Met Glu Ala Asp Lys Val Ala Gly Pro Leu
   2225                2230                2235

ctg cgc tcg gcc ctt ccg gct ggc tgg ttt att gct gat aaa tct gga    12578
Leu Arg Ser Ala Leu Pro Ala Gly Trp Phe Ile Ala Asp Lys Ser Gly
2240                2245                2250                2255

gcc ggt gag cgt ggg tct cgc ggt atc att gca gca ctg ggg cca gat    12626
Ala Gly Glu Arg Gly Ser Arg Gly Ile Ile Ala Ala Leu Gly Pro Asp
               2260                2265                2270

ggt aag ccc tcc cgt atc gta gtt atc tac acg acg ggg agt cag gca    12674
Gly Lys Pro Ser Arg Ile Val Val Ile Tyr Thr Thr Gly Ser Gln Ala
           2275                2280                2285

act atg gat gaa cga aat aga cag atc gct gag ata ggt gcc tca ctg    12722
Thr Met Asp Glu Arg Asn Arg Gln Ile Ala Glu Ile Gly Ala Ser Leu
       2290                2295                2300

att aag cat tgg taactgtcag accaagttta ctcatatata ctttagattg        12774
Ile Lys His Trp
   2305

atttaaaact tcatttttaa tttaaaagga tctaggtgaa gatccttttt gataatctca  12834

tgaccaaaat cccttaacgt gagttttcgt tccactgagc gtcagacccc gtagaaaaga  12894

tcaaaggatc ttcttgagat cctttttttc tgcgcgtaat ctgctgcttg caaacaaaaa  12954

aaccaccgct accagcggtg gtttgtttgc cggatcaaga gctaccaact ctttttccga  13014

aggtaactgg cttcagcaga gcgcagatac caaatactgt ccttctagtg tagccgtagt  13074

taggccacca cttcaagaac tctgtagcac cgcctacata cctcgctctg ctaatcctgt  13134

taccagtggc tgctgccagt ggcgataagt cgtgtcttac cgggttggac tcaagacgat  13194

agttaccgga taaggcgcag cggtcgggct gaacgggggg ttcgtgcaca cagcccagct  13254

tggagcgaac gacctacacc gaactgagat acctacagcg tgagctatga gaaagcgcca  13314

cgcttcccga agggagaaag gcggacaggt atccggtaag cggcagggtc ggaacaggag  13374

agcgcacgag ggagcttcca gggggaaacg cctggtatct ttatagtcct gtcgggtttc  13434

gccacctctg acttgagcgt cgatttttgt gatgctcgtc aggggggcgg agcctatgga  13494

aaaacgccag caacgcggcc tttttacggt tcctggcctt ttgctggcct tttgctcaca  13554

tgttctttcc tgcgttatcc cctgattctg tggataaccg tattaccgcc tttgagtgag  13614

ctgataccgc tcgccgcagc cgaacgaccg agcgcagcga gtcagtgagc gaggaagcgg  13674

aagagcgccc aatacgcaaa ccgcctctcc ccgcgcgttg gccgattcat taatgcagct  13734

ggcacgacag gtttcccgac tggaaagcgg gcagtgagcg caacgcaatt aatgtgagtt  13794

agctcactca ttaggcaccc caggctttac actttatgct tccggctcgt atgttgtgtg  13854

gaattgtgag cggataacaa tttcacacag gaaacagcta tgaccatgat tacgcc      13910
```

-continued

<210> SEQ ID NO 9
<211> LENGTH: 2307
<212> TYPE: PRT
<213> ORGANISM: Artificial Sequence
<220> FEATURE:
<223> OTHER INFORMATION: :

<400> SEQUENCE: 9

Met Asn Gly Gly His Ile Gln Leu Ile Ile Gly Pro Met Phe Ser Gly
1 5 10 15

Lys Ser Thr Glu Leu Ile Arg Arg Val Arg Arg Tyr Gln Ile Ala Gln
20 25 30

Tyr Lys Cys Val Thr Ile Lys Tyr Ser Asn Asp Asn Arg Tyr Gly Thr
35 40 45

Gly Leu Trp Thr His Asp Lys Asn Asn Phe Glu Ala Leu Glu Ala Thr
50 55 60

Lys Leu Cys Asp Val Leu Glu Ser Ile Thr Asp Phe Ser Val Ile Gly
65 70 75 80

Ile Asp Glu Gly Gln Phe Phe Pro Asp Ile Val Glu Met Gly Ile Pro
85 90 95

Gln Phe Met Ala Arg Val Cys Ala Cys Leu Trp Met Met Leu Leu Ile
100 105 110

Ala Gln Ala Glu Ala Ala Leu Glu Asn Leu Val Val Leu Asn Ala Ala
115 120 125

Ser Val Ala Gly Ala His Gly Ile Leu Ser Phe Leu Val Phe Phe Cys
130 135 140

Ala Ala Trp Tyr Ile Lys Gly Arg Leu Val Pro Gly Ala Ala Tyr Ala
145 150 155 160

Leu Tyr Gly Val Trp Pro Leu Leu Leu Leu Leu Leu Ala Leu Pro Pro
165 170 175

Arg Ala Tyr Ala Met Asp Arg Glu Met Ala Ala Ser Cys Gly Gly Ala
180 185 190

Val Phe Val Gly Leu Val Leu Leu Thr Leu Ser Pro Tyr Tyr Lys Val
195 200 205

Phe Leu Ala Arg Leu Ile Trp Trp Leu Gln Tyr Phe Thr Thr Arg Ala
210 215 220

Glu Ala His Leu His Val Trp Ile Pro Pro Leu Asn Ala Arg Gly Gly
225 230 235 240

Arg Asp Ala Ile Ile Leu Leu Met Cys Ala Val His Pro Glu Leu Ile
245 250 255

Phe Asp Ile Thr Lys Leu Leu Ile Ala Ile Leu Gly Pro Leu Met Val
260 265 270

Leu Gln Ala Gly Ile Thr Arg Val Pro Tyr Phe Val Arg Ala Gln Gly
275 280 285

Leu Ile His Ala Cys Met Leu Val Arg Lys Val Ala Gly Gly His Tyr
290 295 300

Val Gln Met Ala Phe Met Lys Leu Gly Ala Leu Thr Gly Thr Tyr Ile
305 310 315 320

Tyr Asn His Leu Thr Pro Leu Arg Asp Trp Ala His Ala Gly Leu Arg
325 330 335

Asp Leu Ala Val Ala Val Glu Pro Val Val Phe Ser Asp Met Glu Thr
340 345 350

Lys Ile Ile Thr Trp Gly Ala Asp Thr Ala Ala Cys Gly Asp Ile Ile
355 360 365

-continued

```
Leu Gly Leu Pro Val Ser Ala Arg Arg Gly Lys Glu Ile Leu Leu Gly
    370                 375                 380

Pro Ala Asp Ser Leu Glu Gly Arg Gly Trp Arg Leu Leu Ala Pro Ile
385                 390                 395                 400

Thr Ala Tyr Ser Gln Gln Thr Arg Gly Leu Leu Gly Cys Ile Ile Thr
                405                 410                 415

Ser Leu Thr Gly Arg Asp Lys Asn Gln Val Glu Gly Glu Val Gln Val
            420                 425                 430

Val Ser Thr Ala Thr Gln Ser Phe Leu Ala Thr Cys Val Asn Gly Val
        435                 440                 445

Cys Trp Thr Val Tyr His Gly Ala Gly Ser Lys Thr Leu Ala Gly Pro
    450                 455                 460

Lys Gly Pro Ile Thr Gln Met Tyr Thr Asn Val Asp Gln Asp Leu Val
465                 470                 475                 480

Gly Trp Gln Ala Pro Pro Gly Ala Arg Ser Leu Thr Pro Cys Thr Cys
                485                 490                 495

Gly Ser Ser Asp Leu Tyr Leu Val Thr Arg His Ala Asp Val Ile Pro
            500                 505                 510

Val Arg Arg Arg Gly Asp Ser Arg Gly Ser Leu Leu Ser Pro Arg Pro
        515                 520                 525

Val Ser Tyr Leu Lys Gly Ser Ala Gly Gly Pro Leu Leu Cys Pro Ser
    530                 535                 540

Gly His Ala Val Gly Ile Phe Arg Ala Ala Val Cys Thr Arg Gly Val
545                 550                 555                 560

Ala Lys Ala Val Asp Phe Val Pro Val Glu Ser Met Glu Thr Thr Met
                565                 570                 575

Arg Ser Pro Val Phe Thr Asp Asn Ser Ser Pro Pro Ala Val Pro Gln
            580                 585                 590

Ser Phe Gln Val Ala His Leu His Ala Pro Thr Gly Ser Gly Lys Ser
        595                 600                 605

Thr Lys Val Pro Ala Ala Tyr Ala Ala Gln Gly Tyr Lys Val Leu Val
    610                 615                 620

Leu Asn Pro Ser Val Ala Ala Thr Leu Gly Phe Gly Ala Tyr Met Ser
625                 630                 635                 640

Lys Ala His Gly Ile Asp Pro Asn Ile Arg Thr Gly Val Arg Thr Ile
                645                 650                 655

Thr Thr Gly Ala Pro Val Thr Tyr Ser Thr Tyr Gly Lys Phe Leu Ala
            660                 665                 670

Asp Gly Gly Cys Ser Gly Gly Ala Tyr Asp Ile Ile Ile Cys Asp Glu
        675                 680                 685

Cys His Ser Thr Asp Ser Thr Thr Ile Leu Gly Ile Gly Thr Val Leu
    690                 695                 700

Asp Gln Ala Glu Thr Ala Gly Ala Arg Leu Val Val Leu Ala Thr Ala
705                 710                 715                 720

Thr Pro Pro Gly Ser Val Thr Val Pro His Pro Asn Ile Glu Glu Val
                725                 730                 735

Ala Leu Ser Asn Thr Gly Glu Ile Pro Phe Tyr Gly Lys Ala Ile Pro
            740                 745                 750

Ile Glu Ala Ile Arg Gly Gly Arg His Leu Ile Phe Cys His Ser Lys
        755                 760                 765

Lys Lys Cys Asp Glu Leu Ala Ala Lys Leu Ser Gly Leu Gly Ile Asn
    770                 775                 780

Ala Val Ala Tyr Tyr Arg Gly Leu Asp Val Ser Val Ile Pro Thr Ile
```

-continued

```
785                 790                 795                 800

Gly Asp Val Val Val Val Ala Thr Asp Ala Leu Met Thr Gly Tyr Thr
                805                 810                 815

Gly Asp Phe Asp Ser Val Ile Asp Cys Asn Thr Cys Val Thr Gln Thr
            820                 825                 830

Val Asp Phe Ser Leu Asp Pro Thr Phe Thr Ile Glu Thr Thr Thr Val
        835                 840                 845

Pro Gln Asp Ala Val Ser Arg Ser Gln Arg Arg Gly Arg Thr Gly Arg
    850                 855                 860

Gly Arg Arg Gly Ile Tyr Arg Phe Val Thr Pro Gly Glu Arg Pro Ser
865                 870                 875                 880

Gly Met Phe Asp Ser Ser Val Leu Cys Glu Cys Tyr Asp Ala Gly Cys
                885                 890                 895

Ala Trp Tyr Glu Leu Thr Pro Ala Glu Thr Ser Val Arg Leu Arg Ala
            900                 905                 910

Tyr Leu Asn Thr Pro Gly Leu Pro Val Cys Gln Asp His Leu Glu Phe
        915                 920                 925

Trp Glu Ser Val Phe Thr Gly Leu Thr His Ile Asp Ala His Phe Leu
    930                 935                 940

Ser Gln Thr Lys Gln Ala Gly Asp Asn Phe Pro Tyr Leu Val Ala Tyr
945                 950                 955                 960

Gln Ala Thr Val Cys Ala Arg Ala Gln Ala Pro Pro Pro Ser Trp Asp
                965                 970                 975

Gln Met Trp Lys Cys Leu Ile Arg Leu Lys Pro Thr Leu His Gly Pro
            980                 985                 990

Thr Pro Leu Leu Tyr Arg Leu Gly Ala Val Gln Asn Glu Val Thr Leu
        995                 1000                1005

Thr His Pro Ile Thr Lys Tyr Ile Met Ala Cys Met Ser Ala Asp Leu
   1010                 1015                1020

Glu Val Val Thr Ser Thr Trp Val Leu Val Gly Gly Val Leu Ala Ala
1025                1030                1035                1040

Leu Ala Ala Tyr Cys Leu Thr Thr Gly Ser Val Val Ile Val Gly Arg
               1045                1050                1055

Ile Ile Leu Ser Gly Arg Pro Ala Ile Val Pro Asp Arg Glu Leu Leu
           1060                1065                1070

Tyr Gln Glu Phe Asp Glu Met Glu Glu Cys Ala Ser His Leu Pro Tyr
       1075                1080                1085

Ile Glu Gln Gly Met Gln Leu Ala Glu Gln Phe Lys Gln Lys Ala Leu
   1090                1095                1100

Gly Leu Leu Gln Thr Ala Thr Lys Gln Ala Glu Ala Ala Ala Pro Val
1105                1110                1115                1120

Val Glu Ser Lys Trp Arg Ala Leu Glu Thr Phe Trp Ala Lys His Met
               1125                1130                1135

Trp Asn Phe Ile Ser Gly Ile Gln Tyr Leu Ala Gly Leu Ser Thr Leu
           1140                1145                1150

Pro Gly Asn Pro Ala Ile Ala Ser Leu Met Ala Phe Thr Ala Ser Ile
       1155                1160                1165

Thr Ser Pro Leu Thr Thr Gln Ser Thr Leu Leu Phe Asn Ile Leu Gly
   1170                1175                1180

Gly Trp Val Ala Ala Gln Leu Ala Pro Pro Ser Ala Ala Ser Ala Phe
1185                1190                1195                1200

Val Gly Ala Gly Ile Ala Gly Ala Ala Val Gly Ser Ile Gly Leu Gly
               1205                1210                1215
```

-continued

```
Lys Val Leu Val Asp Ile Leu Ala Gly Tyr Gly Ala Gly Val Ala Gly
            1220                1225                1230

Ala Leu Val Ala Phe Lys Val Met Ser Gly Glu Met Pro Ser Thr Glu
        1235                1240                1245

Asp Leu Val Asn Leu Leu Pro Ala Ile Leu Glu Glu Ala Ser Glu Asp
    1250                1255                1260

Val Val Cys Cys Ser Met Ser Tyr Thr Trp Thr Gly Ala Leu Glu Leu
1265                1270                1275                1280

Leu Leu Leu Leu Leu Leu Gly Leu Arg Leu Gln Leu Ser Leu Gly Ile
                1285                1290                    1295

Ile Pro Val Glu Glu Glu Asn Pro Asp Phe Trp Asn Arg Glu Ala Ala
            1300                1305                1310

Glu Ala Leu Gly Ala Ala Lys Lys Leu Gln Pro Ala Gln Thr Ala Ala
        1315                1320                1325

Lys Asn Leu Ile Ile Phe Leu Gly Asp Gly Met Gly Val Ser Thr Val
    1330                1335                1340

Thr Ala Ala Arg Ile Leu Lys Gly Gln Lys Lys Asp Lys Leu Gly Pro
1345                1350                1355                1360

Glu Ile Pro Leu Ala Met Asp Arg Phe Pro Tyr Val Ala Leu Ser Lys
                1365                1370                    1375

Thr Tyr Asn Val Asp Lys His Val Pro Asp Ser Gly Ala Thr Ala Thr
            1380                1385                1390

Ala Tyr Leu Cys Gly Val Lys Gly Asn Phe Gln Thr Ile Gly Leu Ser
        1395                1400                1405

Ala Ala Ala Arg Phe Asn Gln Cys Asn Thr Thr Arg Gly Asn Glu Val
    1410                1415                1420

Ile Ser Val Met Asn Arg Ala Lys Lys Ala Gly Lys Ser Val Gly Val
1425                1430                1435                1440

Val Thr Thr Thr Arg Val Gln His Ala Ser Pro Ala Gly Thr Tyr Ala
                1445                1450                    1455

His Thr Val Asn Arg Asn Trp Tyr Ser Asp Ala Asp Val Pro Ala Ser
            1460                1465                1470

Ala Arg Gln Glu Gly Cys Gln Asp Ile Ala Thr Gln Leu Ile Ser Asn
        1475                1480                1485

Met Asp Ile Asp Val Ile Leu Gly Gly Gly Arg Lys Tyr Met Phe Pro
    1490                1495                1500

Met Gly Thr Pro Asp Pro Glu Tyr Pro Asp Asp Tyr Ser Gln Gly Gly
1505                1510                1515                1520

Thr Arg Leu Asp Gly Lys Asn Leu Val Gln Glu Trp Leu Ala Lys Arg
                1525                1530                    1535

Gln Gly Ala Arg Tyr Val Trp Asn Arg Thr Glu Leu Met Gln Ala Ser
            1540                1545                1550

Leu Asp Pro Ser Val Thr His Leu Met Gly Leu Phe Glu Pro Gly Asp
        1555                1560                1565

Met Lys Tyr Glu Ile His Arg Asp Ser Thr Leu Asp Pro Ser Leu Met
    1570                1575                1580

Glu Met Thr Glu Ala Ala Leu Arg Leu Leu Ser Arg Asn Pro Arg Gly
1585                1590                1595                1600

Phe Phe Leu Phe Val Glu Gly Gly Arg Ile Asp His Gly His His Glu
                1605                1610                    1615

Ser Arg Ala Tyr Arg Ala Leu Thr Glu Thr Ile Met Phe Asp Asp Ala
            1620                1625                1630
```

-continued

```
Ile Glu Arg Ala Gly Gln Leu Thr Ser Glu Glu Asp Thr Leu Ser Leu
      1635                1640                1645

Val Thr Ala Asp His Ser His Val Phe Ser Phe Gly Gly Tyr Pro Leu
   1650                1655                1660

Arg Gly Ser Cys Ile Phe Gly Leu Ala Pro Gly Lys Ala Arg Asp Arg
1665                1670                1675                1680

Lys Ala Tyr Thr Val Leu Leu Tyr Gly Asn Gly Pro Gly Tyr Val Leu
               1685                1690                1695

Lys Asp Gly Ala Arg Pro Asp Val Thr Glu Ser Glu Ser Gly Ser Pro
           1700                1705                1710

Glu Tyr Arg Gln Gln Ser Ala Val Pro Leu Asp Glu Glu Thr His Ala
      1715                1720                1725

Gly Glu Asp Val Ala Val Phe Ala Arg Gly Pro Gln Ala His Leu Val
   1730                1735                1740

His Gly Val Gln Glu Gln Thr Phe Ile Ala His Val Met Ala Phe Ala
1745                1750                1755                1760

Ala Cys Leu Glu Pro Tyr Thr Ala Cys Asp Leu Ala Pro Pro Ala Gly
               1765                1770                1775

Thr Thr Asp Ala Ala His Pro Gly Met Ser Glu Lys Tyr Ile Val Thr
           1780                1785                1790

Trp Asp Met Leu Gln Ile His Ala Arg Lys Leu Ala Ser Arg Leu Met
      1795                1800                1805

Pro Ser Glu Gln Trp Lys Gly Ile Ile Ala Val Ser Arg Gly Gly Leu
   1810                1815                1820

Val Pro Gly Ala Leu Leu Ala Arg Glu Leu Gly Ile Arg His Val Asp
1825                1830                1835                1840

Thr Val Cys Ile Ser Ser Tyr Asp His Asp Asn Gln Arg Glu Leu Lys
               1845                1850                1855

Val Leu Lys Arg Ala Glu Gly Asp Gly Glu Gly Phe Ile Val Ile Asp
           1860                1865                1870

Asp Leu Val Asp Thr Gly Gly Thr Ala Val Ala Ile Arg Glu Met Tyr
      1875                1880                1885

Pro Lys Ala His Phe Val Thr Ile Phe Ala Lys Pro Ala Gly Arg Pro
   1890                1895                1900

Leu Val Asp Asp Tyr Val Val Asp Ile Pro Gln Asp Thr Trp Ile Glu
1905                1910                1915                1920

Gln Pro Trp Asp Met Gly Val Val Phe Val Pro Pro Ile Ser Gly Arg
               1925                1930                1935

Phe Cys Glu Arg Met Ala Asn Glu Gly Lys Ile Val Ile Val Ala Ala
           1940                1945                1950

Leu Asp Gly Thr Phe Gln Arg Lys Pro Phe Asn Asn Ile Leu Asn Leu
      1955                1960                1965

Ile Pro Leu Ser Glu Met Val Val Lys Leu Thr Ala Val Cys Met Lys
   1970                1975                1980

Cys Phe Lys Glu Ala Ser Phe Ser Lys Arg Leu Gly Glu Glu Thr Glu
1985                1990                1995                2000

Ile Glu Ile Ile Gly Gly Asn Asp Met Tyr Gln Ser Val Cys Arg Lys
               2005                2010                2015

Cys Tyr Ile Asp Ser Met Ser Ile Gln His Phe Arg Val Ala Leu Ile
           2020                2025                2030

Pro Phe Phe Ala Ala Phe Cys Leu Pro Val Phe Ala His Pro Glu Thr
      2035                2040                2045

Leu Val Lys Val Lys Asp Ala Glu Asp Gln Leu Gly Ala Arg Val Gly
```

-continued

```
   2050                2055                2060

Tyr Ile Glu Leu Asp Leu Asn Ser Gly Lys Ile Leu Glu Ser Phe Arg
2065                2070                2075                2080

Pro Glu Glu Arg Phe Pro Met Met Ser Thr Phe Lys Val Leu Leu Cys
               2085                2090                2095

Gly Ala Val Leu Ser Arg Ile Asp Ala Gly Gln Glu Gln Leu Gly Arg
           2100                2105                2110

Arg Ile His Tyr Ser Gln Asn Asp Leu Val Glu Tyr Ser Pro Val Thr
       2115                2120                2125

Glu Lys His Leu Thr Asp Gly Met Thr Val Arg Glu Leu Cys Ser Ala
   2130                2135                2140

Ala Ile Thr Met Ser Asp Asn Thr Ala Ala Asn Leu Leu Leu Thr Thr
2145                2150                2155                2160

Ile Gly Gly Pro Lys Glu Leu Thr Ala Phe Leu His Asn Met Gly Asp
               2165                2170                2175

His Val Thr Arg Leu Asp Arg Trp Glu Pro Glu Leu Asn Glu Ala Ile
           2180                2185                2190

Pro Asn Asp Glu Arg Asp Thr Thr Met Pro Val Ala Met Ala Thr Thr
       2195                2200                2205

Leu Arg Lys Leu Leu Thr Gly Glu Leu Leu Thr Leu Ala Ser Arg Gln
   2210                2215                2220

Gln Leu Ile Asp Trp Met Glu Ala Asp Lys Val Ala Gly Pro Leu Leu
2225                2230                2235                2240

Arg Ser Ala Leu Pro Ala Gly Trp Phe Ile Ala Asp Lys Ser Gly Ala
               2245                2250                2255

Gly Glu Arg Gly Ser Arg Gly Ile Ile Ala Ala Leu Gly Pro Asp Gly
           2260                2265                2270

Lys Pro Ser Arg Ile Val Val Ile Tyr Thr Thr Gly Ser Gln Ala Thr
       2275                2280                2285

Met Asp Glu Arg Asn Arg Gln Ile Ala Glu Ile Gly Ala Ser Leu Ile
   2290                2295                2300

Lys His Trp
2305


<210> SEQ ID NO 10
<211> LENGTH: 92
<212> TYPE: PRT
<213> ORGANISM: Artificial Sequence
<220> FEATURE:
<223> OTHER INFORMATION: :

<400> SEQUENCE: 10

Met Asn Gly Gly His Ile Gln Leu Ile Ile Gly Pro Met Phe Ser Gly
  1               5                  10                  15

Lys Ser Thr Glu Leu Ile Arg Arg Val Arg Arg Tyr Gln Ile Ala Gln
             20                  25                  30

Tyr Lys Cys Val Thr Ile Lys Tyr Ser Asn Asp Asn Arg Tyr Gly Thr
         35                  40                  45

Gly Leu Trp Thr His Asp Lys Asn Asn Phe Glu Ala Leu Glu Ala Thr
     50                  55                  60

Lys Leu Cys Asp Val Leu Glu Ser Ile Thr Asp Phe Ser Val Ile Gly
 65                  70                  75                  80

Ile Asp Glu Gly Gln Phe Phe Pro Asp Ile Val Glu
                 85                  90
```

-continued

```
<210> SEQ ID NO 11
<211> LENGTH: 1692
<212> TYPE: PRT
<213> ORGANISM: Artificial Sequence
<220> FEATURE:
<223> OTHER INFORMATION: :

<400> SEQUENCE: 11

Met Gly Ile Pro Gln Phe Met Ala Arg Val Cys Ala Cys Leu Trp Met
  1               5                  10                  15

Met Leu Leu Ile Ala Gln Ala Glu Ala Ala Leu Glu Asn Leu Val Val
             20                  25                  30

Leu Asn Ala Ala Ser Val Ala Gly Ala His Gly Ile Leu Ser Phe Leu
         35                  40                  45

Val Phe Phe Cys Ala Ala Trp Tyr Ile Lys Gly Arg Leu Val Pro Gly
     50                  55                  60

Ala Ala Tyr Ala Leu Tyr Gly Val Trp Pro Leu Leu Leu Leu Leu Leu
 65                  70                  75                  80

Ala Leu Pro Pro Arg Ala Tyr Ala Met Asp Arg Glu Met Ala Ala Ser
                 85                  90                  95

Cys Gly Gly Ala Val Phe Val Gly Leu Val Leu Leu Thr Leu Ser Pro
            100                 105                 110

Tyr Tyr Lys Val Phe Leu Ala Arg Leu Ile Trp Trp Leu Gln Tyr Phe
        115                 120                 125

Thr Thr Arg Ala Glu Ala His Leu His Val Trp Ile Pro Pro Leu Asn
    130                 135                 140

Ala Arg Gly Gly Arg Asp Ala Ile Ile Leu Leu Met Cys Ala Val His
145                 150                 155                 160

Pro Glu Leu Ile Phe Asp Ile Thr Lys Leu Leu Ile Ala Ile Leu Gly
                165                 170                 175

Pro Leu Met Val Leu Gln Ala Gly Ile Thr Arg Val Pro Tyr Phe Val
            180                 185                 190

Arg Ala Gln Gly Leu Ile His Ala Cys Met Leu Val Arg Lys Val Ala
        195                 200                 205

Gly Gly His Tyr Val Gln Met Ala Phe Met Lys Leu Gly Ala Leu Thr
    210                 215                 220

Gly Thr Tyr Ile Tyr Asn His Leu Thr Pro Leu Arg Asp Trp Ala His
225                 230                 235                 240

Ala Gly Leu Arg Asp Leu Ala Val Ala Val Glu Pro Val Val Phe Ser
                245                 250                 255

Asp Met Glu Thr Lys Ile Ile Thr Trp Gly Ala Asp Thr Ala Ala Cys
            260                 265                 270

Gly Asp Ile Ile Leu Gly Leu Pro Val Ser Ala Arg Arg Gly Lys Glu
        275                 280                 285

Ile Leu Leu Gly Pro Ala Asp Ser Leu Glu Gly Arg Gly Trp Arg Leu
    290                 295                 300

Leu Ala Pro Ile Thr Ala Tyr Ser Gln Gln Thr Arg Gly Leu Leu Gly
305                 310                 315                 320

Cys Ile Ile Thr Ser Leu Thr Gly Arg Asp Lys Asn Gln Val Glu Gly
                325                 330                 335

Glu Val Gln Val Val Ser Thr Ala Thr Gln Ser Phe Leu Ala Thr Cys
            340                 345                 350

Val Asn Gly Val Cys Trp Thr Val Tyr His Gly Ala Gly Ser Lys Thr
        355                 360                 365

Leu Ala Gly Pro Lys Gly Pro Ile Thr Gln Met Tyr Thr Asn Val Asp
```

-continued

```
    370                 375                 380

Gln Asp Leu Val Gly Trp Gln Ala Pro Pro Gly Ala Arg Ser Leu Thr
385                 390                 395                 400

Pro Cys Thr Cys Gly Ser Ser Asp Leu Tyr Leu Val Thr Arg His Ala
                405                 410                 415

Asp Val Ile Pro Val Arg Arg Arg Gly Asp Ser Arg Gly Ser Leu Leu
            420                 425                 430

Ser Pro Arg Pro Val Ser Tyr Leu Lys Gly Ser Ala Gly Gly Pro Leu
        435                 440                 445

Leu Cys Pro Ser Gly His Ala Val Gly Ile Phe Arg Ala Ala Val Cys
    450                 455                 460

Thr Arg Gly Val Ala Lys Ala Val Asp Phe Val Pro Val Glu Ser Met
465                 470                 475                 480

Glu Thr Thr Met Arg Ser Pro Val Phe Thr Asp Asn Ser Ser Pro Pro
                485                 490                 495

Ala Val Pro Gln Ser Phe Gln Val Ala His Leu His Ala Pro Thr Gly
            500                 505                 510

Ser Gly Lys Ser Thr Lys Val Pro Ala Ala Tyr Ala Ala Gln Gly Tyr
        515                 520                 525

Lys Val Leu Val Leu Asn Pro Ser Val Ala Ala Thr Leu Gly Phe Gly
    530                 535                 540

Ala Tyr Met Ser Lys Ala His Gly Ile Asp Pro Asn Ile Arg Thr Gly
545                 550                 555                 560

Val Arg Thr Ile Thr Thr Gly Ala Pro Val Thr Tyr Ser Thr Tyr Gly
                565                 570                 575

Lys Phe Leu Ala Asp Gly Gly Cys Ser Gly Gly Ala Tyr Asp Ile Ile
            580                 585                 590

Ile Cys Asp Glu Cys His Ser Thr Asp Ser Thr Thr Ile Leu Gly Ile
        595                 600                 605

Gly Thr Val Leu Asp Gln Ala Glu Thr Ala Gly Ala Arg Leu Val Val
    610                 615                 620

Leu Ala Thr Ala Thr Pro Pro Gly Ser Val Thr Val Pro His Pro Asn
625                 630                 635                 640

Ile Glu Glu Val Ala Leu Ser Asn Thr Gly Glu Ile Pro Phe Tyr Gly
                645                 650                 655

Lys Ala Ile Pro Ile Glu Ala Ile Arg Gly Gly Arg His Leu Ile Phe
            660                 665                 670

Cys His Ser Lys Lys Lys Cys Asp Glu Leu Ala Ala Lys Leu Ser Gly
        675                 680                 685

Leu Gly Ile Asn Ala Val Ala Tyr Tyr Arg Gly Leu Asp Val Ser Val
    690                 695                 700

Ile Pro Thr Ile Gly Asp Val Val Val Val Ala Thr Asp Ala Leu Met
705                 710                 715                 720

Thr Gly Tyr Thr Gly Asp Phe Asp Ser Val Ile Asp Cys Asn Thr Cys
                725                 730                 735

Val Thr Gln Thr Val Asp Phe Ser Leu Asp Pro Thr Phe Thr Ile Glu
            740                 745                 750

Thr Thr Thr Val Pro Gln Asp Ala Val Ser Arg Ser Gln Arg Arg Gly
        755                 760                 765

Arg Thr Gly Arg Gly Arg Arg Gly Ile Tyr Arg Phe Val Thr Pro Gly
    770                 775                 780

Glu Arg Pro Ser Gly Met Phe Asp Ser Ser Val Leu Cys Glu Cys Tyr
785                 790                 795                 800
```

-continued

```
Asp Ala Gly Cys Ala Trp Tyr Glu Leu Thr Pro Ala Glu Thr Ser Val
                805                 810                 815

Arg Leu Arg Ala Tyr Leu Asn Thr Pro Gly Leu Pro Val Cys Gln Asp
            820                 825                 830

His Leu Glu Phe Trp Glu Ser Val Phe Thr Gly Leu Thr His Ile Asp
        835                 840                 845

Ala His Phe Leu Ser Gln Thr Lys Gln Ala Gly Asp Asn Phe Pro Tyr
    850                 855                 860

Leu Val Ala Tyr Gln Ala Thr Val Cys Ala Arg Ala Gln Ala Pro Pro
865                 870                 875                 880

Pro Ser Trp Asp Gln Met Trp Lys Cys Leu Ile Arg Leu Lys Pro Thr
                885                 890                 895

Leu His Gly Pro Thr Pro Leu Leu Tyr Arg Leu Gly Ala Val Gln Asn
            900                 905                 910

Glu Val Thr Leu Thr His Pro Ile Thr Lys Tyr Ile Met Ala Cys Met
        915                 920                 925

Ser Ala Asp Leu Glu Val Val Thr Ser Thr Trp Val Leu Val Gly Gly
    930                 935                 940

Val Leu Ala Ala Leu Ala Ala Tyr Cys Leu Thr Thr Gly Ser Val Val
945                 950                 955                 960

Ile Val Gly Arg Ile Ile Leu Ser Gly Arg Pro Ala Ile Val Pro Asp
                965                 970                 975

Arg Glu Leu Leu Tyr Gln Glu Phe Asp Glu Met Glu Glu Cys Ala Ser
            980                 985                 990

His Leu Pro Tyr Ile Glu Gln Gly Met Gln Leu Ala Glu Gln Phe Lys
        995                 1000                1005

Gln Lys Ala Leu Gly Leu Leu Gln Thr Ala Thr Lys Gln Ala Glu Ala
   1010                1015                1020

Ala Ala Pro Val Val Glu Ser Lys Trp Arg Ala Leu Glu Thr Phe Trp
1025                1030                1035                1040

Ala Lys His Met Trp Asn Phe Ile Ser Gly Ile Gln Tyr Leu Ala Gly
               1045                1050                1055

Leu Ser Thr Leu Pro Gly Asn Pro Ala Ile Ala Ser Leu Met Ala Phe
           1060                1065                1070

Thr Ala Ser Ile Thr Ser Pro Leu Thr Thr Gln Ser Thr Leu Leu Phe
       1075                1080                1085

Asn Ile Leu Gly Gly Trp Val Ala Ala Gln Leu Ala Pro Pro Ser Ala
   1090                1095                1100

Ala Ser Ala Phe Val Gly Ala Gly Ile Ala Gly Ala Ala Val Gly Ser
1105                1110                1115                1120

Ile Gly Leu Gly Lys Val Leu Val Asp Ile Leu Ala Gly Tyr Gly Ala
               1125                1130                1135

Gly Val Ala Gly Ala Leu Val Ala Phe Lys Val Met Ser Gly Glu Met
           1140                1145                1150

Pro Ser Thr Glu Asp Leu Val Asn Leu Leu Pro Ala Ile Leu Glu Glu
       1155                1160                1165

Ala Ser Glu Asp Val Val Cys Cys Ser Met Ser Tyr Thr Trp Thr Gly
   1170                1175                1180

Ala Leu Glu Leu Leu Leu Leu Leu Leu Leu Gly Leu Arg Leu Gln Leu
1185                1190                1195                1200

Ser Leu Gly Ile Ile Pro Val Glu Glu Glu Asn Pro Asp Phe Trp Asn
               1205                1210                1215
```

-continued

```
Arg Glu Ala Ala Glu Ala Leu Gly Ala Ala Lys Lys Leu Gln Pro Ala
            1220                1225                1230

Gln Thr Ala Ala Lys Asn Leu Ile Ile Phe Leu Gly Asp Gly Met Gly
        1235                1240                1245

Val Ser Thr Val Thr Ala Ala Arg Ile Leu Lys Gly Gln Lys Lys Asp
    1250                1255                1260

Lys Leu Gly Pro Glu Ile Pro Leu Ala Met Asp Arg Phe Pro Tyr Val
1265                1270                1275                1280

Ala Leu Ser Lys Thr Tyr Asn Val Asp Lys His Val Pro Asp Ser Gly
                1285                1290                1295

Ala Thr Ala Thr Ala Tyr Leu Cys Gly Val Lys Gly Asn Phe Gln Thr
            1300                1305                1310

Ile Gly Leu Ser Ala Ala Ala Arg Phe Asn Gln Cys Asn Thr Thr Arg
        1315                1320                1325

Gly Asn Glu Val Ile Ser Val Met Asn Arg Ala Lys Lys Ala Gly Lys
    1330                1335                1340

Ser Val Gly Val Val Thr Thr Thr Arg Val Gln His Ala Ser Pro Ala
1345                1350                1355                1360

Gly Thr Tyr Ala His Thr Val Asn Arg Asn Trp Tyr Ser Asp Ala Asp
                1365                1370                1375

Val Pro Ala Ser Ala Arg Gln Glu Gly Cys Gln Asp Ile Ala Thr Gln
            1380                1385                1390

Leu Ile Ser Asn Met Asp Ile Asp Val Ile Leu Gly Gly Gly Arg Lys
        1395                1400                1405

Tyr Met Phe Pro Met Gly Thr Pro Asp Pro Glu Tyr Pro Asp Asp Tyr
    1410                1415                1420

Ser Gln Gly Gly Thr Arg Leu Asp Gly Lys Asn Leu Val Gln Glu Trp
1425                1430                1435                1440

Leu Ala Lys Arg Gln Gly Ala Arg Tyr Val Trp Asn Arg Thr Glu Leu
                1445                1450                1455

Met Gln Ala Ser Leu Asp Pro Ser Val Thr His Leu Met Gly Leu Phe
            1460                1465                1470

Glu Pro Gly Asp Met Lys Tyr Glu Ile His Arg Asp Ser Thr Leu Asp
        1475                1480                1485

Pro Ser Leu Met Glu Met Thr Glu Ala Ala Leu Arg Leu Leu Ser Arg
    1490                1495                1500

Asn Pro Arg Gly Phe Phe Leu Phe Val Glu Gly Gly Arg Ile Asp His
1505                1510                1515                1520

Gly His His Glu Ser Arg Ala Tyr Arg Ala Leu Thr Glu Thr Ile Met
                1525                1530                1535

Phe Asp Asp Ala Ile Glu Arg Ala Gly Gln Leu Thr Ser Glu Glu Asp
            1540                1545                1550

Thr Leu Ser Leu Val Thr Ala Asp His Ser His Val Phe Ser Phe Gly
        1555                1560                1565

Gly Tyr Pro Leu Arg Gly Ser Cys Ile Phe Gly Leu Ala Pro Gly Lys
    1570                1575                1580

Ala Arg Asp Arg Lys Ala Tyr Thr Val Leu Leu Tyr Gly Asn Gly Pro
1585                1590                1595                1600

Gly Tyr Val Leu Lys Asp Gly Ala Arg Pro Asp Val Thr Glu Ser Glu
                1605                1610                1615

Ser Gly Ser Pro Glu Tyr Arg Gln Gln Ser Ala Val Pro Leu Asp Glu
            1620                1625                1630

Glu Thr His Ala Gly Glu Asp Val Ala Val Phe Ala Arg Gly Pro Gln
```

```
        1635                1640                1645

Ala His Leu Val His Gly Val Gln Glu Gln Thr Phe Ile Ala His Val
    1650                1655                1660

Met Ala Phe Ala Ala Cys Leu Glu Pro Tyr Thr Ala Cys Asp Leu Ala
1665                1670                1675                1680

Pro Pro Ala Gly Thr Thr Asp Ala Ala His Pro Gly
                1685                1690


<210> SEQ ID NO 12
<211> LENGTH: 152
<212> TYPE: PRT
<213> ORGANISM: Artificial Sequence
<220> FEATURE:
<223> OTHER INFORMATION: :

<400> SEQUENCE: 12

Met Ser Glu Lys Tyr Ile Val Thr Trp Asp Met Leu Gln Ile His Ala
  1               5                  10                  15

Arg Lys Leu Ala Ser Arg Leu Met Pro Ser Glu Gln Trp Lys Gly Ile
             20                  25                  30

Ile Ala Val Ser Arg Gly Gly Leu Val Pro Gly Ala Leu Leu Ala Arg
         35                  40                  45

Glu Leu Gly Ile Arg His Val Asp Thr Val Cys Ile Ser Ser Tyr Asp
     50                  55                  60

His Asp Asn Gln Arg Glu Leu Lys Val Leu Lys Arg Ala Glu Gly Asp
 65                  70                  75                  80

Gly Glu Gly Phe Ile Val Ile Asp Asp Leu Val Asp Thr Gly Gly Thr
                 85                  90                  95

Ala Val Ala Ile Arg Glu Met Tyr Pro Lys Ala His Phe Val Thr Ile
            100                 105                 110

Phe Ala Lys Pro Ala Gly Arg Pro Leu Val Asp Asp Tyr Val Val Asp
        115                 120                 125

Ile Pro Gln Asp Thr Trp Ile Glu Gln Pro Trp Asp Met Gly Val Val
    130                 135                 140

Phe Val Pro Pro Ile Ser Gly Arg
145                 150


<210> SEQ ID NO 13
<211> LENGTH: 85
<212> TYPE: PRT
<213> ORGANISM: Artificial Sequence
<220> FEATURE:
<223> OTHER INFORMATION: :

<400> SEQUENCE: 13

Phe Cys Glu Arg Met Ala Asn Glu Gly Lys Ile Val Ile Val Ala Ala
  1               5                  10                  15

Leu Asp Gly Thr Phe Gln Arg Lys Pro Phe Asn Asn Ile Leu Asn Leu
             20                  25                  30

Ile Pro Leu Ser Glu Met Val Val Lys Leu Thr Ala Val Cys Met Lys
         35                  40                  45

Cys Phe Lys Glu Ala Ser Phe Ser Lys Arg Leu Gly Glu Glu Thr Glu
     50                  55                  60

Ile Glu Ile Ile Gly Gly Asn Asp Met Tyr Gln Ser Val Cys Arg Lys
 65                  70                  75                  80

Cys Tyr Ile Asp Ser
                 85
```

```
<210> SEQ ID NO 14
<211> LENGTH: 286
<212> TYPE: PRT
<213> ORGANISM: Artificial Sequence
<220> FEATURE:
<223> OTHER INFORMATION: :

<400> SEQUENCE: 14

Met Ser Ile Gln His Phe Arg Val Ala Leu Ile Pro Phe Phe Ala Ala
  1               5                  10                  15

Phe Cys Leu Pro Val Phe Ala His Pro Glu Thr Leu Val Lys Val Lys
             20                  25                  30

Asp Ala Glu Asp Gln Leu Gly Ala Arg Val Gly Tyr Ile Glu Leu Asp
         35                  40                  45

Leu Asn Ser Gly Lys Ile Leu Glu Ser Phe Arg Pro Glu Glu Arg Phe
     50                  55                  60

Pro Met Met Ser Thr Phe Lys Val Leu Leu Cys Gly Ala Val Leu Ser
 65                  70                  75                  80

Arg Ile Asp Ala Gly Gln Glu Gln Leu Gly Arg Arg Ile His Tyr Ser
                 85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp
        275                 280                 285


<210> SEQ ID NO 15
<211> LENGTH: 13910
<212> TYPE: DNA
<213> ORGANISM: Artificial Sequence
<220> FEATURE:
<223> OTHER INFORMATION: Description of Artificial Sequence: plasmid
      phcap 4
<220> FEATURE:
<221> NAME/KEY: CDS
<222> LOCATION: (497)..(772)
<220> FEATURE:
<221> NAME/KEY: CDS
<222> LOCATION: (1425)..(6500)
<220> FEATURE:
```

-continued

<221> NAME/KEY: CDS
<222> LOCATION: (8579)..(9034)
<220> FEATURE:
<221> NAME/KEY: CDS
<222> LOCATION: (10191)..(10445)
<220> FEATURE:
<221> NAME/KEY: CDS
<222> LOCATION: (11877)..(12734)
<220> FEATURE:
<221> NAME/KEY: misc_feature
<222> LOCATION: (1)..(774)
<223> OTHER INFORMATION: Vaccinia Virus thymidine Kinase gene recombination site
<220> FEATURE:
<221> NAME/KEY: promoter
<222> LOCATION: (794)..(816)
<223> OTHER INFORMATION: T7 promoter
<220> FEATURE:
<221> NAME/KEY: misc_feature
<222> LOCATION: (846)..(1424)
<223> OTHER INFORMATION: EMC/Internal Ribosome Entry Site (IRES)
<220> FEATURE:
<221> NAME/KEY: misc_feature
<222> LOCATION: (1426)..(1437)
<223> OTHER INFORMATION: MCS (Multiple Cloning Site)
<220> FEATURE:
<221> NAME/KEY: misc_feature
<222> LOCATION: (1446)..(2318)
<223> OTHER INFORMATION: HCV E2/ NS2 domain
<220> FEATURE:
<221> NAME/KEY: misc_feature
<222> LOCATION: (2319)..(4231)
<223> OTHER INFORMATION: HCV NS3 Domain containing the serine protease and helicase enzymes
<220> FEATURE:
<221> NAME/KEY: misc_feature
<222> LOCATION: (4203)..(4260)
<223> OTHER INFORMATION: HCV NS3-NS4A cleavage site
<220> FEATURE:
<221> NAME/KEY: misc_feature
<222> LOCATION: (4375)..(4424)
<223> OTHER INFORMATION: HCV NS4A-4B clevage site
<220> FEATURE:
<221> NAME/KEY: misc_feature
<222> LOCATION: (4233)..(4394)
<223> OTHER INFORMATION: HCV NS4A domain
<220> FEATURE:
<221> NAME/KEY: misc_feature
<222> LOCATION: (4395)..(4919)
<223> OTHER INFORMATION: HCV NS4B Domain
<220> FEATURE:
<221> NAME/KEY: misc_feature
<222> LOCATION: (4920)..(4991)
<223> OTHER INFORMATION: HCV NS5A-NS5B cleavage site
<220> FEATURE:
<221> NAME/KEY: misc_feature
<222> LOCATION: (4992)..(6501)
<223> OTHER INFORMATION: SEAP Protein
<220> FEATURE:
<221> NAME/KEY: misc_feature
<222> LOCATION: (7915)..(7945)
<223> OTHER INFORMATION: MCS (Multiple Cloning Site)
<220> FEATURE:
<221> NAME/KEY: terminator
<222> LOCATION: (7938)..(8078)
<223> OTHER INFORMATION: term T7
<220> FEATURE:
<221> NAME/KEY: promoter
<222> LOCATION: (8080)..(8365)
<223> OTHER INFORMATION: Vacinina virus promoter; early/late promoter
<220> FEATURE:
<221> NAME/KEY: misc_feature
<222> LOCATION: (8560)..(11317)
<223> OTHER INFORMATION: E. coli gpt; for selection of recombinants
<220> FEATURE:
<221> NAME/KEY: misc_feature
<222> LOCATION: (11318)..(13909)
<223> OTHER INFORMATION: remaining DNA from 3' end of  Tropix pCMV/SEAP plasmid -continued

```
<400> SEQUENCE: 15

aagcttttgc gatcaataaa tggatcacaa ccagtatctc ttaacgatgt tcttcgcaga     60

tgatgattca ttttttaagt atttggctag tcaagatgat gaatcttcat tatctgatat    120

attgcaaatc actcaatatc tagactttct gttattatta ttgatccaat caaaaaataa    180

attagaagcc gtgggtcatt gttatgaatc tctttcagag gaatacagac aattgacaaa    240

attcacagac tttcaagatt ttaaaaaact gtttaacaag gtccctattg ttacagatgg    300

aagggtcaaa cttaataaag gatatttgtt cgactttgtg attagtttga tgcgattcaa    360

aaaagaatcc tctctagcta ccaccgcaat agatcctgtt agatacatag atcctcgtcg    420

caatatcgca ttttctaacg tgatggatat attaaagtcg aataaagtga acaataatta    480

attctttatt gtcatc atg aac ggc gga cat att cag ttg ata atc ggc ccc    532
                  Met Asn Gly Gly His Ile Gln Leu Ile Ile Gly Pro
                  1               5                   10

atg ttt tca ggt aaa agt aca gaa tta att aga cga gtt aga cgt tat      580
Met Phe Ser Gly Lys Ser Thr Glu Leu Ile Arg Arg Val Arg Arg Tyr
        15                  20                  25

caa ata gct caa tat aaa tgc gtg act ata aaa tat tct aac gat aat      628
Gln Ile Ala Gln Tyr Lys Cys Val Thr Ile Lys Tyr Ser Asn Asp Asn
    30                  35                  40

aga tac gga acg gga cta tgg acg cat gat aag aat aat ttt gaa gca      676
Arg Tyr Gly Thr Gly Leu Trp Thr His Asp Lys Asn Asn Phe Glu Ala
45                  50                  55                  60

ttg gaa gca act aaa cta tgt gat gtc ttg gaa tca att aca gat ttc      724
Leu Glu Ala Thr Lys Leu Cys Asp Val Leu Glu Ser Ile Thr Asp Phe
                65                  70                  75

tcc gtg ata ggt atc gat gaa gga cag ttc ttt cca gac att gtt gaa      772
Ser Val Ile Gly Ile Asp Glu Gly Gln Phe Phe Pro Asp Ile Val Glu
            80                  85                  90

ttgatctcga tcccgcgaaa ttaatacgac tcactatagg gagaccacaa cggtttccct    832

ctagcgggat caattccgcc cctctccctc ccccccccct aacgttactg gccgaagccg    892

cttggaataa ggccggtgtg cgtttgtcta tatgttattt tccaccatat tgccgtcttt    952

tggcaatgtg agggcccgga aacctggccc tgtcttcttg acgagcattc ctaggggtct   1012

ttcccctctc gccaaaggaa tgcaaggtct gttgaatgtc gtgaaggaag cagttcctct   1072

ggaagcttct tgaagacaaa caacgtctgt agcgaccctt tgcaggcagc ggaacccccc   1132

acctggcgac aggtgcctct gcggccaaaa gccacgtgta taagatacac ctgcaaaggc   1192

ggcacaaccc cagtgccacg ttgtgagttg gatagttgtg gaaagagtca aatggctctc   1252

ctcaagcgta ttcaacaagg ggctgaagga tgcccagaag gtaccccatt gtatgggatc   1312

tgatctgggg cctcggtgca catgctttac atgtgtttag tcgaggttaa aaaacgtcta   1372

ggccccccga accacgggga cgtggttttc ctttgaaaaa cacgataata cc atg gga   1430
                                                          Met Gly

att ccc caa ttc atg gca cgt gtc tgt gcc tgc ttg tgg atg atg ctg     1478
Ile Pro Gln Phe Met Ala Arg Val Cys Ala Cys Leu Trp Met Met Leu
95                  100                 105                 110

ctg ata gcc cag gcc gag gcc gcc ttg gag aac ctg gtg gtc ctc aat     1526
Leu Ile Ala Gln Ala Glu Ala Ala Leu Glu Asn Leu Val Val Leu Asn
                115                 120                 125

gcg gcg tct gtg gcc ggc gca cat ggc atc ctc tcc ttc ctt gtg ttc     1574
Ala Ala Ser Val Ala Gly Ala His Gly Ile Leu Ser Phe Leu Val Phe
            130                 135                 140

ttc tgt gcc gcc tgg tac atc aaa ggc agg ctg gtc cct ggg gcg gca     1622
```

-continued

```
Phe Cys Ala Ala Trp Tyr Ile Lys Gly Arg Leu Val Pro Gly Ala Ala
        145                 150                 155

tat gct ctt tat ggc gtg tgg ccg ctg ctc ctg ctc ttg ctg gca tta     1670
Tyr Ala Leu Tyr Gly Val Trp Pro Leu Leu Leu Leu Leu Leu Ala Leu
    160                 165                 170

cca ccg cga gct tac gcc atg gac cgg gag atg gct gca tcg tgc gga     1718
Pro Pro Arg Ala Tyr Ala Met Asp Arg Glu Met Ala Ala Ser Cys Gly
175                 180                 185                 190

ggc gcg gtt ttt gtg ggt ctg gta ctc ctg act ttg tca cca tac tac     1766
Gly Ala Val Phe Val Gly Leu Val Leu Leu Thr Leu Ser Pro Tyr Tyr
                195                 200                 205

aag gtg ttc ctc gct agg ctc ata tgg tgg tta caa tat ttt acc acc     1814
Lys Val Phe Leu Ala Arg Leu Ile Trp Trp Leu Gln Tyr Phe Thr Thr
            210                 215                 220

aga gcc gag gcg cac tta cat gtg tgg atc ccc ccc ctc aac gct cgg     1862
Arg Ala Glu Ala His Leu His Val Trp Ile Pro Pro Leu Asn Ala Arg
        225                 230                 235

gga ggc cgc gat gcc atc atc ctc ctc atg tgc gca gtc cat cca gag     1910
Gly Gly Arg Asp Ala Ile Ile Leu Leu Met Cys Ala Val His Pro Glu
    240                 245                 250

cta atc ttt gac atc acc aaa ctt cta att gcc ata ctc ggt ccg ctc     1958
Leu Ile Phe Asp Ile Thr Lys Leu Leu Ile Ala Ile Leu Gly Pro Leu
255                 260                 265                 270

atg gtg ctc caa gct ggc ata acc aga gtg ccg tac ttc gtg cgc gct     2006
Met Val Leu Gln Ala Gly Ile Thr Arg Val Pro Tyr Phe Val Arg Ala
                275                 280                 285

caa ggg ctc att cat gca tgc atg tta gtg cgg aag gtc gct ggg ggt     2054
Gln Gly Leu Ile His Ala Cys Met Leu Val Arg Lys Val Ala Gly Gly
            290                 295                 300

cat tat gtc caa atg gcc ttc atg aag ctg ggc gcg ctg aca ggc acg     2102
His Tyr Val Gln Met Ala Phe Met Lys Leu Gly Ala Leu Thr Gly Thr
        305                 310                 315

tac att tac aac cat ctt acc ccg cta cgg gat tgg gcc cac gcg ggc     2150
Tyr Ile Tyr Asn His Leu Thr Pro Leu Arg Asp Trp Ala His Ala Gly
    320                 325                 330

cta cga gac ctt gcg gtg gca gtg gag ccc gtc gtc ttc tcc gac atg     2198
Leu Arg Asp Leu Ala Val Ala Val Glu Pro Val Val Phe Ser Asp Met
335                 340                 345                 350

gag acc aag atc atc acc tgg gga gca gac acc gcg gcg gct ggg gac     2246
Glu Thr Lys Ile Ile Thr Trp Gly Ala Asp Thr Ala Ala Ala Gly Asp
                355                 360                 365

atc atc ttg ggt ctg ccc gtc tcc gcc cga agg gga aag gag ata ctc     2294
Ile Ile Leu Gly Leu Pro Val Ser Ala Arg Arg Gly Lys Glu Ile Leu
            370                 375                 380

ctg ggc ccg gcc gat agt ctt gaa ggg cgg ggg tgg cga ctc ctc gcg     2342
Leu Gly Pro Ala Asp Ser Leu Glu Gly Arg Gly Trp Arg Leu Leu Ala
        385                 390                 395

ccc atc acg gcc tac tcc caa cag acg cgg ggc cta ctt ggt tgc atc     2390
Pro Ile Thr Ala Tyr Ser Gln Gln Thr Arg Gly Leu Leu Gly Cys Ile
    400                 405                 410

atc act agc ctt aca ggc cgg gac aag aac cag gtc gag gga gag gtt     2438
Ile Thr Ser Leu Thr Gly Arg Asp Lys Asn Gln Val Glu Gly Glu Val
415                 420                 425                 430

cag gtg gtt tcc acc gca aca caa tcc ttc ctg gcg acc tgc gtc aac     2486
Gln Val Val Ser Thr Ala Thr Gln Ser Phe Leu Ala Thr Cys Val Asn
                435                 440                 445

ggc gtg tgt tgg acc gtt tac cat ggt gct ggc tca aag acc tta gcc     2534
Gly Val Cys Trp Thr Val Tyr His Gly Ala Gly Ser Lys Thr Leu Ala
            450                 455                 460
```

-continued

```
ggc cca aag ggg cca atc acc cag atg tac act aat gtg gac cag gac     2582
Gly Pro Lys Gly Pro Ile Thr Gln Met Tyr Thr Asn Val Asp Gln Asp
        465                 470                 475

ctc gtc ggc tgg cag gcg ccc ccc ggg gcg cgt tcc ttg aca cca tgc     2630
Leu Val Gly Trp Gln Ala Pro Pro Gly Ala Arg Ser Leu Thr Pro Cys
    480                 485                 490

acc tgt ggc agc tca gac ctt tac ttg gtc acg aga cat gct gac gtc     2678
Thr Cys Gly Ser Ser Asp Leu Tyr Leu Val Thr Arg His Ala Asp Val
495                 500                 505                 510

att ccg gtg cgc cgg cgg ggc gac agt agg ggg agc ctg ctc tcc ccc     2726
Ile Pro Val Arg Arg Arg Gly Asp Ser Arg Gly Ser Leu Leu Ser Pro
                515                 520                 525

agg cct gtc tcc tac ttg aag ggc tct gcg ggt ggt cca ctg ctc tgc     2774
Arg Pro Val Ser Tyr Leu Lys Gly Ser Ala Gly Gly Pro Leu Leu Cys
            530                 535                 540

cct tcg ggg cac gct gtg ggc atc ttc cgg gct gcc gta tgc acc cgg     2822
Pro Ser Gly His Ala Val Gly Ile Phe Arg Ala Ala Val Cys Thr Arg
        545                 550                 555

ggg gtt gcg aag gcg gtg gac ttt gtg ccc gta gag tcc atg gaa act     2870
Gly Val Ala Lys Ala Val Asp Phe Val Pro Val Glu Ser Met Glu Thr
    560                 565                 570

act atg cgg tct ccg gtc ttc acg gac aac tca tcc ccc ccg gcc gta     2918
Thr Met Arg Ser Pro Val Phe Thr Asp Asn Ser Ser Pro Pro Ala Val
575                 580                 585                 590

ccg cag tca ttt caa gtg gcc cac cta cac gct ccc act ggc agc ggc     2966
Pro Gln Ser Phe Gln Val Ala His Leu His Ala Pro Thr Gly Ser Gly
                595                 600                 605

aag agt act aaa gtg ccg gct gca tat gca gcc caa ggg tac aag gtg     3014
Lys Ser Thr Lys Val Pro Ala Ala Tyr Ala Ala Gln Gly Tyr Lys Val
            610                 615                 620

ctc gtc ctc aat ccg tcc gtt gcc gct acc tta ggg ttt ggg gcg tat     3062
Leu Val Leu Asn Pro Ser Val Ala Ala Thr Leu Gly Phe Gly Ala Tyr
        625                 630                 635

atg tct aag gca cac ggt att gac ccc aac atc aga act ggg gta agg     3110
Met Ser Lys Ala His Gly Ile Asp Pro Asn Ile Arg Thr Gly Val Arg
    640                 645                 650

acc att acc aca ggc gcc ccc gtc aca tac tct acc tat ggc aag ttt     3158
Thr Ile Thr Thr Gly Ala Pro Val Thr Tyr Ser Thr Tyr Gly Lys Phe
655                 660                 665                 670

ctt gcc gat ggt ggt tgc tct ggg ggc gct tat gac atc ata ata tgt     3206
Leu Ala Asp Gly Gly Cys Ser Gly Gly Ala Tyr Asp Ile Ile Ile Cys
                675                 680                 685

gat gag tgc cat tca act gac tcg act aca atc ttg ggc atc ggc aca     3254
Asp Glu Cys His Ser Thr Asp Ser Thr Thr Ile Leu Gly Ile Gly Thr
            690                 695                 700

gtc ctg gac caa gcg gag acg gct gga gcg cgg ctt gtc gtg ctc gcc     3302
Val Leu Asp Gln Ala Glu Thr Ala Gly Ala Arg Leu Val Val Leu Ala
        705                 710                 715

acc gct acg cct ccg gga tcg gtc acc gtg cca cac cca aac atc gag     3350
Thr Ala Thr Pro Pro Gly Ser Val Thr Val Pro His Pro Asn Ile Glu
    720                 725                 730

gag gtg gcc ctg tct aat act gga gag atc ccc ttc tat ggc aaa gcc     3398
Glu Val Ala Leu Ser Asn Thr Gly Glu Ile Pro Phe Tyr Gly Lys Ala
735                 740                 745                 750

atc ccc att gaa gcc atc agg ggg gga agg cat ctc att ttc tgt cat     3446
Ile Pro Ile Glu Ala Ile Arg Gly Gly Arg His Leu Ile Phe Cys His
                755                 760                 765

tcc aag aag aag tgc gac gag ctc gcc gca aag ctg tca ggc ctc gga     3494
Ser Lys Lys Lys Cys Asp Glu Leu Ala Ala Lys Leu Ser Gly Leu Gly
            770                 775                 780
```

-continued

```
atc aac gct gtg gcg tat tac cgg ggg ctc gat gtg tcc gtc ata cca     3542
Ile Asn Ala Val Ala Tyr Tyr Arg Gly Leu Asp Val Ser Val Ile Pro
        785                 790                 795

act atc gga gac gtc gtt gtc gtg gca aca gac gct ctg atg acg ggc     3590
Thr Ile Gly Asp Val Val Val Val Ala Thr Asp Ala Leu Met Thr Gly
    800                 805                 810

tat acg ggc gac ttt gac tca gtg atc gac tgt aac aca tgt gtc acc     3638
Tyr Thr Gly Asp Phe Asp Ser Val Ile Asp Cys Asn Thr Cys Val Thr
815                 820                 825                 830

cag aca gtc gac ttc agc ttg gat ccc acc ttc acc att gag acg acg     3686
Gln Thr Val Asp Phe Ser Leu Asp Pro Thr Phe Thr Ile Glu Thr Thr
                835                 840                 845

acc gtg cct caa gac gca gtg tcg cgc tcg cag cgg cgg ggt agg act     3734
Thr Val Pro Gln Asp Ala Val Ser Arg Ser Gln Arg Arg Gly Arg Thr
            850                 855                 860

ggc agg ggt agg aga ggc atc tac agg ttt gtg act ccg gga gaa cgg     3782
Gly Arg Gly Arg Arg Gly Ile Tyr Arg Phe Val Thr Pro Gly Glu Arg
        865                 870                 875

ccc tcg ggc atg ttc gat tcc tcg gtc ctg tgt gag tgc tat gac gcg     3830
Pro Ser Gly Met Phe Asp Ser Ser Val Leu Cys Glu Cys Tyr Asp Ala
    880                 885                 890

ggc tgt gct tgg tac gag ctc acc ccc gcc gag acc tcg gtt agg ttg     3878
Gly Cys Ala Trp Tyr Glu Leu Thr Pro Ala Glu Thr Ser Val Arg Leu
895                 900                 905                 910

cgg gcc tac ctg aac aca cca ggg ttg ccc gtt tgc cag gac cac ctg     3926
Arg Ala Tyr Leu Asn Thr Pro Gly Leu Pro Val Cys Gln Asp His Leu
                915                 920                 925

gag ttc tgg gag agt gtc ttc aca ggc ctc acc cat ata gat gca cac     3974
Glu Phe Trp Glu Ser Val Phe Thr Gly Leu Thr His Ile Asp Ala His
            930                 935                 940

ttc ttg tcc cag acc aag cag gca gga gac aac ttc ccc tac ctg gta     4022
Phe Leu Ser Gln Thr Lys Gln Ala Gly Asp Asn Phe Pro Tyr Leu Val
        945                 950                 955

gca tac caa gcc acg gtg tgc gcc agg gct cag gcc cca cct cca tca     4070
Ala Tyr Gln Ala Thr Val Cys Ala Arg Ala Gln Ala Pro Pro Pro Ser
    960                 965                 970

tgg gat caa atg tgg aag tgt ctc ata cgg ctg aaa cct acg ctg cac     4118
Trp Asp Gln Met Trp Lys Cys Leu Ile Arg Leu Lys Pro Thr Leu His
975                 980                 985                 990

ggg cca aca ccc ttg ctg tac agg ctg gga gcc gtc caa aat gag gtc     4166
Gly Pro Thr Pro Leu Leu Tyr Arg Leu Gly Ala Val Gln Asn Glu Val
                995                1000                1005

acc ctc acc cac ccc ata acc aaa tac atc atg gca tgc atg tcg gct     4214
Thr Leu Thr His Pro Ile Thr Lys Tyr Ile Met Ala Cys Met Ser Ala
           1010                1015                1020

gac ctg gag gtc gtc act agc acc tgg gtg ctg gtg ggc gga gtc ctt     4262
Asp Leu Glu Val Val Thr Ser Thr Trp Val Leu Val Gly Gly Val Leu
       1025                1030                1035

gca gct ctg gcc gcg tat tgc ctg aca aca ggc agt gtg gtc att gtg     4310
Ala Ala Leu Ala Ala Tyr Cys Leu Thr Thr Gly Ser Val Val Ile Val
   1040                1045                1050

ggt agg att atc ttg tcc ggg agg ccg gcc att gtt ccc gac agg gag     4358
Gly Arg Ile Ile Leu Ser Gly Arg Pro Ala Ile Val Pro Asp Arg Glu
1055               1060                1065                1070

ctt ctc tac cag gag ttc gat gaa atg gaa gag tgc gcc tcg cac ctc     4406
Leu Leu Tyr Gln Glu Phe Asp Glu Met Glu Glu Cys Ala Ser His Leu
               1075                1080                1085

cct tac atc gag cag gga atg cag ctc gcc gag caa ttc aag cag aaa     4454
Pro Tyr Ile Glu Gln Gly Met Gln Leu Ala Glu Gln Phe Lys Gln Lys
```

-continued

```
          1090                1095                1100

gcg ctc ggg tta ctg caa aca gcc acc aaa caa gcg gag gct gct gct     4502
Ala Leu Gly Leu Leu Gln Thr Ala Thr Lys Gln Ala Glu Ala Ala Ala
       1105                1110                1115

ccc gtg gtg gag tcc aag tgg cga gcc ctt gag aca ttc tgg gcg aag     4550
Pro Val Val Glu Ser Lys Trp Arg Ala Leu Glu Thr Phe Trp Ala Lys
   1120                1125                1130

cac atg tgg aat ttc atc agc ggg ata cag tac tta gca ggc tta tcc     4598
His Met Trp Asn Phe Ile Ser Gly Ile Gln Tyr Leu Ala Gly Leu Ser
1135                1140                1145                1150

act ctg cct ggg aac ccc gca ata gca tca ttg atg gca ttc aca gcc     4646
Thr Leu Pro Gly Asn Pro Ala Ile Ala Ser Leu Met Ala Phe Thr Ala
               1155                1160                1165

tct atc acc agc ccg ctc acc acc caa agt acc ctc ctg ttt aac atc     4694
Ser Ile Thr Ser Pro Leu Thr Thr Gln Ser Thr Leu Leu Phe Asn Ile
           1170                1175                1180

ttg ggg ggg tgg gtg gct gcc caa ctc gcc ccc ccc agc gcc gct tcg     4742
Leu Gly Gly Trp Val Ala Ala Gln Leu Ala Pro Pro Ser Ala Ala Ser
       1185                1190                1195

gct ttc gtg ggc gcc ggc atc gcc ggt gcg gct gtt ggc agc ata ggc     4790
Ala Phe Val Gly Ala Gly Ile Ala Gly Ala Ala Val Gly Ser Ile Gly
   1200                1205                1210

ctt ggg aag gtg ctt gtg gac att ctg gcg ggt tat gga gca gga gtg     4838
Leu Gly Lys Val Leu Val Asp Ile Leu Ala Gly Tyr Gly Ala Gly Val
1215                1220                1225                1230

gcc ggc gcg ctc gtg gcc ttt aag gtc atg agc ggc gag atg ccc tcc     4886
Ala Gly Ala Leu Val Ala Phe Lys Val Met Ser Gly Glu Met Pro Ser
               1235                1240                1245

acc gag gac ctg gtc aat cta ctt cct gcc atc ctc gag gaa gct agt     4934
Thr Glu Asp Leu Val Asn Leu Leu Pro Ala Ile Leu Glu Glu Ala Ser
           1250                1255                1260

gag gat gtc gtc tgc tgc tca atg tcc tac aca tgg aca ggc gcc ttg     4982
Glu Asp Val Val Cys Cys Ser Met Ser Tyr Thr Trp Thr Gly Ala Leu
       1265                1270                1275

gag ctg ctg ctg ctg ctg ctg ctg ggc ctg agg cta cag ctc tcc ctg     5030
Glu Leu Leu Leu Leu Leu Leu Leu Gly Leu Arg Leu Gln Leu Ser Leu
   1280                1285                1290

ggc atc atc cca gtt gag gag gag aac ccg gac ttc tgg aac cgc gag     5078
Gly Ile Ile Pro Val Glu Glu Glu Asn Pro Asp Phe Trp Asn Arg Glu
1295                1300                1305                1310

gca gcc gag gcc ctg ggt gcc gcc aag aag ctg cag cct gca cag aca     5126
Ala Ala Glu Ala Leu Gly Ala Ala Lys Lys Leu Gln Pro Ala Gln Thr
               1315                1320                1325

gcc gcc aag aac ctc atc atc ttc ctg ggc gat ggg atg ggg gtg tct     5174
Ala Ala Lys Asn Leu Ile Ile Phe Leu Gly Asp Gly Met Gly Val Ser
           1330                1335                1340

acg gtg aca gct gcc agg atc cta aaa ggg cag aag aag gac aaa ctg     5222
Thr Val Thr Ala Ala Arg Ile Leu Lys Gly Gln Lys Lys Asp Lys Leu
       1345                1350                1355

ggg cct gag ata ccc ctg gcc atg gac cgc ttc cca tat gtg gct ctg     5270
Gly Pro Glu Ile Pro Leu Ala Met Asp Arg Phe Pro Tyr Val Ala Leu
   1360                1365                1370

tcc aag aca tac aat gta gac aaa cat gtg cca gac agt gga gcc aca     5318
Ser Lys Thr Tyr Asn Val Asp Lys His Val Pro Asp Ser Gly Ala Thr
1375                1380                1385                1390

gcc acg gcc tac ctg tgc ggg gtc aag ggc aac ttc cag acc att ggc     5366
Ala Thr Ala Tyr Leu Cys Gly Val Lys Gly Asn Phe Gln Thr Ile Gly
               1395                1400                1405

ttg agt gca gcc gcc cgc ttt aac cag tgc aac acg aca cgc ggc aac     5414
```

-continued

```
Leu Ser Ala Ala Ala Arg Phe Asn Gln Cys Asn Thr Thr Arg Gly Asn
          1410                1415                1420

gag gtc atc tcc gtg atg aat cgg gcc aag aaa gca ggg aag tca gtg     5462
Glu Val Ile Ser Val Met Asn Arg Ala Lys Lys Ala Gly Lys Ser Val
      1425                1430                1435

gga gtg gta acc acc aca cga gtg cag cac gcc tcg cca gcc ggc acc     5510
Gly Val Val Thr Thr Thr Arg Val Gln His Ala Ser Pro Ala Gly Thr
   1440                1445                1450

tac gcc cac acg gtg aac cgc aac tgg tac tcg gac gcc gac gtg cct     5558
Tyr Ala His Thr Val Asn Arg Asn Trp Tyr Ser Asp Ala Asp Val Pro
1455                1460                1465                1470

gcc tcg gcc cgc cag gag ggg tgc cag gac atc gct acg cag ctc atc     5606
Ala Ser Ala Arg Gln Glu Gly Cys Gln Asp Ile Ala Thr Gln Leu Ile
              1475                1480                1485

tcc aac atg gac att gac gtg atc cta ggt gga ggc cga aag tac atg     5654
Ser Asn Met Asp Ile Asp Val Ile Leu Gly Gly Gly Arg Lys Tyr Met
          1490                1495                1500

ttt ccc atg gga acc cca gac cct gag tac cca gat gac tac agc caa     5702
Phe Pro Met Gly Thr Pro Asp Pro Glu Tyr Pro Asp Asp Tyr Ser Gln
      1505                1510                1515

ggt ggg acc agg ctg gac ggg aag aat ctg gtg cag gaa tgg ctg gcg     5750
Gly Gly Thr Arg Leu Asp Gly Lys Asn Leu Val Gln Glu Trp Leu Ala
   1520                1525                1530

aag cgc cag ggt gcc cgg tat gtg tgg aac cgc act gag ctg atg cag     5798
Lys Arg Gln Gly Ala Arg Tyr Val Trp Asn Arg Thr Glu Leu Met Gln
1535                1540                1545                1550

gct tcc ctg gac ccg tct gtg acc cat ctc atg ggt ctc ttt gag cct     5846
Ala Ser Leu Asp Pro Ser Val Thr His Leu Met Gly Leu Phe Glu Pro
              1555                1560                1565

gga gac atg aaa tac gag atc cac cga gac tcc aca ctg gac ccc tcc     5894
Gly Asp Met Lys Tyr Glu Ile His Arg Asp Ser Thr Leu Asp Pro Ser
          1570                1575                1580

ctg atg gag atg aca gag gct gcc ctg cgc ctg ctg agc agg aac ccc     5942
Leu Met Glu Met Thr Glu Ala Ala Leu Arg Leu Leu Ser Arg Asn Pro
      1585                1590                1595

cgc ggc ttc ttc ctc ttc gtg gag ggt ggt cgc atc gac cat ggt cat     5990
Arg Gly Phe Phe Leu Phe Val Glu Gly Gly Arg Ile Asp His Gly His
   1600                1605                1610

cat gaa agc agg gct tac cgg gca ctg act gag acg atc atg ttc gac     6038
His Glu Ser Arg Ala Tyr Arg Ala Leu Thr Glu Thr Ile Met Phe Asp
1615                1620                1625                1630

gac gcc att gag agg gcg ggc cag ctc acc agc gag gag gac acg ctg     6086
Asp Ala Ile Glu Arg Ala Gly Gln Leu Thr Ser Glu Glu Asp Thr Leu
              1635                1640                1645

agc ctc gtc act gcc gac cac tcc cac gtc ttc tcc ttc gga ggc tac     6134
Ser Leu Val Thr Ala Asp His Ser His Val Phe Ser Phe Gly Gly Tyr
          1650                1655                1660

ccc ctg cga ggg agc tgc atc ttc ggg ctg gcc cct ggc aag gcc cgg     6182
Pro Leu Arg Gly Ser Cys Ile Phe Gly Leu Ala Pro Gly Lys Ala Arg
      1665                1670                1675

gac agg aag gcc tac acg gtc ctc cta tac gga aac ggt cca ggc tat     6230
Asp Arg Lys Ala Tyr Thr Val Leu Leu Tyr Gly Asn Gly Pro Gly Tyr
   1680                1685                1690

gtg ctc aag gac ggc gcc cgg ccg gat gtt acc gag agc gag agc ggg     6278
Val Leu Lys Asp Gly Ala Arg Pro Asp Val Thr Glu Ser Glu Ser Gly
1695                1700                1705                1710

agc ccc gag tat cgg cag cag tca gca gtg ccc ctg gac gaa gag acc     6326
Ser Pro Glu Tyr Arg Gln Gln Ser Ala Val Pro Leu Asp Glu Glu Thr
              1715                1720                1725
```

-continued

```
cac gca ggc gag gac gtg gcg gtg ttc gcg cgc ggc ccg cag gcg cac     6374
His Ala Gly Glu Asp Val Ala Val Phe Ala Arg Gly Pro Gln Ala His
        1730                1735                1740

ctg gtt cac ggc gtg cag gag cag acc ttc ata gcg cac gtc atg gcc     6422
Leu Val His Gly Val Gln Glu Gln Thr Phe Ile Ala His Val Met Ala
    1745                1750                1755

ttc gcc gcc tgc ctg gag ccc tac acc gcc tgc gac ctg gcg ccc ccc     6470
Phe Ala Ala Cys Leu Glu Pro Tyr Thr Ala Cys Asp Leu Ala Pro Pro
 1760                1765                1770

gcc ggc acc acc gac gcc gcg cac ccg ggt taacccgtgg tccccgcgtt      6520
Ala Gly Thr Thr Asp Ala Ala His Pro Gly
1775                1780

gcttcctctg ctggccggga catcaggtgg cccccgctga attggaatcg atattgttac   6580

aacaccccaa catcttcgac gcgggcgtgg caggtcttcc cgacgatgac gccggtgaac   6640

ttcccgccgc cgttgttgtt ttggagcacg gaaagacgat gacggaaaaa gagatcgtgg   6700

attacgtcgc cagtcaagta acaaccgcga aaaagttgcg cggaggagtt gtgtttgtgg   6760

acgaagtacc gaaaggtctt accggaaaac tcgacgcaag aaaaatcaga gagatcctca   6820

taaaggccaa gaagggcgga aagtccaaat tgtaaaatgt aactgtattc agcgatgacg   6880

aaattcttag ctattgtaat actgcgatga gtggcagggc ggggcgtaat ttttttaagg   6940

cagttattgg tgcccttaaa cgcctggtgc tacgcctgaa taagtgataa taagcggatg   7000

aatggcagaa attcgccgga tctttgtgaa ggaaccttac ttctgtggtg tgacataatt   7060

ggacaaacta cctacagaga tttaaagctc taaggtaaat ataaaatttt taagtgtata   7120

atgtgttaaa ctactgattc taattgtttg tgtattttag attccaacct atggaactga   7180

tgaatgggag cagtggtgga atgcctttaa tgaggaaaac ctgttttgct cagaagaaat   7240

gccatctagt gatgatgagg ctactgctga ctctcaacat tctactcctc caaaaaagaa   7300

gagaaaggta gaagacccca aggactttcc ttcagaattg ctaagttttt tgagtcatgc   7360

tgtgtttagt aatagaactc ttgcttgctt tgctatttac accacaaagg aaaaagctgc   7420

actgctatac aagaaaatta tggaaaaata ttctgtaacc tttataagta ggcataacag   7480

ttataatcat aacatactgt tttttcttac tccacacagg catagagtgt ctgctattaa   7540

taactatgct caaaaattgt gtacctttag ctttttaatt tgtaaagggg ttaataagga   7600

atatttgatg tatagtgcct tgactagaga tcataatcag ccataccaca tttgtagagg   7660

ttttacttgc tttaaaaaac ctcccacacc tccccctgaa cctgaaacat aaaatgaatg   7720

caattgttgt tgttaacttg tttattgcag cttataatgg ttacaaataa agcaatagca   7780

tcacaaattt cacaaataaa gcattttttt cactgcattc tagttgtggt ttgtccaaac   7840

tcatcaatgt atcttatcat gtctggatcc tctagagtcg acctgcaggc atgcaagctt   7900

ctcgagagta cttctagtgg atccctgcag ctcgagaggc ctaattaatt aagtcgacga   7960

tccggctgct aacaaagccc gaaaggaagc tgagttggct gctgccaccg ctgagcaata   8020

actagcataa ccccttgggg cctctaaacg ggtcttgagg ggttttttgc tgaaaggagg   8080

aactatatcc ggagttaact cgacatatac tatatagtaa taccaatact caagactacg   8140

aaactgatac aatctcttat catgtgggta atgttctcga tgtcgaatag ccatatgccg   8200

gtagttgcga tatacataaa ctgatcacta attccaaacc cacccgcttt ttatagtaag   8260

tttttcaccc ataaataata aatacaataa ttaatttctc gtaaaagtag aaaatatatt   8320

ctaatttatt gcacggtaag gaagtagaat cataaagaac agtgacggat cgatccccca   8380

agcttggaca caagacaggc ttgcgagata tgtttgagaa taccacttta tcccgcgtca   8440
```

-continued

```
gggagaggca gtgcgtaaaa agacgcggac tcatgtgaaa tactggtttt tagtgcgcca   8500

gatctctata atctcgcgca acctattttc ccctcgaaca ctttttaagc cgtagataaa   8560

caggctggga cacttcac atg agc gaa aaa tac atc gtc acc tgg gac atg     8611
                    Met Ser Glu Lys Tyr Ile Val Thr Trp Asp Met
                   1785                1790                1795

ttg cag atc cat gca cgt aaa ctc gca agc cga ctg atg cct tct gaa     8659
Leu Gln Ile His Ala Arg Lys Leu Ala Ser Arg Leu Met Pro Ser Glu
               1800                1805                1810

caa tgg aaa ggc att att gcc gta agc cgt ggc ggt ctg gta ccg ggt     8707
Gln Trp Lys Gly Ile Ile Ala Val Ser Arg Gly Gly Leu Val Pro Gly
           1815                1820                1825

gcg tta ctg gcg cgt gaa ctg ggt att cgt cat gtc gat acc gtt tgt     8755
Ala Leu Leu Ala Arg Glu Leu Gly Ile Arg His Val Asp Thr Val Cys
       1830                1835                1840

att tcc agc tac gat cac gac aac cag cgc gag ctt aaa gtg ctg aaa     8803
Ile Ser Ser Tyr Asp His Asp Asn Gln Arg Glu Leu Lys Val Leu Lys
   1845                1850                1855

cgc gca gaa ggc gat ggc gaa ggc ttc atc gtt att gat gac ctg gtg     8851
Arg Ala Glu Gly Asp Gly Glu Gly Phe Ile Val Ile Asp Asp Leu Val
1860                1865                1870                1875

gat acc ggt ggt act gcg gtt gcg att cgt gaa atg tat cca aaa gcg     8899
Asp Thr Gly Gly Thr Ala Val Ala Ile Arg Glu Met Tyr Pro Lys Ala
               1880                1885                1890

cac ttt gtc acc atc ttc gca aaa ccg gct ggt cgt ccg ctg gtt gat     8947
His Phe Val Thr Ile Phe Ala Lys Pro Ala Gly Arg Pro Leu Val Asp
           1895                1900                1905

gac tat gtt gtt gat atc ccg caa gat acc tgg att gaa cag ccg tgg     8995
Asp Tyr Val Val Asp Ile Pro Gln Asp Thr Trp Ile Glu Gln Pro Trp
       1910                1915                1920

gat atg ggc gtc gta ttc gtc ccg cca atc tcc ggt cgc taatcttttc      9044
Asp Met Gly Val Val Phe Val Pro Pro Ile Ser Gly Arg
   1925                1930                1935

aacgcctggc actgccgggc gttgttcttt ttaacttcag gcgggttaca atagtttcca   9104

gtaagtattc tggaggctgc atccatgaca caggcaaacc tgagcgaaac cctgttcaaa   9164

ccccgcttta aacatcctga aacctcgacg ctagtccgcc gctttaatca cggcgcacaa   9224

ccgcctgtgc agtcggccct tgatggtaaa accatccctc actggtatcg catgattaac   9284

cgtctgatgt ggatctggcg cggcattgac ccacgcgaaa tcctcgacgt ccaggcacgt   9344

attgtgatga gcgatgccga acgtaccgac gatgatttat acgatacggt gattggctac   9404

cgtggcggca actggattta tgagtgggcc ccggatcttt gtgaaggaac cttacttctg   9464

tggtgtgaca taattggaca aactacctac agagatttaa agctctaagg taaatataaa   9524

atttttaagt gtataatgtg ttaaactact gattctaatt gtttgtgtat tttagattcc   9584

aacctatgga actgatgaat gggagcagtg gtggaatgcc tttaatgagg aaaacctgtt   9644

ttgctcagaa gaaatgccat ctagtgatga tgaggctact gctgactctc aacattctac   9704

tcctccaaaa aagaagagaa aggtagaaga ccccaaggac tttccttcag aattgctaag   9764

ttttttgagt catgctgtgt ttagtaatag aactcttgct tgctttgcta tttacaccac   9824

aaaggaaaaa gctgcactgc tatacaagaa aattatggaa aaatattctg taacctttat   9884

aagtaggcat aacagttata atcataacat actgtttttt cttactccac acaggcatag   9944

agtgtctgct attaataact atgctcaaaa attgtgtacc tttagctttt taatttgtaa  10004

aggggttaat aaggaatatt tgatgtatag tgccttgact agagatcata atcagccata  10064
```

-continued

```
ccacatttgt agaggtttta cttgctttaa aaaacctccc acacctcccc ctgaacctga  10124

aacataaaat gaatgcaatt gttgttgtta agcttggggg aattgcatgc tccggatcga  10184

gatcaa ttc tgt gag cgt atg gca aac gaa gga aaa ata gtt ata gta     10232
       Phe Cys Glu Arg Met Ala Asn Glu Gly Lys Ile Val Ile Val
                  1940                1945                1950

gcc gca ctc gat ggg aca ttt caa cgt aaa ccg ttt aat aat att ttg    10280
Ala Ala Leu Asp Gly Thr Phe Gln Arg Lys Pro Phe Asn Asn Ile Leu
               1955                1960                1965

aat ctt att cca tta tct gaa atg gtg gta aaa cta act gct gtg tgt    10328
Asn Leu Ile Pro Leu Ser Glu Met Val Val Lys Leu Thr Ala Val Cys
           1970                1975                1980

atg aaa tgc ttt aag gag gct tcc ttt tct aaa cga ttg ggt gag gaa    10376
Met Lys Cys Phe Lys Glu Ala Ser Phe Ser Lys Arg Leu Gly Glu Glu
       1985                1990                1995

acc gag ata gaa ata ata gga ggt aat gat atg tat caa tcg gtg tgt    10424
Thr Glu Ile Glu Ile Ile Gly Gly Asn Asp Met Tyr Gln Ser Val Cys
   2000                2005                2010

aga aag tgt tac atc gac tca taatattata ttttttatct aaaaaactaa       10475
Arg Lys Cys Tyr Ile Asp Ser
2015                2020

aaataaacat tgattaaatt ttaatataat acttaaaaat ggatgttgtg tcgttagata  10535

aaccgtttat gtattttgag gaaattgata atgagttaga ttacgaacca gaaagtgcaa  10595

atgaggtcgc aaaaaaactg ccgtatcaag gacagttaaa actattacta ggagaattat  10655

tttttcttag taagttacag cgacacggta tattagatgg tgccaccgta gtgtatatag  10715

gatctgctcc cggtacacat atacgttatt tgagagatca tttctataat ttaggagtga  10775

tcatcaaatg gatgctaatt gacggccgcc atcatgatcc tattttaaat ggattgcgtg  10835

atgtgactct agtgactcgg ttcgttgatg aggaatatct acgatccatc aaaaaacaac  10895

tgcatccttc taagattatt ttaatttctg atgtgagatc caaacgagga ggaaatgaac  10955

ctagtacggc ggatttacta agtaattacg ctctacaaaa tgtcatgatt agtattttaa  11015

accccgtggc gtctagtctt aaatggagat gcccgtttcc agatcaatgg atcaaggact  11075

tttatatccc acacggtaat aaaatgttac aacctttgc tccttcatat tcagggccgt   11135

cgttttacaa cgtcgtgact gggaaaaccc tggcgttacc caacttaatc gccttgcagc  11195

acatccccct ttcgccagct ggcgtaatag cgaagaggcc cgcaccgatc gcccttccca  11255

acagttgcgc agcctgaatg gcgaatggcg cgacgcgccc tgtagcggcg cattaagcgc  11315

ggcgggtgtg gtggttacgc gcagcgtgac cgctacactt gccagcgccc tagcgcccgc  11375

tcctttcgct ttcttccctt cctttctcgc cacgttcgcc ggctttcccc gtcaagctct  11435

aaatcggggg ctccctttag ggttccgatt tagtgcttta cggcacctcg accccaaaaa  11495

acttgattag ggtgatggtt cacgtagtgg gccatcgccc tgatagacgg tttttcgccc  11555

tttgacgttg gagtccacgt tctttaatag tggactcttg ttccaaactg gaacaacact  11615

caaccctatc tcggtctatt cttttgattt ataagggatt ttgccgattt cggcctattg  11675

gttaaaaaat gagctgattt aacaaaaatt taacgcgaat tttaacaaaa tattaacgtt  11735

tacaatttcc caggtggcac ttttcgggga aatgtgcgcg gaacccctat ttgtttattt  11795

ttctaaatac attcaaatat gtatccgctc atgagacaat aaccctgata aatgcttcaa  11855

taatattgaa aaaggaagag t atg agt att caa cat ttc cgt gtc gcc ctt    11906
                        Met Ser Ile Gln His Phe Arg Val Ala Leu
                                    2025                2030

att ccc ttt ttt gcg gca ttt tgc ctt cct gtt ttt gct cac cca gaa    11954
```

-continued

```
Ile Pro Phe Phe Ala Ala Phe Cys Leu Pro Val Phe Ala His Pro Glu
          2035                2040                2045

acg ctg gtg aaa gta aaa gat gct gaa gat cag ttg ggt gca cga gtg    12002
Thr Leu Val Lys Val Lys Asp Ala Glu Asp Gln Leu Gly Ala Arg Val
      2050                2055                2060

ggt tac atc gaa ctg gat ctc aac agc ggt aag atc ctt gag agt ttt    12050
Gly Tyr Ile Glu Leu Asp Leu Asn Ser Gly Lys Ile Leu Glu Ser Phe
   2065                2070                2075

cgc ccc gaa gaa cgt ttt cca atg atg agc act ttt aaa gtt ctg cta    12098
Arg Pro Glu Glu Arg Phe Pro Met Met Ser Thr Phe Lys Val Leu Leu
2080                2085                2090                2095

tgt ggc gcg gta tta tcc cgt att gac gcc ggg caa gag caa ctc ggt    12146
Cys Gly Ala Val Leu Ser Arg Ile Asp Ala Gly Gln Glu Gln Leu Gly
              2100                2105                2110

cgc cgc ata cac tat tct cag aat gac ttg gtt gag tac tca cca gtc    12194
Arg Arg Ile His Tyr Ser Gln Asn Asp Leu Val Glu Tyr Ser Pro Val
          2115                2120                2125

aca gaa aag cat ctt acg gat ggc atg aca gta aga gaa tta tgc agt    12242
Thr Glu Lys His Leu Thr Asp Gly Met Thr Val Arg Glu Leu Cys Ser
      2130                2135                2140

gct gcc ata acc atg agt gat aac act gcg gcc aac tta ctt ctg aca    12290
Ala Ala Ile Thr Met Ser Asp Asn Thr Ala Ala Asn Leu Leu Leu Thr
   2145                2150                2155

acg atc gga gga ccg aag gag cta acc gct ttt ttg cac aac atg ggg    12338
Thr Ile Gly Gly Pro Lys Glu Leu Thr Ala Phe Leu His Asn Met Gly
2160                2165                2170                2175

gat cat gta act cgc ctt gat cgt tgg gaa ccg gag ctg aat gaa gcc    12386
Asp His Val Thr Arg Leu Asp Arg Trp Glu Pro Glu Leu Asn Glu Ala
              2180                2185                2190

ata cca aac gac gag cgt gac acc acg atg cct gta gca atg gca aca    12434
Ile Pro Asn Asp Glu Arg Asp Thr Thr Met Pro Val Ala Met Ala Thr
          2195                2200                2205

acg ttg cgc aaa cta tta act ggc gaa cta ctt act cta gct tcc cgg    12482
Thr Leu Arg Lys Leu Leu Thr Gly Glu Leu Leu Thr Leu Ala Ser Arg
      2210                2215                2220

caa caa tta ata gac tgg atg gag gcg gat aaa gtt gca gga cca ctt    12530
Gln Gln Leu Ile Asp Trp Met Glu Ala Asp Lys Val Ala Gly Pro Leu
   2225                2230                2235

ctg cgc tcg gcc ctt ccg gct ggc tgg ttt att gct gat aaa tct gga    12578
Leu Arg Ser Ala Leu Pro Ala Gly Trp Phe Ile Ala Asp Lys Ser Gly
2240                2245                2250                2255

gcc ggt gag cgt ggg tct cgc ggt atc att gca gca ctg ggg cca gat    12626
Ala Gly Glu Arg Gly Ser Arg Gly Ile Ile Ala Ala Leu Gly Pro Asp
              2260                2265                2270

ggt aag ccc tcc cgt atc gta gtt atc tac acg acg ggg agt cag gca    12674
Gly Lys Pro Ser Arg Ile Val Val Ile Tyr Thr Thr Gly Ser Gln Ala
          2275                2280                2285

act atg gat gaa cga aat aga cag atc gct gag ata ggt gcc tca ctg    12722
Thr Met Asp Glu Arg Asn Arg Gln Ile Ala Glu Ile Gly Ala Ser Leu
      2290                2295                2300

att aag cat tgg taactgtcag accaagttta ctcatatata ctttagattg        12774
Ile Lys His Trp
   2305

atttaaaact tcatttttaa tttaaaagga tctaggtgaa gatccttttt gataatctca  12834

tgaccaaaat cccttaacgt gagttttcgt tccactgagc gtcagacccc gtagaaaaga  12894

tcaaaggatc ttcttgagat cctttttttc tgcgcgtaat ctgctgcttg caaacaaaaa  12954

aaccaccgct accagcggtg gtttgtttgc cggatcaaga gctaccaact ctttttccga  13014
```

-continued

```
aggtaactgg cttcagcaga gcgcagatac caaatactgt ccttctagtg tagccgtagt  13074

taggccacca cttcaagaac tctgtagcac cgcctacata cctcgctctg ctaatcctgt  13134

taccagtggc tgctgccagt ggcgataagt cgtgtcttac cgggttggac tcaagacgat  13194

agttaccgga taaggcgcag cggtcgggct gaacgggggg ttcgtgcaca cagcccagct  13254

tggagcgaac gacctacacc gaactgagat acctacagcg tgagctatga gaaagcgcca  13314

cgcttcccga agggagaaag gcggacaggt atccggtaag cggcagggtc ggaacaggag  13374

agcgcacgag ggagcttcca gggggaaacg cctggtatct ttatagtcct gtcgggtttc  13434

gccacctctg acttgagcgt cgatttttgt gatgctcgtc aggggggcgg agcctatgga  13494

aaaacgccag caacgcggcc tttttacggt tcctggcctt ttgctggcct tttgctcaca  13554

tgttctttcc tgcgttatcc cctgattctg tggataaccg tattaccgcc tttgagtgag  13614

ctgataccgc tcgccgcagc cgaacgaccg agcgcagcga gtcagtgagc gaggaagcgg  13674

aagagcgccc aatacgcaaa ccgcctctcc ccgcgcgttg gccgattcat taatgcagct  13734

ggcacgacag gtttcccgac tggaaagcgg gcagtgagcg caacgcaatt aatgtgagtt  13794

agctcactca ttaggcaccc caggctttac actttatgct tccggctcgt atgttgtgtg  13854

gaattgtgag cggataacaa tttcacacag gaaacagcta tgaccatgat tacgcc      13910
```

<210> SEQ ID NO 16
<211> LENGTH: 2307
<212> TYPE: PRT
<213> ORGANISM: Artificial Sequence
<220> FEATURE:
<223> OTHER INFORMATION: :

<400> SEQUENCE: 16

```
Met Asn Gly Gly His Ile Gln Leu Ile Ile Gly Pro Met Phe Ser Gly
  1               5                  10                  15

Lys Ser Thr Glu Leu Ile Arg Arg Val Arg Arg Tyr Gln Ile Ala Gln
             20                  25                  30

Tyr Lys Cys Val Thr Ile Lys Tyr Ser Asn Asp Asn Arg Tyr Gly Thr
         35                  40                  45

Gly Leu Trp Thr His Asp Lys Asn Asn Phe Glu Ala Leu Glu Ala Thr
     50                  55                  60

Lys Leu Cys Asp Val Leu Glu Ser Ile Thr Asp Phe Ser Val Ile Gly
 65                  70                  75                  80

Ile Asp Glu Gly Gln Phe Phe Pro Asp Ile Val Glu Met Gly Ile Pro
                 85                  90                  95

Gln Phe Met Ala Arg Val Cys Ala Cys Leu Trp Met Met Leu Leu Ile
            100                 105                 110

Ala Gln Ala Glu Ala Ala Leu Glu Asn Leu Val Val Leu Asn Ala Ala
        115                 120                 125

Ser Val Ala Gly Ala His Gly Ile Leu Ser Phe Leu Val Phe Phe Cys
    130                 135                 140

Ala Ala Trp Tyr Ile Lys Gly Arg Leu Val Pro Gly Ala Ala Tyr Ala
145                 150                 155                 160

Leu Tyr Gly Val Trp Pro Leu Leu Leu Leu Leu Leu Ala Leu Pro Pro
                165                 170                 175

Arg Ala Tyr Ala Met Asp Arg Glu Met Ala Ala Ser Cys Gly Gly Ala
            180                 185                 190

Val Phe Val Gly Leu Val Leu Leu Thr Leu Ser Pro Tyr Tyr Lys Val
        195                 200                 205
```

-continued

```
Phe Leu Ala Arg Leu Ile Trp Trp Leu Gln Tyr Phe Thr Thr Arg Ala
    210                 215                 220

Glu Ala His Leu His Val Trp Ile Pro Pro Leu Asn Ala Arg Gly Gly
225                 230                 235                 240

Arg Asp Ala Ile Ile Leu Leu Met Cys Ala Val His Pro Glu Leu Ile
                245                 250                 255

Phe Asp Ile Thr Lys Leu Leu Ile Ala Ile Leu Gly Pro Leu Met Val
            260                 265                 270

Leu Gln Ala Gly Ile Thr Arg Val Pro Tyr Phe Val Arg Ala Gln Gly
        275                 280                 285

Leu Ile His Ala Cys Met Leu Val Arg Lys Val Ala Gly Gly His Tyr
    290                 295                 300

Val Gln Met Ala Phe Met Lys Leu Gly Ala Leu Thr Gly Thr Tyr Ile
305                 310                 315                 320

Tyr Asn His Leu Thr Pro Leu Arg Asp Trp Ala His Ala Gly Leu Arg
                325                 330                 335

Asp Leu Ala Val Ala Val Glu Pro Val Val Phe Ser Asp Met Glu Thr
            340                 345                 350

Lys Ile Ile Thr Trp Gly Ala Asp Thr Ala Ala Ala Gly Asp Ile Ile
        355                 360                 365

Leu Gly Leu Pro Val Ser Ala Arg Arg Gly Lys Glu Ile Leu Leu Gly
    370                 375                 380

Pro Ala Asp Ser Leu Glu Gly Arg Gly Trp Arg Leu Leu Ala Pro Ile
385                 390                 395                 400

Thr Ala Tyr Ser Gln Gln Thr Arg Gly Leu Leu Gly Cys Ile Ile Thr
                405                 410                 415

Ser Leu Thr Gly Arg Asp Lys Asn Gln Val Glu Gly Glu Val Gln Val
            420                 425                 430

Val Ser Thr Ala Thr Gln Ser Phe Leu Ala Thr Cys Val Asn Gly Val
        435                 440                 445

Cys Trp Thr Val Tyr His Gly Ala Gly Ser Lys Thr Leu Ala Gly Pro
    450                 455                 460

Lys Gly Pro Ile Thr Gln Met Tyr Thr Asn Val Asp Gln Asp Leu Val
465                 470                 475                 480

Gly Trp Gln Ala Pro Pro Gly Ala Arg Ser Leu Thr Pro Cys Thr Cys
                485                 490                 495

Gly Ser Ser Asp Leu Tyr Leu Val Thr Arg His Ala Asp Val Ile Pro
            500                 505                 510

Val Arg Arg Arg Gly Asp Ser Arg Gly Ser Leu Leu Ser Pro Arg Pro
        515                 520                 525

Val Ser Tyr Leu Lys Gly Ser Ala Gly Gly Pro Leu Leu Cys Pro Ser
    530                 535                 540

Gly His Ala Val Gly Ile Phe Arg Ala Ala Val Cys Thr Arg Gly Val
545                 550                 555                 560

Ala Lys Ala Val Asp Phe Val Pro Val Glu Ser Met Glu Thr Thr Met
                565                 570                 575

Arg Ser Pro Val Phe Thr Asp Asn Ser Ser Pro Pro Ala Val Pro Gln
            580                 585                 590

Ser Phe Gln Val Ala His Leu His Ala Pro Thr Gly Ser Gly Lys Ser
        595                 600                 605

Thr Lys Val Pro Ala Ala Tyr Ala Ala Gln Gly Tyr Lys Val Leu Val
    610                 615                 620

Leu Asn Pro Ser Val Ala Ala Thr Leu Gly Phe Gly Ala Tyr Met Ser
```

-continued

```
625                 630                 635                 640

Lys Ala His Gly Ile Asp Pro Asn Ile Arg Thr Gly Val Arg Thr Ile
                645                 650                 655

Thr Thr Gly Ala Pro Val Thr Tyr Ser Thr Tyr Gly Lys Phe Leu Ala
            660                 665                 670

Asp Gly Gly Cys Ser Gly Gly Ala Tyr Asp Ile Ile Ile Cys Asp Glu
        675                 680                 685

Cys His Ser Thr Asp Ser Thr Thr Ile Leu Gly Ile Gly Thr Val Leu
    690                 695                 700

Asp Gln Ala Glu Thr Ala Gly Ala Arg Leu Val Val Leu Ala Thr Ala
705                 710                 715                 720

Thr Pro Pro Gly Ser Val Thr Val Pro His Pro Asn Ile Glu Glu Val
                725                 730                 735

Ala Leu Ser Asn Thr Gly Glu Ile Pro Phe Tyr Gly Lys Ala Ile Pro
            740                 745                 750

Ile Glu Ala Ile Arg Gly Gly Arg His Leu Ile Phe Cys His Ser Lys
        755                 760                 765

Lys Lys Cys Asp Glu Leu Ala Ala Lys Leu Ser Gly Leu Gly Ile Asn
    770                 775                 780

Ala Val Ala Tyr Tyr Arg Gly Leu Asp Val Ser Val Ile Pro Thr Ile
785                 790                 795                 800

Gly Asp Val Val Val Val Ala Thr Asp Ala Leu Met Thr Gly Tyr Thr
                805                 810                 815

Gly Asp Phe Asp Ser Val Ile Asp Cys Asn Thr Cys Val Thr Gln Thr
            820                 825                 830

Val Asp Phe Ser Leu Asp Pro Thr Phe Thr Ile Glu Thr Thr Thr Val
        835                 840                 845

Pro Gln Asp Ala Val Ser Arg Ser Gln Arg Arg Gly Arg Thr Gly Arg
    850                 855                 860

Gly Arg Arg Gly Ile Tyr Arg Phe Val Thr Pro Gly Glu Arg Pro Ser
865                 870                 875                 880

Gly Met Phe Asp Ser Ser Val Leu Cys Glu Cys Tyr Asp Ala Gly Cys
                885                 890                 895

Ala Trp Tyr Glu Leu Thr Pro Ala Glu Thr Ser Val Arg Leu Arg Ala
            900                 905                 910

Tyr Leu Asn Thr Pro Gly Leu Pro Val Cys Gln Asp His Leu Glu Phe
        915                 920                 925

Trp Glu Ser Val Phe Thr Gly Leu Thr His Ile Asp Ala His Phe Leu
    930                 935                 940

Ser Gln Thr Lys Gln Ala Gly Asp Asn Phe Pro Tyr Leu Val Ala Tyr
945                 950                 955                 960

Gln Ala Thr Val Cys Ala Arg Ala Gln Ala Pro Pro Pro Ser Trp Asp
                965                 970                 975

Gln Met Trp Lys Cys Leu Ile Arg Leu Lys Pro Thr Leu His Gly Pro
            980                 985                 990

Thr Pro Leu Leu Tyr Arg Leu Gly Ala Val Gln Asn Glu Val Thr Leu
        995                1000                1005

Thr His Pro Ile Thr Lys Tyr Ile Met Ala Cys Met Ser Ala Asp Leu
   1010                1015                1020

Glu Val Val Thr Ser Thr Trp Val Leu Val Gly Gly Val Leu Ala Ala
1025                1030                1035                1040

Leu Ala Ala Tyr Cys Leu Thr Thr Gly Ser Val Val Ile Val Gly Arg
               1045                1050                1055
```

-continued

```
Ile Ile Leu Ser Gly Arg Pro Ala Ile Val Pro Asp Arg Glu Leu Leu
            1060                1065                1070

Tyr Gln Glu Phe Asp Glu Met Glu Glu Cys Ala Ser His Leu Pro Tyr
        1075                1080                1085

Ile Glu Gln Gly Met Gln Leu Ala Glu Gln Phe Lys Gln Lys Ala Leu
    1090                1095                1100

Gly Leu Leu Gln Thr Ala Thr Lys Gln Ala Glu Ala Ala Ala Pro Val
1105                1110                1115                1120

Val Glu Ser Lys Trp Arg Ala Leu Glu Thr Phe Trp Ala Lys His Met
                1125                1130                1135

Trp Asn Phe Ile Ser Gly Ile Gln Tyr Leu Ala Gly Leu Ser Thr Leu
            1140                1145                1150

Pro Gly Asn Pro Ala Ile Ala Ser Leu Met Ala Phe Thr Ala Ser Ile
        1155                1160                1165

Thr Ser Pro Leu Thr Thr Gln Ser Thr Leu Leu Phe Asn Ile Leu Gly
    1170                1175                1180

Gly Trp Val Ala Ala Gln Leu Ala Pro Pro Ser Ala Ala Ser Ala Phe
1185                1190                1195                1200

Val Gly Ala Gly Ile Ala Gly Ala Ala Val Gly Ser Ile Gly Leu Gly
                1205                1210                1215

Lys Val Leu Val Asp Ile Leu Ala Gly Tyr Gly Ala Gly Val Ala Gly
            1220                1225                1230

Ala Leu Val Ala Phe Lys Val Met Ser Gly Glu Met Pro Ser Thr Glu
        1235                1240                1245

Asp Leu Val Asn Leu Leu Pro Ala Ile Leu Glu Glu Ala Ser Glu Asp
    1250                1255                1260

Val Val Cys Cys Ser Met Ser Tyr Thr Trp Thr Gly Ala Leu Glu Leu
1265                1270                1275                1280

Leu Leu Leu Leu Leu Leu Gly Leu Arg Leu Gln Leu Ser Leu Gly Ile
                1285                1290                1295

Ile Pro Val Glu Glu Glu Asn Pro Asp Phe Trp Asn Arg Glu Ala Ala
            1300                1305                1310

Glu Ala Leu Gly Ala Ala Lys Lys Leu Gln Pro Ala Gln Thr Ala Ala
        1315                1320                1325

Lys Asn Leu Ile Ile Phe Leu Gly Asp Gly Met Gly Val Ser Thr Val
    1330                1335                1340

Thr Ala Ala Arg Ile Leu Lys Gly Gln Lys Lys Asp Lys Leu Gly Pro
1345                1350                1355                1360

Glu Ile Pro Leu Ala Met Asp Arg Phe Pro Tyr Val Ala Leu Ser Lys
                1365                1370                1375

Thr Tyr Asn Val Asp Lys His Val Pro Asp Ser Gly Ala Thr Ala Thr
            1380                1385                1390

Ala Tyr Leu Cys Gly Val Lys Gly Asn Phe Gln Thr Ile Gly Leu Ser
        1395                1400                1405

Ala Ala Ala Arg Phe Asn Gln Cys Asn Thr Thr Arg Gly Asn Glu Val
    1410                1415                1420

Ile Ser Val Met Asn Arg Ala Lys Lys Ala Gly Lys Ser Val Gly Val
1425                1430                1435                1440

Val Thr Thr Thr Arg Val Gln His Ala Ser Pro Ala Gly Thr Tyr Ala
                1445                1450                1455

His Thr Val Asn Arg Asn Trp Tyr Ser Asp Ala Asp Val Pro Ala Ser
            1460                1465                1470
```

-continued

```
Ala Arg Gln Glu Gly Cys Gln Asp Ile Ala Thr Gln Leu Ile Ser Asn
       1475                1480                1485

Met Asp Ile Asp Val Ile Leu Gly Gly Gly Arg Lys Tyr Met Phe Pro
   1490                1495                1500

Met Gly Thr Pro Asp Pro Glu Tyr Pro Asp Asp Tyr Ser Gln Gly Gly
1505                1510                1515                1520

Thr Arg Leu Asp Gly Lys Asn Leu Val Gln Glu Trp Leu Ala Lys Arg
               1525                1530                1535

Gln Gly Ala Arg Tyr Val Trp Asn Arg Thr Glu Leu Met Gln Ala Ser
           1540                1545                1550

Leu Asp Pro Ser Val Thr His Leu Met Gly Leu Phe Glu Pro Gly Asp
       1555                1560                1565

Met Lys Tyr Glu Ile His Arg Asp Ser Thr Leu Asp Pro Ser Leu Met
   1570                1575                1580

Glu Met Thr Glu Ala Ala Leu Arg Leu Leu Ser Arg Asn Pro Arg Gly
1585                1590                1595                1600

Phe Phe Leu Phe Val Glu Gly Gly Arg Ile Asp His Gly His His Glu
               1605                1610                1615

Ser Arg Ala Tyr Arg Ala Leu Thr Glu Thr Ile Met Phe Asp Asp Ala
           1620                1625                1630

Ile Glu Arg Ala Gly Gln Leu Thr Ser Glu Glu Asp Thr Leu Ser Leu
       1635                1640                1645

Val Thr Ala Asp His Ser His Val Phe Ser Phe Gly Gly Tyr Pro Leu
   1650                1655                1660

Arg Gly Ser Cys Ile Phe Gly Leu Ala Pro Gly Lys Ala Arg Asp Arg
1665                1670                1675                1680

Lys Ala Tyr Thr Val Leu Leu Tyr Gly Asn Gly Pro Gly Tyr Val Leu
               1685                1690                1695

Lys Asp Gly Ala Arg Pro Asp Val Thr Glu Ser Glu Ser Gly Ser Pro
           1700                1705                1710

Glu Tyr Arg Gln Gln Ser Ala Val Pro Leu Asp Glu Glu Thr His Ala
       1715                1720                1725

Gly Glu Asp Val Ala Val Phe Ala Arg Gly Pro Gln Ala His Leu Val
   1730                1735                1740

His Gly Val Gln Glu Gln Thr Phe Ile Ala His Val Met Ala Phe Ala
1745                1750                1755                1760

Ala Cys Leu Glu Pro Tyr Thr Ala Cys Asp Leu Ala Pro Pro Ala Gly
               1765                1770                1775

Thr Thr Asp Ala Ala His Pro Gly Met Ser Glu Lys Tyr Ile Val Thr
           1780                1785                1790

Trp Asp Met Leu Gln Ile His Ala Arg Lys Leu Ala Ser Arg Leu Met
       1795                1800                1805

Pro Ser Glu Gln Trp Lys Gly Ile Ile Ala Val Ser Arg Gly Gly Leu
   1810                1815                1820

Val Pro Gly Ala Leu Leu Ala Arg Glu Leu Gly Ile Arg His Val Asp
1825                1830                1835                1840

Thr Val Cys Ile Ser Ser Tyr Asp His Asp Asn Gln Arg Glu Leu Lys
               1845                1850                1855

Val Leu Lys Arg Ala Glu Gly Asp Gly Glu Gly Phe Ile Val Ile Asp
           1860                1865                1870

Asp Leu Val Asp Thr Gly Gly Thr Ala Val Ala Ile Arg Glu Met Tyr
       1875                1880                1885

Pro Lys Ala His Phe Val Thr Ile Phe Ala Lys Pro Ala Gly Arg Pro
```

-continued

```
   1890                1895                1900

Leu Val Asp Asp Tyr Val Val Asp Ile Pro Gln Asp Thr Trp Ile Glu
1905                1910                1915                1920

Gln Pro Trp Asp Met Gly Val Val Phe Val Pro Pro Ile Ser Gly Arg
               1925                1930                1935

Phe Cys Glu Arg Met Ala Asn Glu Gly Lys Ile Val Ile Val Ala Ala
           1940                1945                1950

Leu Asp Gly Thr Phe Gln Arg Lys Pro Phe Asn Asn Ile Leu Asn Leu
       1955                1960                1965

Ile Pro Leu Ser Glu Met Val Val Lys Leu Thr Ala Val Cys Met Lys
   1970                1975                1980

Cys Phe Lys Glu Ala Ser Phe Ser Lys Arg Leu Gly Glu Glu Thr Glu
1985                1990                1995                2000

Ile Glu Ile Ile Gly Gly Asn Asp Met Tyr Gln Ser Val Cys Arg Lys
               2005                2010                2015

Cys Tyr Ile Asp Ser Met Ser Ile Gln His Phe Arg Val Ala Leu Ile
           2020                2025                2030

Pro Phe Phe Ala Ala Phe Cys Leu Pro Val Phe Ala His Pro Glu Thr
       2035                2040                2045

Leu Val Lys Val Lys Asp Ala Glu Asp Gln Leu Gly Ala Arg Val Gly
   2050                2055                2060

Tyr Ile Glu Leu Asp Leu Asn Ser Gly Lys Ile Leu Glu Ser Phe Arg
2065                2070                2075                2080

Pro Glu Glu Arg Phe Pro Met Met Ser Thr Phe Lys Val Leu Leu Cys
               2085                2090                2095

Gly Ala Val Leu Ser Arg Ile Asp Ala Gly Gln Glu Gln Leu Gly Arg
           2100                2105                2110

Arg Ile His Tyr Ser Gln Asn Asp Leu Val Glu Tyr Ser Pro Val Thr
       2115                2120                2125

Glu Lys His Leu Thr Asp Gly Met Thr Val Arg Glu Leu Cys Ser Ala
   2130                2135                2140

Ala Ile Thr Met Ser Asp Asn Thr Ala Ala Asn Leu Leu Leu Thr Thr
2145                2150                2155                2160

Ile Gly Gly Pro Lys Glu Leu Thr Ala Phe Leu His Asn Met Gly Asp
               2165                2170                2175

His Val Thr Arg Leu Asp Arg Trp Glu Pro Glu Leu Asn Glu Ala Ile
           2180                2185                2190

Pro Asn Asp Glu Arg Asp Thr Thr Met Pro Val Ala Met Ala Thr Thr
       2195                2200                2205

Leu Arg Lys Leu Leu Thr Gly Glu Leu Leu Thr Leu Ala Ser Arg Gln
   2210                2215                2220

Gln Leu Ile Asp Trp Met Glu Ala Asp Lys Val Ala Gly Pro Leu Leu
2225                2230                2235                2240

Arg Ser Ala Leu Pro Ala Gly Trp Phe Ile Ala Asp Lys Ser Gly Ala
               2245                2250                2255

Gly Glu Arg Gly Ser Arg Gly Ile Ile Ala Ala Leu Gly Pro Asp Gly
           2260                2265                2270

Lys Pro Ser Arg Ile Val Val Ile Tyr Thr Thr Gly Ser Gln Ala Thr
       2275                2280                2285

Met Asp Glu Arg Asn Arg Gln Ile Ala Glu Ile Gly Ala Ser Leu Ile
   2290                2295                2300

Lys His Trp
2305
```

<210> SEQ ID NO 17
<211> LENGTH: 92
<212> TYPE: PRT
<213> ORGANISM: Artificial Sequence
<220> FEATURE:
<223> OTHER INFORMATION: :

<400> SEQUENCE: 17

```
Met Asn Gly Gly His Ile Gln Leu Ile Ile Gly Pro Met Phe Ser Gly
  1               5                  10                  15

Lys Ser Thr Glu Leu Ile Arg Arg Val Arg Arg Tyr Gln Ile Ala Gln
             20                  25                  30

Tyr Lys Cys Val Thr Ile Lys Tyr Ser Asn Asp Asn Arg Tyr Gly Thr
         35                  40                  45

Gly Leu Trp Thr His Asp Lys Asn Asn Phe Glu Ala Leu Glu Ala Thr
     50                  55                  60

Lys Leu Cys Asp Val Leu Glu Ser Ile Thr Asp Phe Ser Val Ile Gly
 65                  70                  75                  80

Ile Asp Glu Gly Gln Phe Phe Pro Asp Ile Val Glu
                 85                  90
```

<210> SEQ ID NO 18
<211> LENGTH: 1692
<212> TYPE: PRT
<213> ORGANISM: Artificial Sequence
<220> FEATURE:
<223> OTHER INFORMATION: :

<400> SEQUENCE: 18

```
Met Gly Ile Pro Gln Phe Met Ala Arg Val Cys Ala Cys Leu Trp Met
  1               5                  10                  15

Met Leu Leu Ile Ala Gln Ala Glu Ala Ala Leu Glu Asn Leu Val Val
             20                  25                  30

Leu Asn Ala Ala Ser Val Ala Gly Ala His Gly Ile Leu Ser Phe Leu
         35                  40                  45

Val Phe Phe Cys Ala Ala Trp Tyr Ile Lys Gly Arg Leu Val Pro Gly
     50                  55                  60

Ala Ala Tyr Ala Leu Tyr Gly Val Trp Pro Leu Leu Leu Leu Leu Leu
 65                  70                  75                  80

Ala Leu Pro Pro Arg Ala Tyr Ala Met Asp Arg Glu Met Ala Ala Ser
                 85                  90                  95

Cys Gly Gly Ala Val Phe Val Gly Leu Val Leu Leu Thr Leu Ser Pro
            100                 105                 110

Tyr Tyr Lys Val Phe Leu Ala Arg Leu Ile Trp Trp Leu Gln Tyr Phe
        115                 120                 125

Thr Thr Arg Ala Glu Ala His Leu His Val Trp Ile Pro Pro Leu Asn
    130                 135                 140

Ala Arg Gly Gly Arg Asp Ala Ile Ile Leu Leu Met Cys Ala Val His
145                 150                 155                 160

Pro Glu Leu Ile Phe Asp Ile Thr Lys Leu Leu Ile Ala Ile Leu Gly
                165                 170                 175

Pro Leu Met Val Leu Gln Ala Gly Ile Thr Arg Val Pro Tyr Phe Val
            180                 185                 190

Arg Ala Gln Gly Leu Ile His Ala Cys Met Leu Val Arg Lys Val Ala
        195                 200                 205

Gly Gly His Tyr Val Gln Met Ala Phe Met Lys Leu Gly Ala Leu Thr
```

-continued

```
    210                 215                 220

Gly Thr Tyr Ile Tyr Asn His Leu Thr Pro Leu Arg Asp Trp Ala His
225                 230                 235                 240

Ala Gly Leu Arg Asp Leu Ala Val Ala Val Glu Pro Val Val Phe Ser
                245                 250                 255

Asp Met Glu Thr Lys Ile Ile Thr Trp Gly Ala Asp Thr Ala Ala Ala
            260                 265                 270

Gly Asp Ile Ile Leu Gly Leu Pro Val Ser Ala Arg Arg Gly Lys Glu
        275                 280                 285

Ile Leu Leu Gly Pro Ala Asp Ser Leu Glu Gly Arg Gly Trp Arg Leu
    290                 295                 300

Leu Ala Pro Ile Thr Ala Tyr Ser Gln Gln Thr Arg Gly Leu Leu Gly
305                 310                 315                 320

Cys Ile Ile Thr Ser Leu Thr Gly Arg Asp Lys Asn Gln Val Glu Gly
                325                 330                 335

Glu Val Gln Val Val Ser Thr Ala Thr Gln Ser Phe Leu Ala Thr Cys
            340                 345                 350

Val Asn Gly Val Cys Trp Thr Val Tyr His Gly Ala Gly Ser Lys Thr
        355                 360                 365

Leu Ala Gly Pro Lys Gly Pro Ile Thr Gln Met Tyr Thr Asn Val Asp
    370                 375                 380

Gln Asp Leu Val Gly Trp Gln Ala Pro Pro Gly Ala Arg Ser Leu Thr
385                 390                 395                 400

Pro Cys Thr Cys Gly Ser Ser Asp Leu Tyr Leu Val Thr Arg His Ala
                405                 410                 415

Asp Val Ile Pro Val Arg Arg Arg Gly Asp Ser Arg Gly Ser Leu Leu
            420                 425                 430

Ser Pro Arg Pro Val Ser Tyr Leu Lys Gly Ser Ala Gly Gly Pro Leu
        435                 440                 445

Leu Cys Pro Ser Gly His Ala Val Gly Ile Phe Arg Ala Ala Val Cys
    450                 455                 460

Thr Arg Gly Val Ala Lys Ala Val Asp Phe Val Pro Val Glu Ser Met
465                 470                 475                 480

Glu Thr Thr Met Arg Ser Pro Val Phe Thr Asp Asn Ser Ser Pro Pro
                485                 490                 495

Ala Val Pro Gln Ser Phe Gln Val Ala His Leu His Ala Pro Thr Gly
            500                 505                 510

Ser Gly Lys Ser Thr Lys Val Pro Ala Ala Tyr Ala Ala Gln Gly Tyr
        515                 520                 525

Lys Val Leu Val Leu Asn Pro Ser Val Ala Ala Thr Leu Gly Phe Gly
    530                 535                 540

Ala Tyr Met Ser Lys Ala His Gly Ile Asp Pro Asn Ile Arg Thr Gly
545                 550                 555                 560

Val Arg Thr Ile Thr Thr Gly Ala Pro Val Thr Tyr Ser Thr Tyr Gly
                565                 570                 575

Lys Phe Leu Ala Asp Gly Gly Cys Ser Gly Gly Ala Tyr Asp Ile Ile
            580                 585                 590

Ile Cys Asp Glu Cys His Ser Thr Asp Ser Thr Thr Ile Leu Gly Ile
        595                 600                 605

Gly Thr Val Leu Asp Gln Ala Glu Thr Ala Gly Ala Arg Leu Val Val
    610                 615                 620

Leu Ala Thr Ala Thr Pro Pro Gly Ser Val Thr Val Pro His Pro Asn
625                 630                 635                 640
```

-continued

```
Ile Glu Glu Val Ala Leu Ser Asn Thr Gly Glu Ile Pro Phe Tyr Gly
                645                 650                 655

Lys Ala Ile Pro Ile Glu Ala Ile Arg Gly Gly Arg His Leu Ile Phe
            660                 665                 670

Cys His Ser Lys Lys Lys Cys Asp Glu Leu Ala Ala Lys Leu Ser Gly
        675                 680                 685

Leu Gly Ile Asn Ala Val Ala Tyr Tyr Arg Gly Leu Asp Val Ser Val
    690                 695                 700

Ile Pro Thr Ile Gly Asp Val Val Val Val Ala Thr Asp Ala Leu Met
705                 710                 715                 720

Thr Gly Tyr Thr Gly Asp Phe Asp Ser Val Ile Asp Cys Asn Thr Cys
                725                 730                 735

Val Thr Gln Thr Val Asp Phe Ser Leu Asp Pro Thr Phe Thr Ile Glu
            740                 745                 750

Thr Thr Thr Val Pro Gln Asp Ala Val Ser Arg Ser Gln Arg Arg Gly
        755                 760                 765

Arg Thr Gly Arg Gly Arg Arg Gly Ile Tyr Arg Phe Val Thr Pro Gly
    770                 775                 780

Glu Arg Pro Ser Gly Met Phe Asp Ser Ser Val Leu Cys Glu Cys Tyr
785                 790                 795                 800

Asp Ala Gly Cys Ala Trp Tyr Glu Leu Thr Pro Ala Glu Thr Ser Val
                805                 810                 815

Arg Leu Arg Ala Tyr Leu Asn Thr Pro Gly Leu Pro Val Cys Gln Asp
            820                 825                 830

His Leu Glu Phe Trp Glu Ser Val Phe Thr Gly Leu Thr His Ile Asp
        835                 840                 845

Ala His Phe Leu Ser Gln Thr Lys Gln Ala Gly Asp Asn Phe Pro Tyr
    850                 855                 860

Leu Val Ala Tyr Gln Ala Thr Val Cys Ala Arg Ala Gln Ala Pro Pro
865                 870                 875                 880

Pro Ser Trp Asp Gln Met Trp Lys Cys Leu Ile Arg Leu Lys Pro Thr
                885                 890                 895

Leu His Gly Pro Thr Pro Leu Leu Tyr Arg Leu Gly Ala Val Gln Asn
            900                 905                 910

Glu Val Thr Leu Thr His Pro Ile Thr Lys Tyr Ile Met Ala Cys Met
        915                 920                 925

Ser Ala Asp Leu Glu Val Val Thr Ser Thr Trp Val Leu Val Gly Gly
    930                 935                 940

Val Leu Ala Ala Leu Ala Ala Tyr Cys Leu Thr Thr Gly Ser Val Val
945                 950                 955                 960

Ile Val Gly Arg Ile Ile Leu Ser Gly Arg Pro Ala Ile Val Pro Asp
                965                 970                 975

Arg Glu Leu Leu Tyr Gln Glu Phe Asp Glu Met Glu Glu Cys Ala Ser
            980                 985                 990

His Leu Pro Tyr Ile Glu Gln Gly Met Gln Leu Ala Glu Gln Phe Lys
        995                1000                1005

Gln Lys Ala Leu Gly Leu Leu Gln Thr Ala Thr Lys Gln Ala Glu Ala
   1010                1015                1020

Ala Ala Pro Val Val Glu Ser Lys Trp Arg Ala Leu Glu Thr Phe Trp
1025               1030                1035                1040

Ala Lys His Met Trp Asn Phe Ile Ser Gly Ile Gln Tyr Leu Ala Gly
               1045                1050                1055
```

-continued

```
Leu Ser Thr Leu Pro Gly Asn Pro Ala Ile Ala Ser Leu Met Ala Phe
            1060                1065                1070

Thr Ala Ser Ile Thr Ser Pro Leu Thr Thr Gln Ser Thr Leu Leu Phe
        1075                1080                1085

Asn Ile Leu Gly Gly Trp Val Ala Ala Gln Leu Ala Pro Pro Ser Ala
    1090                1095                1100

Ala Ser Ala Phe Val Gly Ala Gly Ile Ala Gly Ala Ala Val Gly Ser
1105                1110                1115                1120

Ile Gly Leu Gly Lys Val Leu Val Asp Ile Leu Ala Gly Tyr Gly Ala
                1125                1130                1135

Gly Val Ala Gly Ala Leu Val Ala Phe Lys Val Met Ser Gly Glu Met
            1140                1145                1150

Pro Ser Thr Glu Asp Leu Val Asn Leu Leu Pro Ala Ile Leu Glu Glu
        1155                1160                1165

Ala Ser Glu Asp Val Val Cys Cys Ser Met Ser Tyr Thr Trp Thr Gly
    1170                1175                1180

Ala Leu Glu Leu Leu Leu Leu Leu Leu Leu Gly Leu Arg Leu Gln Leu
1185                1190                1195                1200

Ser Leu Gly Ile Ile Pro Val Glu Glu Glu Asn Pro Asp Phe Trp Asn
                1205                1210                1215

Arg Glu Ala Ala Glu Ala Leu Gly Ala Ala Lys Lys Leu Gln Pro Ala
            1220                1225                1230

Gln Thr Ala Ala Lys Asn Leu Ile Ile Phe Leu Gly Asp Gly Met Gly
        1235                1240                1245

Val Ser Thr Val Thr Ala Ala Arg Ile Leu Lys Gly Gln Lys Lys Asp
    1250                1255                1260

Lys Leu Gly Pro Glu Ile Pro Leu Ala Met Asp Arg Phe Pro Tyr Val
1265                1270                1275                1280

Ala Leu Ser Lys Thr Tyr Asn Val Asp Lys His Val Pro Asp Ser Gly
                1285                1290                1295

Ala Thr Ala Thr Ala Tyr Leu Cys Gly Val Lys Gly Asn Phe Gln Thr
            1300                1305                1310

Ile Gly Leu Ser Ala Ala Ala Arg Phe Asn Gln Cys Asn Thr Thr Arg
        1315                1320                1325

Gly Asn Glu Val Ile Ser Val Met Asn Arg Ala Lys Lys Ala Gly Lys
    1330                1335                1340

Ser Val Gly Val Val Thr Thr Thr Arg Val Gln His Ala Ser Pro Ala
1345                1350                1355                1360

Gly Thr Tyr Ala His Thr Val Asn Arg Asn Trp Tyr Ser Asp Ala Asp
                1365                1370                1375

Val Pro Ala Ser Ala Arg Gln Glu Gly Cys Gln Asp Ile Ala Thr Gln
            1380                1385                1390

Leu Ile Ser Asn Met Asp Ile Asp Val Ile Leu Gly Gly Gly Arg Lys
        1395                1400                1405

Tyr Met Phe Pro Met Gly Thr Pro Asp Pro Glu Tyr Pro Asp Asp Tyr
    1410                1415                1420

Ser Gln Gly Gly Thr Arg Leu Asp Gly Lys Asn Leu Val Gln Glu Trp
1425                1430                1435                1440

Leu Ala Lys Arg Gln Gly Ala Arg Tyr Val Trp Asn Arg Thr Glu Leu
                1445                1450                1455

Met Gln Ala Ser Leu Asp Pro Ser Val Thr His Leu Met Gly Leu Phe
            1460                1465                1470

Glu Pro Gly Asp Met Lys Tyr Glu Ile His Arg Asp Ser Thr Leu Asp
```

-continued

```
        1475                1480                1485

Pro Ser Leu Met Glu Met Thr Glu Ala Ala Leu Arg Leu Leu Ser Arg
    1490                1495                1500

Asn Pro Arg Gly Phe Phe Leu Phe Val Glu Gly Gly Arg Ile Asp His
1505                1510                1515                1520

Gly His His Glu Ser Arg Ala Tyr Arg Ala Leu Thr Glu Thr Ile Met
                1525                1530                1535

Phe Asp Asp Ala Ile Glu Arg Ala Gly Gln Leu Thr Ser Glu Glu Asp
            1540                1545                1550

Thr Leu Ser Leu Val Thr Ala Asp His Ser His Val Phe Ser Phe Gly
        1555                1560                1565

Gly Tyr Pro Leu Arg Gly Ser Cys Ile Phe Gly Leu Ala Pro Gly Lys
    1570                1575                1580

Ala Arg Asp Arg Lys Ala Tyr Thr Val Leu Leu Tyr Gly Asn Gly Pro
1585                1590                1595                1600

Gly Tyr Val Leu Lys Asp Gly Ala Arg Pro Asp Val Thr Glu Ser Glu
                1605                1610                1615

Ser Gly Ser Pro Glu Tyr Arg Gln Gln Ser Ala Val Pro Leu Asp Glu
            1620                1625                1630

Glu Thr His Ala Gly Glu Asp Val Ala Val Phe Ala Arg Gly Pro Gln
        1635                1640                1645

Ala His Leu Val His Gly Val Gln Glu Gln Thr Phe Ile Ala His Val
    1650                1655                1660

Met Ala Phe Ala Ala Cys Leu Glu Pro Tyr Thr Ala Cys Asp Leu Ala
1665                1670                1675                1680

Pro Pro Ala Gly Thr Thr Asp Ala Ala His Pro Gly
                1685                1690


<210> SEQ ID NO 19
<211> LENGTH: 152
<212> TYPE: PRT
<213> ORGANISM: Artificial Sequence
<220> FEATURE:
<223> OTHER INFORMATION: :

<400> SEQUENCE: 19

Met Ser Glu Lys Tyr Ile Val Thr Trp Asp Met Leu Gln Ile His Ala
  1               5                  10                  15

Arg Lys Leu Ala Ser Arg Leu Met Pro Ser Glu Gln Trp Lys Gly Ile
             20                  25                  30

Ile Ala Val Ser Arg Gly Gly Leu Val Pro Gly Ala Leu Leu Ala Arg
         35                  40                  45

Glu Leu Gly Ile Arg His Val Asp Thr Val Cys Ile Ser Ser Tyr Asp
     50                  55                  60

His Asp Asn Gln Arg Glu Leu Lys Val Leu Lys Arg Ala Glu Gly Asp
 65                  70                  75                  80

Gly Glu Gly Phe Ile Val Ile Asp Asp Leu Val Asp Thr Gly Gly Thr
                 85                  90                  95

Ala Val Ala Ile Arg Glu Met Tyr Pro Lys Ala His Phe Val Thr Ile
            100                 105                 110

Phe Ala Lys Pro Ala Gly Arg Pro Leu Val Asp Asp Tyr Val Val Asp
        115                 120                 125

Ile Pro Gln Asp Thr Trp Ile Glu Gln Pro Trp Asp Met Gly Val Val
    130                 135                 140

Phe Val Pro Pro Ile Ser Gly Arg
```

145 150

<210> SEQ ID NO 20
<211> LENGTH: 85
<212> TYPE: PRT
<213> ORGANISM: Artificial Sequence
<220> FEATURE:
<223> OTHER INFORMATION: :

<400> SEQUENCE: 20

```
Phe Cys Glu Arg Met Ala Asn Glu Gly Lys Ile Val Ile Val Ala Ala
  1               5                  10                  15

Leu Asp Gly Thr Phe Gln Arg Lys Pro Phe Asn Asn Ile Leu Asn Leu
             20                  25                  30

Ile Pro Leu Ser Glu Met Val Val Lys Leu Thr Ala Val Cys Met Lys
         35                  40                  45

Cys Phe Lys Glu Ala Ser Phe Ser Lys Arg Leu Gly Glu Glu Thr Glu
     50                  55                  60

Ile Glu Ile Ile Gly Gly Asn Asp Met Tyr Gln Ser Val Cys Arg Lys
 65                  70                  75                  80

Cys Tyr Ile Asp Ser
                 85
```

<210> SEQ ID NO 21
<211> LENGTH: 286
<212> TYPE: PRT
<213> ORGANISM: Artificial Sequence
<220> FEATURE:
<223> OTHER INFORMATION: :

<400> SEQUENCE: 21

```
Met Ser Ile Gln His Phe Arg Val Ala Leu Ile Pro Phe Phe Ala Ala
  1               5                  10                  15

Phe Cys Leu Pro Val Phe Ala His Pro Glu Thr Leu Val Lys Val Lys
             20                  25                  30

Asp Ala Glu Asp Gln Leu Gly Ala Arg Val Gly Tyr Ile Glu Leu Asp
         35                  40                  45

Leu Asn Ser Gly Lys Ile Leu Glu Ser Phe Arg Pro Glu Glu Arg Phe
     50                  55                  60

Pro Met Met Ser Thr Phe Lys Val Leu Leu Cys Gly Ala Val Leu Ser
 65                  70                  75                  80

Arg Ile Asp Ala Gly Gln Glu Gln Leu Gly Arg Arg Ile His Tyr Ser
                 85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205
```

-continued

```
Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp
        275                 280                 285


<210> SEQ ID NO 22
<211> LENGTH: 220
<212> TYPE: DNA
<213> ORGANISM: Artificial Sequence
<220> FEATURE:
<223> OTHER INFORMATION: Description of Artificial Sequence: Sac
      1/SEAP/Bam H1 construct

<400> SEQUENCE: 22

gcgcgcgagc tcctgctgct gctgctgctg ggcctgaggc tacagctctc cctgggcatc      60

atcccagttg aggaggagaa cccggacttc tggaaccgcg aggcagccga ggccctgggt     120

gccgccaaga agctgcagcc tgcacagaca gccgccaaga acctcatcat cttcctgggc     180

gatgggatgg gggtgtctac ggtgacagct gccaggatcc                           220


<210> SEQ ID NO 23
<211> LENGTH: 88
<212> TYPE: PRT
<213> ORGANISM: Artificial Sequence
<220> FEATURE:
<223> OTHER INFORMATION: Description of Artificial Sequence: amino acid
      fragment of the HCV polyprotein

<400> SEQUENCE: 23

Ala Arg Val Cys Ala Cys Leu Trp Met Met Leu Leu Ile Ala Gln Ala
  1               5                  10                  15

Glu Ala Ala Leu Glu Asn Leu Val Val Leu Asn Ser Ala Ser Val Ala
            20                  25                  30

Gly Ala His Gly Ile Leu Ser Phe Leu Val Phe Phe Cys Ala Ala Trp
        35                  40                  45

Tyr Ile Lys Gly Arg Leu Val Pro Gly Ala Thr Tyr Ala Leu Tyr Gly
    50                  55                  60

Val Trp Pro Leu Leu Leu Leu Leu Leu Ala Leu Pro Pro Arg Ala Tyr
 65                  70                  75                  80

Ala Met Asp Arg Glu Met Ala Ala
                85


<210> SEQ ID NO 24
<211> LENGTH: 260
<212> TYPE: DNA
<213> ORGANISM: Artificial Sequence
<220> FEATURE:
<223> OTHER INFORMATION: Description of Artificial Sequence: DNA
      fragment coding for an amino acid fragment of the HCV
      polyprotein

<400> SEQUENCE: 24

gcacgtgtct gtgcctgctt gtggatgatg ctgctgatag cccaggccga ggccgccttg      60

gagaacctgg tggtcctcaa tgcggcgtct gtggccggcg cacatggcat cctctccttc     120
```

-continued

```
cttgtgttct tctgtgccgc ctggtacatc aaaggcaggc tggtccctgg ggcggcatat    180

gctctttatg gcgtgtggcc gctgctcctg ctcttgctgg cattaccacc gcgagcttac    240

gccatggacc gggagatggc                                                260


<210> SEQ ID NO 25
<211> LENGTH: 177
<212> TYPE: PRT
<213> ORGANISM: Artificial Sequence
<220> FEATURE:
<223> OTHER INFORMATION: Description of Artificial Sequence: amino acid
      fragment of the HCV polyprotein

<400> SEQUENCE: 25

Cys Ala Ser His Leu Pro Tyr Ile Glu Gln Gly Met Gln Leu Ala Glu
  1               5                  10                  15

Gln Phe Lys Gln Lys Ala Leu Gly Leu Leu Gln Thr Ala Thr Lys Gln
             20                  25                  30

Ala Glu Ala Ala Ala Pro Val Val Glu Ser Lys Trp Arg Ala Leu Glu
         35                  40                  45

Thr Phe Trp Ala Lys His Met Trp Asn Phe Ile Ser Gly Ile Gln Tyr
     50                  55                  60

Leu Ala Gly Leu Ser Thr Leu Pro Gly Asn Pro Ala Ile Ala Ser Leu
 65                  70                  75                  80

Met Ala Phe Thr Ala Ser Ile Thr Ser Pro Leu Thr Thr Gln Ser Thr
                 85                  90                  95

Leu Leu Phe Asn Ile Leu Gly Gly Trp Val Ala Ala Gln Leu Ala Pro
            100                 105                 110

Pro Ser Ala Ala Ser Ala Phe Val Gly Ala Gly Ile Ala Gly Ala Ala
        115                 120                 125

Val Gly Ser Ile Gly Leu Gly Lys Val Leu Val Asp Ile Leu Ala Gly
    130                 135                 140

Tyr Gly Ala Gly Val Ala Gly Ala Leu Val Ala Phe Lys Val Met Ser
145                 150                 155                 160

Gly Glu Met Pro Ser Thr Glu Asp Leu Val Asn Leu Leu Pro Ala Ile
                165                 170                 175

Leu


<210> SEQ ID NO 26
<211> LENGTH: 528
<212> TYPE: DNA
<213> ORGANISM: Artificial Sequence
<220> FEATURE:
<223> OTHER INFORMATION: Description of Artificial Sequence: DNA
      fragment coding for an amino acid fragment of the HCV
      polyprotein

<400> SEQUENCE: 26

tgcgcctcgc acctccctta catcgagcag ggaatgcagc tcgccgagca attcaagcag     60

aaagcgctcg ggttactgca aacagccacc aaacaagcgg aggctgctgc tcccgtggtg    120

gagtccaagt ggcgagccct tgagacattc tgggcgaagc acatgtggaa tttcatcagc    180

gggatacagt acttagcagg cttatccact ctgcctggga accccgcaat agcatcattg    240

atggcattca cagcctctat caccagcccg ctcaccaccc aaagtaccct cctgtttaac    300

atcttggggg ggtgggtggc tgcccaactc gcccccccca gcgccgcttc ggctttcgtg    360

ggcgccggca tcgccggtgc ggctgttggc agcataggcc ttgggaaggt gcttgtggac    420

attctggcgg gttatggagc aggagtggcc ggcgcgctcg tggcctttaa ggtcatgagc    480
```

-continued

```
ggcgagatgc cctccaccga ggacctggtc aatctacttc ctgccatc             528


<210> SEQ ID NO 27
<211> LENGTH: 33
<212> TYPE: DNA
<213> ORGANISM: primer

<400> SEQUENCE: 27

gcgcgcgaat tcatggcacg tgtctgtgcc tgc                              33


<210> SEQ ID NO 28
<211> LENGTH: 33
<212> TYPE: DNA
<213> ORGANISM: primer

<400> SEQUENCE: 28

cgcgcgctcg aggatggcag gaagtagatt gac                              33


<210> SEQ ID NO 29
<211> LENGTH: 20
<212> TYPE: PRT
<213> ORGANISM: putative NS5A/5B cleavage site

<400> SEQUENCE: 29

Glu Glu Ala Ser Glu Asp Val Val Cys Cys Ser Met Ser Tyr Thr Trp
  1               5                  10                  15

Thr Gly Ala Leu
             20


<210> SEQ ID NO 30
<211> LENGTH: 33
<212> TYPE: DNA
<213> ORGANISM: primer

<400> SEQUENCE: 30

gcgcgcctcg aggaagctag tgaggatgtc gtc                              33


<210> SEQ ID NO 31
<211> LENGTH: 36
<212> TYPE: DNA
<213> ORGANISM: primer

<400> SEQUENCE: 31

cgcgcggagc tccaaggcgc ctgtccatgt gtagga                           36


<210> SEQ ID NO 32
<211> LENGTH: 69
<212> TYPE: DNA
<213> ORGANISM: primer

<400> SEQUENCE: 32

ctcgaggaag ctagtgagga tgtcgtctgc tgctcaatgt cctacacatg gacaggcgcc     60

ttggagctc                                                         69


<210> SEQ ID NO 33
<211> LENGTH: 6
<212> TYPE: PRT
<213> ORGANISM: HCV/SEAP 6 amino acid fragment

<400> SEQUENCE: 33

Met Gly Ile Pro Gln Phe
  1               5
```